US012600793B2

(12) United States Patent
Bray et al.

(10) Patent No.: US 12,600,793 B2
(45) Date of Patent: *Apr. 14, 2026**

(54) CHIMERIC ANTIGEN RECEPTORS WITH MAGE-A4 SPECIFICITY AND USES THEREOF

(71) Applicant: Regeneron Pharmaceuticals, Inc., Tarrytown, NY (US)

(72) Inventors: Kevin Bray, Garnerville, NY (US); Frank Delfino, Poughquag, NY (US); David DiLillo, New York, NY (US); Thomas Craig Meagher, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1041 days.

This patent is subject to a terminal disclaimer.

(21) Appl. No.: 17/629,562

(22) PCT Filed: Jul. 24, 2020

(86) PCT No.: PCT/US2020/043567
§ 371 (c)(1),
(2) Date: Jan. 24, 2022

(87) PCT Pub. No.: WO2021/016585
PCT Pub. Date: Jan. 28, 2021

(65) Prior Publication Data
US 2022/0281994 A1 Sep. 8, 2022

Related U.S. Application Data

(60) Provisional application No. 63/021,407, filed on May 7, 2020, provisional application No. 63/020,177, filed on May 5, 2020, provisional application No. 62/878,125, filed on Jul. 24, 2019.

(51) Int. Cl.
| | |
|---|---|
| *C07K 16/30* | (2006.01) |
| *A61K 40/11* | (2025.01) |
| *A61K 40/31* | (2025.01) |
| *A61K 40/42* | (2025.01) |
| *A61P 35/00* | (2006.01) |
| *C07K 14/705* | (2006.01) |
| *C07K 14/725* | (2006.01) |
| *C12N 5/0783* | (2010.01) |

(52) U.S. Cl.
CPC .............. *C07K 16/30* (2013.01); *A61K 40/11* (2025.01); *A61K 40/31* (2025.01); *A61K 40/4268* (2025.01); *A61P 35/00* (2018.01); *C07K 14/7051* (2013.01); *C07K 14/70517* (2013.01); *C07K 14/70521* (2013.01); *C07K 14/70578* (2013.01); *C12N 5/0636* (2013.01); *C12N 5/0638* (2013.01); *A61K 2239/13* (2023.05); *A61K 2239/31* (2023.05); *A61K 2239/38* (2023.05); *A61K 2239/46* (2023.05);

*A61K 2239/57* (2023.05); *C07K 2317/24* (2013.01); *C07K 2317/34* (2013.01); *C07K 2317/55* (2013.01); *C07K 2317/622* (2013.01); *C07K 2319/02* (2013.01)

(58) Field of Classification Search
None
See application file for complete search history.

(56) References Cited

U.S. PATENT DOCUMENTS

| | | | | |
|---|---|---|---|---|
| 11,458,167 | B2 * | 10/2022 | Jensen ................. | A61K 31/713 |
| 11,826,386 | B2 * | 11/2023 | DiLillo ................ | C07K 16/085 |
| 12,291,559 | B2 * | 5/2025 | DiLillo ............ | C07K 14/70578 |
| 2004/0043401 | A1 * | 3/2004 | Sadelain .......... | C07K 14/70521 |
| | | | | 435/325 |
| 2019/0127436 | A1 | 5/2019 | Tribble et al. | |
| 2022/0281994 | A1 * | 9/2022 | Bray ................ | C07K 14/70517 |

FOREIGN PATENT DOCUMENTS

| | | | | |
|---|---|---|---|---|
| EP | 1930433 A1 | 6/2008 | | |
| EP | 3636761 A1 | 4/2020 | | |
| WO | WO-0042185 A1 * | 7/2000 | ............. | C12N 15/62 |

(Continued)

OTHER PUBLICATIONS

Sela-Culang et al. The structural basis of antibody-antigen recognition. Fron. Immuno., vol. 4, Article 302, Oct. 2013. (Year: 2013).*
Koenig et al. Mutational landscape of antibody variable domains reveals a switch modulating the interdomain conformational dynamics and antigen binding. PNAS, E486-E4995, Jan. 5, 2017. (Year: 2017).*
Herold et al. Determinants of the assembly and function of antibody variable domains. Nature Scientific Reports, 7:12276, Sep. 25, 2017. (Year: 2017).*
Duffour et al. A MAGE-A4 peptide presented by HLA-A2 is recognized by cytolytic T lymphocytes. Eur. J. Immunol. 1999. 29: 3329-3337. (Year: 1999).*

(Continued)

*Primary Examiner* — Julie Wu
*Assistant Examiner* — Amy M. Chattin
(74) *Attorney, Agent, or Firm* — Schwabe, Williamson & Wyatt PC; Gabe Amodeo

(57) ABSTRACT

MAGE-A4, or Melanoma-Associated Antigen A4, is a cancer-testis antigen (CTA) on the X chromosome. The present disclosure provides MAGE-A4-specific chimeric antigen receptors and cells expressing such chimeric antigen receptors. In certain embodiments, engineered cells expressing the chimeric antigen receptors of the present disclosure are capable of inhibiting the growth of tumors expressing MAGE-A4. The engineered cells of the present disclosure are useful for the treatment of diseases and disorders in which an upregulated or induced MAGE-A4-targeted immune response is desired and/or therapeutically beneficial. For example, engineered cells expressing the MAGE-A4-specific chimeric antigen receptors of the present disclosure are useful for the treatment of various cancers.

35 Claims, 4 Drawing Sheets

Specification includes a Sequence Listing.

(56) References Cited

FOREIGN PATENT DOCUMENTS

| WO | WO-0055207 | A1 | * | 9/2000 | ........... A61K 39/395 |
|----|------------|-----|----|---------|-------------------------|
| WO | WO-0071565 | A2 | * | 11/2000 | ....... C07K 14/43595 |
| WO | WO-0104310 | A1 | * | 1/2001 | ....... C07K 14/70535 |
| WO | WO-2012079000 | A1 | * | 6/2012 | ............. A61K 35/17 |
| WO | WO-2013044225 | A1 | * | 3/2013 | ........ A61K 47/6851 |
| WO | 2013059885 | A2 | | 5/2013 | |
| WO | WO-2016044811 | A1 | * | 3/2016 | ............. A61K 35/17 |
| WO | 16/199141 | A2 | | 12/2016 | |
| WO | 2016199140 | A1 | | 12/2016 | |
| WO | 2017157972 | A1 | | 9/2017 | |
| WO | 17/174824 | A1 | | 10/2017 | |
| WO | WO-2018112474 | A1 | * | 6/2018 | ........... G01N 33/564 |
| WO | WO-2020072536 | A1 | * | 4/2020 | ........ C07K 14/7051 |
| WO | 2021016585 | A1 | | 1/2021 | |
| WO | 2021030680 | A1 | | 2/2021 | |
| WO | 2021226063 | A1 | | 11/2021 | |

OTHER PUBLICATIONS

Jia et al. Identification of Two Novel HLA-A•0201-Restricted CTL Epitopes Derived from MAGE-A4. Clinical and Developmental Immunology, vol. 2010, Article ID 567594. (Year: 2010).*

Johnson et al. Driving gene-engineered T cell immunotherapy of cancer. Cell Research (2017) 247: 38-58. (Year: 2017).*

Anonymous, "Clinical Safety and Preliminary Efficacy of MAGE-A4 TCR Gene-Modified T Cells to Treat Malignant Tumors," Sep. 27, 2012, XP055737560 [retreived from the internet: URL: https://clinicaltrials.gov/ct2/show/NCT01694472?term=mage-a4&draw=1&rank=1, retrieved on Oct. 7, 2020].

WIPO Application No. PCT/US2020/043567, PCT International Search Report and Written Opinion of the International Searching Authority mailed Oct. 30, 2020.

Marie-Therese Duffour et al., "A MAGE-A4 petide presented by HLA-A2 is recognized by cytolytic T lymphocytes," European Journal of Immunology, vol. (29):3329-3337, (Jan. 1, 1999). ISSN: 0014-2980, DOI: 10.1002/(SICI) 1521-4141(199910)29:10<3329:AID-IMMU3329>3.0.CO;2-7].

Miyahara et al., "ESGCT XXV Anniversary Congress in Collaboration with the German Society for Gene Therapy," Oct. 17-20, 2017; Berlin, Germany; Human Gene Therapy; vol. 28 (No. 12), p. A36. [ISSN: 1043-0342, DOI: 10.1089/hum.2017.29055.abstracts abstract].

Y Akahori et al., "International Conference on Lymphocyte Engineering," Human Gene Therapy, vol. (30, No. 12):A1-A22, London, United Kingdom (2019). [ISSN: 1043-0342, DOI: 1.1089/hum.201929091.abstracts].

Yasushi et al., "J-1036: Development of TCR-like scFv CAR that recognizes MAGE-A4230-239/H;A-A*02:01 complex," Cancer Science (Online); Abstracts of the 76th Annual Meeting of the Japanese Cancer Association, Wiley Japan, JP; Yokohama, Japan; vol. 109 (No. 1), p. 102; Dec. 31, 2017 (2017). [retrieved on Jan. 16, 2018; ISSN: 1349-7006, DOI: 10.1111/CAS.13499].

Qian Sun et al., "T-cell receptor gene therapy targeting melanoma-associated antigen-A4 by silencing of endogenous TCR inhibits tumor growth in mice and human," Cell Death & Disease, vol. (10, No. 7): pp. 1-10; Jun. 17, 2019 (2019) [DOI: 10.1038/s41419-019-1717-8].

WIPO Application No. PCT/US2022/027463, PCT International Search Report and Written Opinion of the International Searching Authority mailed Aug. 16, 2022, 19 pages.

European Patent Office issued Communication pursuant to Rule 114(2) EPC Third Party Observations issued Aug. 9, 2024, pp. 1-3.

Jia et al., "Identification of Two Novel HLA-A 0201-Restricted CTL Epitopes Derived from MAGE-A4," Hindawi Publishing Corporation Clinical and Developmental Immunology, vol. 2010, Article ID 567594, 7 pages. [doi:10.1155/2010/567594].

Ounap et al., "Antibody response against cancer-testis antigens MAGEA4 and MAGEA10 in patients with melanoma," Oncology Letters, vol. 16: 211-218, (2018). [doi:10.3892/ol.2018.8684].

Schirmer et al., "Epigenetic regulation of L1CAM in endometrial carcinoma: comparison to cancer-testis (CT-X) antigens," BMC Cancer, vol. 13 (1560: pp. 1-12, (2013). [http://www.biomedcentral.com/1471-2407/13/156].

* cited by examiner

Plate 1: MAGEA4 31345

| | |
|---|---|
| ◌ A375 |
| ● A375++ |
| ▲ 293T (50:1) |
| HPV-293T (50:1) |
| ⊖ HPV -A375 (50:1) |
| HPV-A375++ (50:1) |
| MOI 0 A375 (50:1) |
| MOI 0 A375++ (50:1) |

Plate 2: MAGEA4 31345

| | |
|---|---|
| ◌ IM9 |
| ● IM9++ |
| ▲ 293T (50:1) |
| HPV-293T(50:1) |
| ⊖ HPV -IM9 (50:1) |
| HPV-IM9++ (50:1) |
| MOI 0 IM9 (50:1) |
| MOI 0 IM9++ (50:1) |

Control CAR T

Anti-HLA-A2/MAGEA4$_{286-294}$ CAR T

Control CAR T

CAR T
Injected 0 of 5
Tumor-free

Anti-HLA-A2/MAGEA4$_{286-294}$ CAR T

CAR T
Injected 3 of 5
Tumor-free

CHIMERIC ANTIGEN RECEPTORS WITH MAGE-A4 SPECIFICITY AND USES THEREOF

CROSS-REFERENCE TO RELATED APPLICATIONS

This application is a U.S. National Stage Application under 35 USC § 371 of PCT/US2020/043567, which claims the benefit under 35 USC § 119(e) of U.S. Provisional Patent Application Nos.: 62/878,125, filed Jul. 24, 2019; 63/020, 177, filed May 5, 2020; and 63/021,407, filed May 7, 2020, each of which is incorporated herein by reference in its entirety for all purposes.

REFERENCE TO A SEQUENCE LISTING

This application incorporates by reference the Sequence Listing submitted in Computer Readable Form as file 10600WO01-Sequence.txt, created on Jul. 24, 2020 and containing 123,650 bytes.

FIELD

The present disclosure provides chimeric antigen receptors (CARs), and engineered cells comprising such CARs, which are specific for Melanoma-Associated Antigen A4 (MAGE-A4), and methods of use thereof.

BACKGROUND

MAGE-A4, or Melanoma-Associated Antigen A4, is a cancer-testis antigen (CTA) on the X chromosome. The function of MAGE-A4 is unknown, but it may be involved in cell cycle progression/regulation, transcriptional control, cell survival and/or apoptosis. For example, overexpression of MAGE-A4 has been shown to promote growth of spontaneously transformed oral keratinocytes and inhibit growth arrest of cells in G1.

MAGE-A4 is abundantly expressed by many tumors of different histological types, such as head and neck squamous cell carcinoma, lung carcinoma, such as non-small cell lung carcinoma, esophageal squamous cell carcinoma, colon carcinoma, bladder cancer, mucosal and cutaneous melanomas, ovarian carcinoma, e.g., serous carcinoma, and uterine carcinoma but, in normal healthy adult tissues, MAGE-A4 expression is restricted to the testes.

The ability of MAGE-A4 antigens to elicit immune responses together with its restricted expression pattern have rendered MAGE-A4 a good candidate for cancer immunotherapy.

Adoptive immunotherapy, which involves the transfer of autologous antigen-specific T cells generated ex vivo, is a promising strategy to treat viral infections and cancer. The T cells used for adoptive immunotherapy can be generated either by expansion of antigen-specific T cells or redirection of T cells through genetic engineering.

Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and heavy chain variable fragments of a monoclonal antibody joined by a flexible linker. The signaling domains for first generation CARs are derived from the cytoplasmic region of the CD3zeta or the Fc receptor gamma chains. First generation CARs have been shown to successfully redirect T-cell cytotoxicity. However, they failed to provide prolonged expansion and anti-tumor activity in vivo. Signaling domains from co-stimulatory molecules, as well as transmembrane and hinge domains have been added to form CARs of second and third generations, leading to some successful therapeutic trials in humans. For example, CAR redirected T cells specific for the B cell differentiation antigen CD19 have shown dramatic efficacy in the treatment of B cell malignancies, while TCR-redirected T cells have shown benefits in patients suffering from solid cancer. Stauss et al. describe strategies to modify therapeutic CARs and TCRs, for use in the treatment of cancer, for example, to enhance the antigen-specific effector function and limit toxicity of engineered T cells (*Current Opinion in Pharmacology* 2015, 24:113-118).

There is an unmet need for new targeting agents based on CARs that specifically bind to MAGE-A4 antigens, as well as methods for producing and using such agents in therapeutic and diagnostic settings.

SUMMARY

The present disclosure provides chimeric antigen receptors (CARs) that were generated against a MAGE-A4 peptide antigen in the context of MHC (HLA-A2). In some embodiments, the CAR sequences have specific binding to the small peptide MAGE-A4 286-294 or MAGE-A4 230-239, presented by HLA-A2.

In an aspect, the present disclosure provides a Melanoma-Associated Antigen A4 (MAGE-A4)-specific chimeric antigen receptor (CAR), wherein said MAGE-A4-specific chimeric antigen receptor interacts with amino acids 286-294 or 230-239, or a portion thereof, of SEQ ID NO: 32, and wherein said MAGE-A4-specific CAR specifically binds to an HLA bound MAGE-A4 polypeptide. In some embodiments, the MAGE-A4-specific CAR comprises, from N-terminus to C-terminus: (a) an extracellular ligand-binding domain comprising an anti-MAGE-A4 antigen-binding domain; (b) a hinge; (c) a transmembrane domain; and (d) a cytoplasmic domain comprising a costimulatory domain and a signaling domain. In some embodiments, the extracellular ligand-binding domain comprises an anti-MAGE-A4 single chain variable fragment (scFv) domain comprising a light chain variable region (LCVR) and a heavy chain variable region (HCVR). In some embodiments, the anti-MAGE-A4 scFv domain comprises a first linker between the LCVR and the HCVR. In some embodiments, the MAGE-A4-specific CAR further comprises a second linker between the extracellular ligand-binding domain and the hinge. In some embodiments, the first linker and the second linker comprise amino acid sequences selected from the group consisting of SEQ ID NOs: 23-26. In some embodiments, the first linker comprises the amino acid sequence of SEQ ID NO: 25 and the second linker comprises the amino acid sequence of SEQ ID NO: 23.

In some embodiments, the hinge, the transmembrane domain, or both, of a MAGE-A4-specific CAR are from a CD8α polypeptide. In some embodiments, the costimulatory domain comprises a 4-1BB costimulatory domain. In some embodiments, the hinge, the transmembrane domain, or both, are from a CD28 polypeptide. In some embodiments, the costimulatory domain comprises a CD28 costimulatory domain. In some embodiments, the signaling domain comprises a CD3zeta signaling domain. In some embodiments, the LCVR comprises the complementarity determining regions (CDRs) of a LCVR comprising an amino acid sequence of SEQ ID NO: 10 or SEQ ID NO: 37. In some embodiments, the LCVR comprises LCDR1-LCDR2-LCDR3 comprising the amino acid sequences, respectively, of SEQ ID NOs: 12-14-16. In some embodiments, the HCVR comprises the CDRs of a HCVR comprising an amino acid sequence of SEQ ID NO: 2. In some embodiments, the HCVR comprises HCDR1-HCDR2-HCDR3 comprising the amino acid sequences, respectively, of SEQ ID NOs: 4-6-8.

In some embodiments, a MAGE-A4-specific CAR comprises an LCVR comprising an amino acid sequence of SEQ ID NO: 10 or SEQ ID NO: 37, or an amino acid sequence having 95%-99% sequence identity to an amino acid sequence of SEQ ID NO: 10 or SEQ ID NO: 37; and an HCVR comprising an amino acid sequence selected from the group consisting of SEQ ID NO: 2, or an amino acid sequence having 95%-99% sequence identity to the amino acid sequence of SEQ ID NO: 2. In some embodiments, the LCVR comprises an amino acid sequence of SEQ ID NO: 10 or SEQ ID NO: 37, and the HCVR comprises an amino acid sequence of SEQ ID NO: 2. In some embodiments, the LCVR comprises the complementarity determining regions (CDRs) of a LCVR comprising an amino acid sequence of SEQ ID NO: 59. In some embodiments, the LCVR comprises LCDR1-LCDR2-LCDR3 comprising the amino acid sequences, respectively, of SEQ ID NOs: 61-63-65. In some embodiments, the HCVR comprises the CDRs of a HCVR comprising an amino acid sequence of SEQ ID NO: 51. In some embodiments, the HCVR comprises HCDR1-HCDR2-HCDR3 comprising the amino acid sequences, respectively, of SEQ ID NOs: 53-55-57. In some embodiments, the MAGE-A4-specific CAR comprises an LCVR comprising an amino acid sequence of SEQ ID NO: 59, or an amino acid sequence having 95%-99% sequence identity to an amino acid sequence of SEQ ID NO: 59; and an HCVR comprising an amino acid sequence of SEQ ID NO: 51, or an amino acid sequence having 95%-99% sequence identity to an amino acid sequence of SEQ ID NO: 51. In some embodiments, the LCVR comprises an amino acid sequence of SEQ ID NO: 59, and the HCVR comprises an amino acid sequence of SEQ ID NO: 51. In some embodiments, the hinge comprises the amino acid sequence of SEQ ID NO: 27. In some embodiments, the transmembrane domain comprises the amino acid sequence of SEQ ID NO: 28. In some embodiments, the 4-1BB costimulatory domain comprises the amino acid sequence of SEQ ID NO: 29. In some embodiments, the hinge comprises the amino acid sequence of SEQ ID NO: 41. In some embodiments, the transmembrane domain comprises the amino acid sequence of SEQ ID NO: 43. In some embodiments, the CD28 costimulatory domain comprises the amino acid sequence of SEQ ID NO: 45. In some embodiments, the CD3zeta signaling domain comprises the amino acid sequence of SEQ ID NO: 30. In some embodiments, the chimeric antigen receptor comprises the amino acid sequence of SEQ ID NO: 22. In some embodiments, the chimeric antigen receptor comprises the amino acid sequence of SEQ ID NO: 39. In some embodiments, the MAGE-A4-specific CAR comprises the amino acid sequence of SEQ ID NO: 47. In some embodiments, the MAGE-A4-specific CAR comprises the amino acid sequence of SEQ ID NO: 71. In some embodiments, the MAGE-A4-specific CAR comprises the amino acid sequence of SEQ ID NO: 73. In some embodiments, the chimeric antigen receptor specifically binds to one or more amino acids at positions 286-294 of SEQ ID NO: 32. In some embodiments, the MAGE-A4-specific CAR specifically binds to one or more amino acids at positions 230-239 of SEQ ID NO: 32. In some embodiments, the HLA is HLA-A2.

In an aspect, the present disclosure provides an isolated nucleic acid molecule encoding a MAGE-A4-specific CAR as described herein. In some embodiments, the isolated nucleic acid molecule comprises a nucleotide sequence of SEQ ID NO: 21. In some embodiments, the isolated nucleic acid molecule comprises a nucleotide sequence of SEQ ID NO: 38. In some embodiments, the isolated nucleic acid molecule comprises a nucleotide sequence of SEQ ID NO: 48. In some embodiments, the isolated nucleic acid molecule comprises a nucleotide sequence of SEQ ID NO: 70. In some embodiments, the isolated nucleic acid molecule comprises a nucleotide sequence of SEQ ID NO: 72. In an aspect, the present disclosure provides a vector comprising the nucleic acid molecule described herein. In some embodiments, the vector is a DNA vector, an RNA vector, a plasmid, a lentivirus vector, an adenovirus vector, or a retroviral vector. In some embodiments, the vector is a lentivirus vector.

In an aspect, the present disclosure provides a cell comprising a nucleic acid molecule as described herein, or a vector as described herein. In some embodiments, the cell is a human T cell. In some embodiments, the engineered cell comprises a chimeric antigen receptor as described herein. In some embodiments, the engineered cell is an immune cell, such as an immune effector cell or a T lymphocyte (e.g., an inflammatory T lymphocyte, a cytotoxic T lymphocyte, a regulatory T lymphocyte, or a helper T lymphocyte). In some embodiments, the engineered cell is a CD8+ cytotoxic T lymphocyte. In some embodiments, the engineered cell is for use in the treatment of a MAGE-A4-expressing cancer such as multiple myeloma or melanoma.

In an aspect, the present disclosure provides an engineered human T cell comprising a chimeric antigen receptor comprising, from N-terminus to C-terminus: (a) an extracellular ligand-binding domain comprising an anti-MAGE-A4 single chain variable fragment (scFv) domain comprising a light chain variable region (LCVR) and a heavy chain variable region (HCVR); (b) a hinge; (c) a transmembrane domain; and (d) a cytoplasmic domain comprising a 4-1BB costimulatory domain or a CD28 costimulatory domain and a CD3zeta signaling domain. In some embodiments, the anti-MAGE-A4 scFv specifically binds to one or more amino acid residues of positions 286-294 of SEQ ID NO: 32. In some embodiments, the scFv domain comprises a HCVR/LCVR amino acid sequence pair comprising the amino acid sequences of SEQ ID NOs: 2/10. In some embodiments, the scFv domain comprises a HCVR/LCVR amino acid sequence pair comprising the amino acid sequences of SEQ ID NOs: 2/37. In some embodiments, the scFv domain specifically binds to one or more amino acid residues of positions 230-239 of SEQ ID NO: 32. In some embodiments, the scFv domain comprises a HCVR/LCVR amino acid sequence pair comprising the amino acid sequences of SEQ ID NOs: 51/59. In some embodiments, the hinge comprises the amino acid sequence of SEQ ID NO: 27. In some embodiments, the transmembrane domain comprises the amino acid sequence of SEQ ID NO: 28. In some embodiments, the 4-1BB costimulatory domain comprises the amino acid sequence of SEQ ID NO: 29. In some embodiments, the hinge comprises the amino acid sequence of SEQ ID NO: 41. In some embodiments, the transmembrane domain comprises the amino acid sequence of SEQ ID NO: 43. In some embodiments, the CD28 costimulatory domain comprises the amino acid sequence of SEQ ID NO: 45. In some embodiments, the CD3zeta signaling domain comprises the amino acid sequence of SEQ ID NO: 30. In some embodiments, the engineered human T cell comprises a chimeric antigen receptor comprising the amino acid sequence of SEQ ID NO: 22. In some embodiments, the engineered human T cell comprises a chimeric antigen receptor comprising the amino acid sequence of SEQ ID NO: 39. In some embodiments, the engineered human T cell comprises a chimeric antigen receptor comprising the amino acid sequence of SEQ ID NO: 47. In some embodiments, the engineered human T cell comprises a chimeric antigen receptor comprising the amino acid sequence of SEQ ID NO: 71. In some embodiments, the engineered human T cell comprises a chimeric antigen receptor comprising the amino acid sequence of SEQ ID NO: 73.

In an aspect, the present disclosure provides a pharmaceutical composition comprising a genetically-modified human T cell and a pharmaceutically acceptable carrier, wherein the genetically-modified human T cell comprises a chimeric antigen receptor as described herein. In some embodiments, the pharmaceutical composition comprises the engineered cell or engineered human T cell as described herein, and a pharmaceutically acceptable carrier. In some embodiments, the pharmaceutical composition is for use in the treatment of a MAGE-A4-expressing cancer, such as multiple myeloma or melanoma.

In an aspect, the present disclosure provides a use of a chimeric antigen receptor as described herein, a nucleic acid molecule as described herein, a vector as described herein, a cell as described herein, an engineered cell as described herein, or an engineered human T cell as described herein, in the manufacture of a medicament for the treatment of a MAGE-A4-expressing cancer such as multiple myeloma or melanoma.

In an aspect, the present disclosure provides a method of enhancing T lymphocyte activity in a subject comprising, introducing into the subject a T lymphocyte comprising a chimeric antigen receptor as described herein. In an aspect, the present disclosure provides a method for treating a subject suffering from cancer comprising, introducing into the subject a therapeutically effective amount of a T lymphocyte comprising a chimeric antigen receptor as described herein. In an aspect, the present disclosure provides a method for stimulating a T cell-mediated immune response to a target cell population or tissue in a subject comprising, administering to the subject an effective amount of a cell genetically modified to express a chimeric antigen receptor as described herein. In an aspect, the present disclosure provides a method of providing anti-tumor immunity in a subject, the method comprising administering to the subject an effective amount of a cell genetically modified to express a chimeric antigen receptor as described herein. In some embodiments, the subject is a human. In some embodiments, the subject has multiple myeloma, synovial sarcoma, esophageal cancer, head and neck cancer, lung cancer, bladder cancer, ovarian cancer, uterine cancer, stomach cancer, cervical cancer, breast cancer, or melanoma. In some embodiments, the subject has multiple myeloma.

In an aspect, the present disclosure provides a method of engineering a population of cells to express a chimeric antigen receptor, comprising: (a) introducing into a population of immune cells nucleic acid molecules encoding a chimeric antigen receptor as described herein; (b) culturing said population of immune cells under conditions to express said nucleic acid molecules; and (c) isolating said immune cells expressing said chimeric antigen receptor at the cells' surface. In some embodiments, the method further comprises obtaining said population of immune cells from a subject prior to introducing said nucleic acid molecule.

In an aspect, the present disclosure provides a method of treating a MAGE-A4-expressing cancer in a subject, comprising: (a) engineering a population of cells as described herein; and (b) reintroducing said population of cells expressing said chimeric antigen receptor into said subject. In some embodiments, said MAGE-A4-expressing cancer is multiple myeloma.

In an aspect, the present disclosure provides an isolated antigen-binding protein that competes for binding with a MAGE-A4-specific CAR as described herein. In some embodiments, the isolated antigen-binding protein is a CAR. In an aspect, the present disclosure provides an isolated antigen-binding protein that binds to the same epitope as a MAGE-A4-specific CAR as described herein. In some embodiments, said isolated antigen-binding protein is a CAR.

In an aspect, the present disclosure provides an isolated recombinant antibody or antigen-binding fragment thereof that specifically binds to a Melanoma-Associated Antigen A4 (MAGE-A4) polypeptide, wherein the antibody has one or more of the following characteristics: (a) binds to the MAGE-A4 polypeptide with an EC50 of less than about $10^{-9}$ M; (b) demonstrates an increase in survival in an animal with cancer after administration to said animal, as compared to a comparable animal without said administration; and/or (c) comprises (i) three heavy chain complementarity determining regions (CDRs) (HCDR1, HCDR2, and HCDR3) contained within a heavy chain variable region (HCVR) comprising an amino acid sequence having at least about 90% sequence identity to an HCVR set forth in Table 1; and (ii) three light chain CDRs (LCDR1, LCDR2, and LCDR3) contained within a light chain variable region (LCVR) comprising the amino acid sequence having at least about 90% sequence identity to an LCVR set forth in Table 1. In some embodiments, the MAGE-A4 polypeptide is an HLA-A2 bound MAGE-A4 polypeptide.

In some embodiments, the isolated antibody or antigen-binding fragment thereof comprises an HCVR having an amino acid sequence of SEQ ID NO: 2. In some embodiments, the isolated antibody or antigen-binding fragment thereof comprises an LCVR having an amino acid sequence of SEQ ID NO: 10. In some cases, the isolated antibody or antigen-binding fragment thereof comprises an HCVR/LCVR amino acid sequence pair of SEQ ID NOs: 2/10. In some embodiments, the isolated antibody or antigen-binding fragment thereof comprises an LCVR having an amino acid sequence of SEQ ID NO: 37. In some embodiments, the isolated antibody or antigen-binding fragment thereof comprises an HCVR having an amino acid sequence of SEQ ID NO: 51. In some cases, the isolated antibody or antigen-binding fragment thereof comprises an HCVR/LCVR amino acid sequence pair of SEQ ID NOs: 2/37.

In an aspect, the present disclosure provides an isolated antibody or antigen-binding fragment thereof, comprising: (a) an HCDR1 domain having an amino acid sequence of SEQ ID NO: 4; (b) an HCDR2 domain having an amino acid sequence of SEQ ID NO: 6; (c) an HCDR3 domain having an amino acid sequence of SEQ ID NO: 8; (d) an LCDR1 domain having an amino acid sequence of SEQ ID NO: 12; (e) an LCDR2 domain having an amino acid 14; and (f) an LCDR3 domain having an amino acid sequence of SEQ ID NO: 16.

In some embodiments, the isolated antibody or antigen-binding fragment thereof comprises an LCVR having an amino acid sequence of SEQ ID NO: 59.

In an aspect, the present disclosure provides an isolated antibody or antigen-binding fragment thereof, comprising: (a) an HCDR1 domain having an amino acid sequence of SEQ ID NO: 53; (b) an HCDR2 domain having an amino acid sequence of SEQ ID NO: 55; (c) an HCDR3 domain having an amino acid sequence of SEQ ID NO: 57; (d) an LCDR1 domain having an amino acid sequence of SEQ ID NO: 61; (e) an LCDR2 domain having an amino acid sequence of SEQ ID NO: 63; and (f) an LCDR3 domain having an amino acid sequence of SEQ ID NO: 65.

In some embodiments, the isolated antibody or antigen-binding fragment thereof comprises an HCVR/LCVR amino acid sequence pair of SEQ ID NOs: 51/59.

In some embodiments, the isolated antibody or antigen-binding fragment thereof is an IgG1 antibody. In some embodiments, isolated antibody or antigen-binding fragment thereof is an IgG4 antibody. In some embodiments, the isolated antibody or antigen-binding fragment thereof is a bispecific antibody.

In an aspect, the present disclosure provides a pharmaceutical composition comprising an isolated antibody or antigen-binding fragment thereof, as discussed above or herein, and a pharmaceutically acceptable carrier or diluent. In some embodiments, the pharmaceutical composition further comprises a second therapeutic agent. In some cases, the second therapeutic agent is selected from the group consisting of: an anti-tumor agent, steroids, and targeted therapies.

In an aspect, the present disclosure provides a polynucleotide molecule comprising a polynucleotide sequence that encodes an HCVR or an LCVR of an antibody as discussed above or herein.

In an aspect, the present disclosure provides a vector comprising the polynucleotide discussed above.

In an aspect, the present disclosure provides a cell comprising the vector discussed above.

In an aspect, the present disclosure provides a method of treating a MAGE-A4 expressing cancer, wherein the method comprises administering an antibody or antigen-binding fragment, or the pharmaceutical composition, as discussed above or herein, to a subject. In some embodiments, the pharmaceutical composition is administered in combination with a second therapeutic agent. In some cases, the second therapeutic agent is selected from the group consisting of: an anti-tumor agent, steroids, and targeted therapies. Uses of the antibodies, antigen-binding fragments thereof, and pharmaceutical compositions to treat MAGE-A4 expressing cancers, or in the manufacture of a medicament for treating MAGE-A4 expressing cancers, are also contemplated within the scope of the present disclosure.

Other embodiments will become apparent from a review of the ensuing detailed description.

BRIEF DESCRIPTION OF THE DRAWINGS

FIG. 2A depicts in vitro cytotoxicity data showing that HLA-A2/MAGE-A4$_{286-294}$-targeted CAR T cells exhibit enhanced cytotoxicity against A375 human melanoma tumor cells (open black circles, dashed line) and A375 cells overexpressing HLA-A2/MAGE-A4$_{286-294}$ (closed black circles, solid line, denoted as A375++), as compared control CAR T cells against A375 cells (A375 and A375++ can be seen as the top two curves depicted). FIG. 2B depicts in vitro cytotoxicity data showing that HLA-A2/MAGE-A4$_{286-294}$-targeted CAR T cells exhibit enhanced cytotoxicity against IM9 multiple myeloma cells (open black circles, dashed line) and IM9 cells overexpressing HLA-A2/MAGE-A4$_{286-294}$ target cells (closed black circles, solid line, denoted as IM9++), as compared control CAR T cells against A375 cells (IM9 and IM9++ can be seen as the top two curves depicted).

FIG. 3A depicts tumor volume over time in mice with an HLA-A2$^+$MAGE-A4$^+$ A375 human melanoma tumor cell xenograft, treated with control CAR T cells (anti-HLA-A2/HPV16E7(11-19) CAR T cells). Of the five mice tested, none were tumor-free at the end of the study (animals euthanized at day 42). FIG. 3B depicts tumor volume over time in mice with an HLA-A2$^+$MAGE-A4$^+$ A375 human melanoma tumor cell xenograft, treated with anti-HLA-A2/MAGE-A4$_{286-294}$ CAR T cells. All five mice tested were tumor-free at the end of the study (day 55).

FIG. 4A depicts tumor volume over time in mice with an HLA-A2$^+$MAGE-A4$^+$ IM9 human multiple myeloma tumor cell xenograft, treated with control CAR T cells (anti-HLA-A2/HPV16E7(11-19) CART cells). Of the five mice tested, none were tumor-free at the end of the study (animals euthanized at day 29). FIG. 4B depicts tumor volume over time in mice with an HLA-A2$^+$MAGE-A4$^+$ IM9 human multiple myeloma tumor cell xenograft, treated with anti-HLA-A2/MAGE-A4$_{286-294}$ CAR T cells. Of the five mice tested, three were tumor-free at the end of the study (day 52).

DETAILED DESCRIPTION

Figure 1:
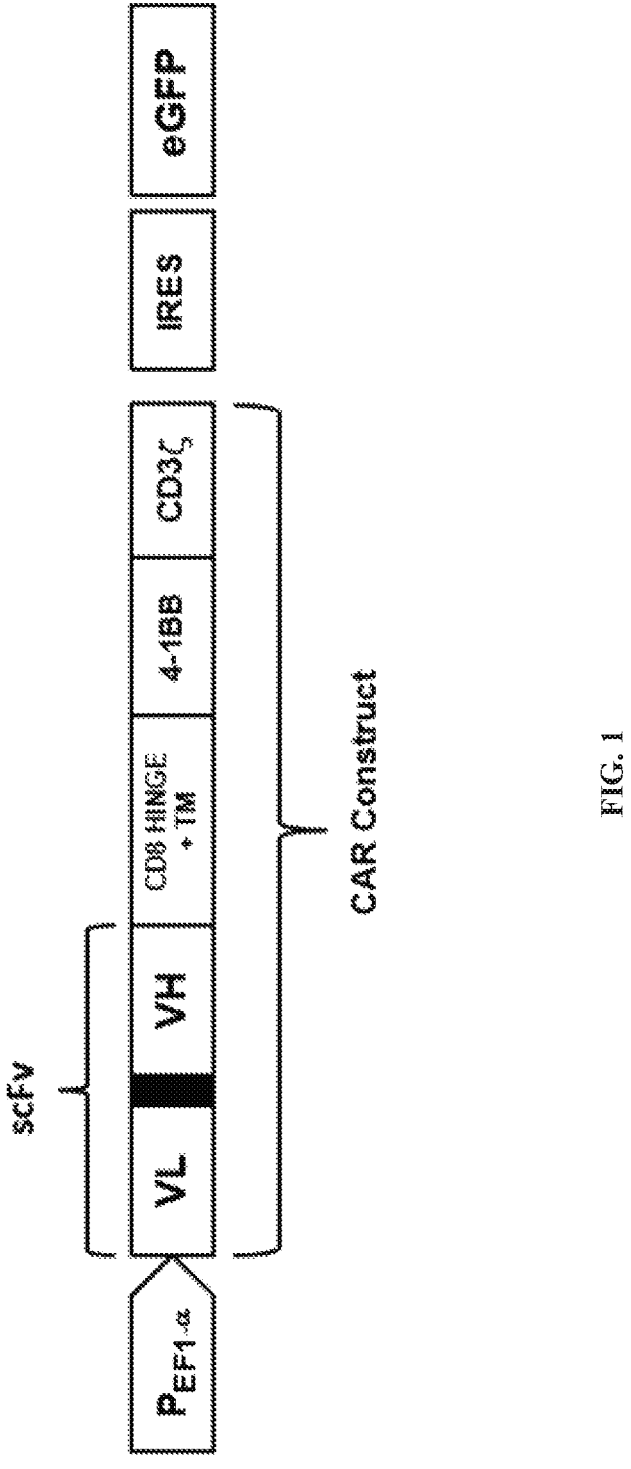
FIG. 1 illustrates an exemplary nucleotide construct for expressing a chimeric antigen receptor (CAR) construct. The exemplary nucleotide construct comprises an anti-MAGE-A4 VL-linker-VH scFv, a human CD8 hinge and transmembrane domain, a 4-1BB co-stimulatory domain, a CD3zeta signaling domain, and an IRES:eGFP sequence for tracking CAR-transduced cells.

It is to be understood that the inventions described herein are not limited to particular methods and experimental conditions described, as such methods and conditions may vary. It is also to be understood that the terminology used herein is for the purpose of describing particular embodiments only, and is not intended to be limiting, since the scope of the present inventions will be limited only by the appended claims. Any embodiments or features of embodiments can be combined with one another, and such combinations are expressly encompassed within the scope of the present invention. Any specific value discussed above or herein may be combined with another related value discussed above or herein to recite a range with the values representing the upper and lower ends of the range, and such ranges are encompassed within the scope of the present disclosure.

Unless defined otherwise, all technical and scientific terms used herein have the same meaning as commonly understood by one of ordinary skill in the art to which the inventions belong. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present inventions, the preferred methods and materials are now described. All patents, applications and non-patent publications mentioned in this specification are incorporated herein by reference in their entireties.

Definitions

The term "MAGE-A4," as used herein, refers to Melanoma-Associated Antigen A4. MAGE-A4 is an intracellular protein expressed by a variety of different tumor cells. As used herein, "MAGE-A4" refers to the human MAGE-A4 protein unless specified as being from a non-human species (e.g., "mouse MAGE-A4," "monkey MAGE-A4," etc.). The human MAGE-A4 protein has the amino acid sequence shown in SEQ ID NO: 32 and the polynucleic acid sequence of SEQ ID NO: 31. Reference to particular regions of a MAGE-A4 polypeptide (e.g., MAGE-A4 286-294 or MAGE-A4 230-239) are with respect to SEQ ID NO: 32. As used herein, the terms "MAGE-A4 286-294," "MAGE-A4 (286-294)," and "MAGEA4$_{286-294}$" may be used interchangeably. Likewise, the terms "MAGE-A4 230-239," "MAGE-A4 (230-239)," and "MAGEA4$_{230-239}$" may be used interchangeably. The polypeptide sequence of MAGE-A4 (286-294) (KVLEHVVRV) is given as SEQ ID NO: 33. The polypeptide sequence of MAGE-A4 (230-239) (GVYDGREHTV) is given as SEQ ID NO: 49.

As used herein, "an antibody that binds MAGE-A4" or an "anti-MAGE-A4 antibody" includes antibodies and antigen-binding fragments thereof that specifically recognize MAGE-A4. In some embodiments, an antibody that binds MAGE-A4 interacts with amino acids 286-294 of MAGE-A4 or amino acids 230-239 of MAGE-A4.

The terms "ligand-binding domain" and "antigen-binding domain" are used interchangeably herein, and refer to that portion of a chimeric antigen receptor or a corresponding antibody that binds specifically to a predetermined antigen (e.g., MAGE-A4). References to a "corresponding antibody" refer to the antibody from which the CDRs or variable regions (heavy chain variable region (abbreviated HCVR or VH) and light chain variable region (abbreviated LCVR or VL)) used in a chimeric antigen receptor are derived. For example, chimeric antigen receptor constructs discussed in the Examples include scFvs with variable regions derived from an anti-MAGE-A4 antibody. This anti-MAGE-A4 antibody is the "corresponding antibody" to the respective chimeric antigen receptor.

The term "antibody", as used herein, means any antigen-binding molecule or molecular complex comprising at least one complementarity determining region (CDR) that specifically binds to or interacts with a particular antigen (e.g., MAGE-A4). In some embodiments, an antibody can bind to or interact with an MHC-bound polypeptide, such as an HLA-bound polypeptide. In the context of the present disclosure, an antibody can, in some embodiments, bind to an HLA-A2-bound polypeptide such as a MAGE-A4 polypeptide (e.g., MAGE-A4 286-294 or 230-239) presented by HLA-A2. The term "antibody" includes immunoglobulin molecules comprising four polypeptide chains, two heavy (H) chains and two light (L) chains inter-connected by disulfide bonds, as well as multimers thereof (e.g., IgM). The term "antibody" also includes immunoglobulin molecules consisting of four polypeptide chains, two heavy (H) chains and two light (L) chains inter-connected by disulfide bonds. Each heavy chain (abbreviated herein as HC) comprises a heavy chain variable region (abbreviated herein as HCVR or V$_H$) and a heavy chain constant region. The heavy chain constant region comprises three domains, C$_H$1, C$_H$2 and C$_H$3. Each light chain (abbreviated herein as LC) comprises a light chain variable region (abbreviated herein as LCVR or V$_L$) and a light chain constant region. The light chain constant region comprises one domain (C$_L$1). The V$_H$ and V$_L$ regions can be further subdivided into regions of hypervariability, termed complementarity determining regions (CDRs), interspersed with regions that are more conserved, termed framework regions (FR). Each V$_H$ and V$_L$ is composed of three CDRs and four FRs, arranged from amino-terminus to carboxy-terminus in the following order: FR1, CDR1, FR2, CDR2, FR3, CDR3, FR4. In different embodiments of the present disclosure, the FRs of the anti-MAGE-A4 antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a V$_H$ domain associated with a V$_L$ domain, the V$_H$ and V$_L$ domains may be situated relative to one another in any suitable arrangement. For example, the variable region may be dimeric and contain V$_H$-V$_H$, V$_H$-V$_L$ or V$_L$-V$_L$ dimers. Alternatively, the antigen-binding fragment of an antibody may contain a monomeric V$_H$ or V$_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$- $C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present disclosure may comprise a homo-dimer or heterodimer (or other multimer) of any of the variable and constant domain configurations listed above in non-covalent association with one another and/or with one or more monomeric $V_H$ or $V_L$ domain (e.g., by disulfide bond(s)).

In certain embodiments, the anti-MAGE-A4 antibodies from which antigen-binding fragments are derived are human antibodies. The term "human antibody", as used herein, is intended to include antibodies having variable and constant regions derived from human germline immunoglobulin sequences. The human antibodies of the present disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies used to generate anti-MAGE-A4 antigen-binding fragments may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The present disclosure encompasses antibodies having one or more mutations in the hinge, $C_H$2 or $C_H$3 region which may be desirable, for example, in production, to improve the yield of the desired antibody form.

Antibodies may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present disclosure. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The anti-MAGE-A4 antibodies, or antigen binding fragments thereof, disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

The anti-MAGE-A4 antibodies may comprise variants of any of the HCVR, LCVR, and/or CDR amino acid sequences disclosed herein having one or more conservative substitutions. For example, the anti-MAGE-A4 antibodies may have HCVR, LCVR, and/or CDR amino acid sequences with, e.g., 10 or fewer, 9 or fewer, 8 or fewer, 7 or fewer, 6 or fewer, 5 or fewer, 4 or fewer, 3 or fewer, 2 or fewer, or 1 conservative amino acid substitutions relative to any of the HCVR, LCVR, and/or CDR amino acid sequences set forth herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule. In some embodiments, the present disclosure provides a polypeptide comprising a sequence that is at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.9%, or 100% identical to the sequence of SEQ ID NO: 22 or SEQ ID NO: 39, or to a portion of SEQ ID NO: 22 or SEQ ID NO: 39 (e.g., an HCVR such as the sequence of SEQ ID NO: 2 or an LCVR such as the sequence of SEQ ID NO: 10 or SEQ ID NO: 37, or a framework region of a polypeptide sequence such as those found in SEQ ID NOs: 2, 10, 22, 37, or 39). In some embodiments, the present disclosure provides a polynucleic acid encoding such a polypeptide. In some embodiments, the present disclosure provides a polynucleic acid comprising a sequence that is at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.9%, or 100% identical to the sequence of SEQ ID NO: 21 or SEQ ID NO: 38, or to a portion of SEQ ID NO: 21 or SEQ ID NO: 38 (e.g., an HCVR such as the sequence of SEQ ID NO: 1 or an LCVR such as the sequence of SEQ ID NO: 9 or SEQ ID NO: 36, or a framework region of a polynucleotide sequence such as SEQ ID NOs: 1, 9, 21, 36, or 38).

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Sequences also can be compared using the Smith-Waterman homology search algorithm using an affine gap search with a gap open penalty of 12 and a gap extension penalty of 2, BLOSUM matrix of 62. Another preferred algorithm when comparing a sequence of the present disclosure to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

As used herein, the terms "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

The term "chimeric antigen receptor" (CAR) refers to molecules that combine a binding domain against a component present on the target cell, for example an antibody-based specificity for a desired antigen (e.g., a tumor antigen, such as MAGE-A4) with a T cell receptor-activating intracellular domain to generate a chimeric protein that exhibits a specific anti-target cellular immune activity. Generally, CARs consist of an extracellular single chain antibody-binding domain (scFv) fused to the intracellular signaling domain of the T cell antigen receptor complex zeta chain, and have the ability, when expressed in T cells, to redirect antigen recognition based on the monoclonal antibody's specificity.

The term "HLA" refers to the human leukocyte antigen (HLA) system or complex, which is a gene complex encoding the major histocompatibility complex (MHC) proteins in humans. These cell-surface proteins are responsible for the regulation of the immune system in humans. HLAs corresponding to MHC class I (A, B, and C) present peptides from inside the cell.

The term "HLA-A" refers to the group of human leukocyte antigens (HLA) that are coded for by the HLA-A locus.

HLA-A is one of three major types of human MHC class I cell surface receptors. The receptor is a heterodimer, and is composed of a heavy α chain and smaller β chain. The α chain is encoded by a variant HLA-A gene, and the β chain (β2-microglobulin) is an invariant β2 microglobulin molecule.

The term "HLA-A2" is one particular class I major histocompatibility complex (MHC) allele group at the HLA-A locus; the α chain is encoded by the HLA-A*02 gene and the β chain is encoded by the β2-microglobulin or B2M locus.

The term "vector," as used herein, includes, but is not limited to, a viral vector, a plasmid, an RNA vector or a linear or circular DNA or RNA molecule which may consists of chromosomal, non-chromosomal, semi-synthetic or synthetic nucleic acids. In some cases, the vectors are those capable of autonomous replication (episomal vector) and/or expression of nucleic acids to which they are linked (expression vectors). Large numbers of suitable vectors are known to those of skill in the art and are commercially available. Viral vectors include retrovirus, adenovirus, parvovirus (e.g., adenoassociated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, and lentivirus.

A "costimulatory domain" or "costimulatory molecule" refers to the cognate binding partner on a T-cell that specifically binds with a costimulatory ligand, thereby mediating a costimulatory response by the cell, such as, but not limited to proliferation. Costimulatory molecules include, but are not limited to, an MHC class I molecule, BTLA and Toll ligand receptor. Examples of costimulatory molecules include CD27, CD28, CD8, 4-1BB (CD137) (SEQ ID NO: 29), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like. A costimulatory molecule is a cell surface molecule other than an antigen receptor or their ligands that is required for an efficient immune response.

A "costimulatory ligand" refers to a molecule on an antigen presenting cell that specifically binds a cognate costimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A costimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3.

A "costimulatory signal" refers to a signal, which in combination with a primary signal, such as TCR/CD3 ligation, leads to T cell proliferation and/or upregulation or downregulation of key molecules.

The term "extracellular ligand-binding domain," as used herein, refers to an oligo- or polypeptide that is capable of binding a ligand, e.g., a cell surface molecule. For example, the extracellular ligand-binding domain may be chosen to recognize a ligand that acts as a cell surface marker on target cells associated with a particular disease state (e.g., cancer). Examples of cell surface markers that may act as ligands include those associated with viral, bacterial and parasitic infections, autoimmune disease and cancer cells. An extracellular ligand-binding domain can comprise LCVR and HCVR regions (e.g., formatted as an scFv), optionally joined by a linker.

The term "subject" or "patient" as used herein includes all members of the animal kingdom including non-human primates and humans. In one embodiment, patients are humans with a cancer (e.g., multiple myeloma or melanoma).

A "signal transducing domain" or "signaling domain" of a CAR, as used herein, is responsible for intracellular signaling following the binding of an extracellular ligand binding domain to the target resulting in the activation of the immune cell and immune response. In other words, the signal transducing domain is responsible for the activation of at least one of the normal effector functions of the immune cell in which the CAR is expressed. For example, the effector function of a T cell can be a cytolytic activity or helper activity including the secretion of cytokines. Thus, the term "signal transducing domain" refers to the portion of a protein which transduces the effector function signal and directs the cell to perform a specialized function. Examples of signal transducing domains for use in a CAR can be the cytoplasmic sequences of the T cell receptor and co-receptors that act in concert to initiate signal transduction following antigen receptor engagement, as well as any derivate or variant of these sequences and any synthetic sequence that has the same functional capability. In some cases, signaling domains comprise two distinct classes of cytoplasmic signaling sequences, those that initiate antigen-dependent primary activation, and those that act in an antigen-independent manner to provide a secondary or co-stimulatory signal. Primary cytoplasmic signaling sequences can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Exemplary ITAMs include those derived from TCRzeta, FcRgamma, FcRbeta, FcRepsilon, CD3gamma, CD3delta, CD3epsilon, CD5, CD22, CD79a, CD79b and CD66d. In some embodiments, the signal transducing domain of the CAR can comprise the CD3zeta signaling domain (SEQ ID NO: 30).

Chimeric Antigen Receptors (CARs)

Chimeric antigen receptors (CARs) can redirect T cell specificity toward antibody-recognized antigens on the surface of cells (e.g., cancer cells), whether those antigens are expressed on the cell surface or expressed intracellularly and presented by, for example, an HLA.

One aspect of the present disclosure includes a chimeric antigen receptor (CAR) which is specific for a MAGE-A4 antigen presented on the surface of cells such as tumor cells. This presentation can be by, for example, an HLA such as HLA-A2. In one embodiment of the present disclosure, a CAR as described herein comprises an extracellular target-specific binding domain, a transmembrane domain, an intracellular signaling domain (such as a signaling domain derived from CD3zeta or FcRgamma), and/or one or more co-stimulatory signaling domains derived from a co-stimulatory molecule, such as, but not limited to, 4-1BB. In one embodiment, the CAR includes a hinge or spacer region between the extracellular binding domain and the transmembrane domain, such as a CD8alpha hinge.

The binding domain or the extracellular domain of the CAR provides the CAR with the ability to bind to the target antigen of interest. A binding domain (e.g., a ligand-binding domain or antigen-binding domain) can be any protein, polypeptide, oligopeptide, or peptide that possesses the ability to specifically recognize and bind to a biological molecule (e.g., a cell surface receptor or tumor protein, or a component thereof). A binding domain includes any naturally occurring, synthetic, semi-synthetic, or recombinantly produced binding partner for a biological molecule of interest. For example, and as further described herein, a binding domain may be antibody light chain and heavy chain variable regions, or the light and heavy chain variable regions can be joined together in a single chain and in either orientation (e.g., VL-VH or VH-VL). A variety of assays are known for identifying binding domains of the present disclosure that specifically bind with a particular target, including Western blot, ELISA, flow cytometry, or surface plasmon resonance analysis (e.g., using BIACORE analysis). The target may be an antigen of clinical interest against which it would be desirable to trigger an effector immune response that results in tumor killing. In one embodiment, the target antigen of the binding domain of the chimeric antigen receptor is a MAGE-A4 protein on the surface of tumor cells (e.g., an HLA-presented MAGE-A4 protein such as an HLA-A2-presented MAGE-A4 protein).

Illustrative ligand-binding domains include antigen binding proteins, such as antigen binding fragments of an antibody, such as scFv, scTCR, extracellular domains of receptors, ligands for cell surface molecules/receptors, or receptor binding domains thereof, and tumor binding proteins. In certain embodiments, the antigen binding domains included in a CAR of the present disclosure can be a variable region (Fv), a CDR, a Fab, an scFv, a VH, a VL, a domain antibody variant (dAb), a camelid antibody (VHH), a fibronectin 3 domain variant, an ankyrin repeat variant and other antigen-specific binding domain derived from other protein scaffolds.

In one embodiment, the binding domain of the CAR is an anti-MAGE-A4 single chain antibody (scFv), and may be a murine, human or humanized scFv. Single chain antibodies may be cloned from the V region genes of a hybridoma specific for a desired target. A technique which can be used for cloning the variable region heavy chain (VH) and variable region light chain (VL) has been described, for example, in Orlandi et al., *PNAS,* 1989; 86: 3833-3837. Thus, in certain embodiments, a binding domain comprises an antibody-derived binding domain but can be a non-antibody derived binding domain. An antibody-derived binding domain can be a fragment of an antibody or a genetically engineered product of one or more fragments of the antibody, which fragment is involved in binding with the antigen.

In certain embodiments, the CARs of the present disclosure may comprise a linker between the various domains, added for appropriate spacing and conformation of the molecule. For example, in one embodiment, there may be a linker between the binding domain VH or VL which may be between 1 and 20 amino acids long. In other embodiments, the linker between any of the domains of the chimeric antigen receptor may be between 1 and 15 or 15 amino acids long. In this regard, the linker may be 1, 2, 3, 4, 5, 6, 7, 8, 9, 10, 11, 12, 13, 14, 15, 16, 17, 18, 19 or 20 amino acids long. In further embodiments, the linker may be 21, 22, 23, 24, 25, 26, 27, 28, 29 or 30 amino acids long. Ranges including the numbers described herein are also included herein, e.g., a linker 10-30 amino acids long.

In certain embodiments, linkers suitable for use in the CAR described herein are flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers (G)n, glycine-serine polymers, where n is an integer of at least one, glycine-alanine polymers, alanine-serine polymers, and other flexible linkers known in the art. Glycine and glycine-serine polymers are relatively unstructured, and therefore may be able to serve as a neutral tether between domains of fusion proteins such as the CARs described herein. Glycine accesses significantly more phi-psi space than even alanine, and is much less restricted than residues with longer side chains (see Scheraga, *Rev. Computational Chem.* 11173-142 (1992)). The ordinarily skilled artisan will recognize that design of a CAR can include linkers that are all or partially flexible, such that the linker can include a flexible linker as well as one or more portions that confer less flexible structure to provide for a desired CAR structure. Specific linkers include $(G4S)_n$ linkers, wherein n=1-3, as shown in SEQ ID NOs: 23-25. Another exemplary linker is provided as SEQ ID NO: 26. A linker can be present between the LCVR and HCVR regions of a CAR, between a variable region (such as an HCVR) and a hinge region (such as a CD8α hinge), or both. For example, the present disclosure provides a CAR comprising a (G4S)3 linker between an LCVR and an HCVR, and a (G4S)1 linker between an HCVR and a CD8α hinge.

The binding domain of the CAR may be followed by a "spacer," or, "hinge," which refers to the region that moves the antigen binding domain away from the effector cell surface to enable proper cell/cell contact, antigen binding and activation (Patel et al., *Gene Therapy,* 1999; 6: 412-419). The hinge region in a CAR is generally between the transmembrane (TM) and the binding domain. In certain embodiments, a hinge region is an immunoglobulin hinge region and may be a wild type immunoglobulin hinge region or an altered wild type immunoglobulin hinge region. Other exemplary hinge regions used in the CARs described herein include the hinge region derived from the extracellular regions of type 1 membrane proteins such as CD8alpha, CD4, CD28 and CD7, which may be wild-type hinge regions from these molecules or may be altered. In one embodiment, the hinge region comprises a CD8alpha hinge (SEQ ID NO: 27).

The "transmembrane" region or domain is the portion of the CAR that anchors the extracellular binding portion to the plasma membrane of the immune effector cell, and facilitates binding of the binding domain to the target antigen. The transmembrane domain may be a CD3zeta transmembrane domain, however other transmembrane domains that may be employed include those obtained from CD8alpha, CD4, CD28, CD45, CD9, CD16, CD22, CD33, CD64, CD80, CD86, CD134, CD137, and CD154. In one embodiment, the transmembrane domain is the transmembrane domain of CD137. In some embodiments, the transmembrane domain comprises the amino acid sequence of SEQ ID NO: 28. In certain embodiments, the transmembrane domain is synthetic in which case it would comprise predominantly hydrophobic residues such as leucine and valine.

The "intracellular signaling domain" or "signaling domain" refers to the part of the chimeric antigen receptor protein that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. The term "effector function" refers to a specialized function of the cell. Effector function of the T cell, for example, may be cytolytic activity or help or activity including the secretion of a cytokine. Thus, the terms "intracellular signaling domain" or "signaling domain," used interchangeably herein, refer to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal. The intracellular signaling domain is also known as the, "signal transduction domain," and is typically derived from portions of the human CD3 or FcRy chains.

It is known that signals generated through the T cell receptor alone are insufficient for full activation of the T cell and that a secondary, or costimulatory signal is also required. Thus, T cell activation can be said to be mediated by two distinct classes of cytoplasmic signaling sequences: those that initiate antigen dependent primary activation through the T cell receptor (primary cytoplasmic signaling sequences) and those that act in an antigen independent manner to provide a secondary or costimulatory signal (secondary cytoplasmic signaling sequences). Cytoplasmic signaling sequences that act in a costimulatory manner may contain signaling motifs which are known as immunoreceptor tyrosine-based activation motif or ITAMs.

Examples of ITAM containing primary cytoplasmic signaling sequences that are of particular use in the present disclosure include those derived from TCRzeta, FcRgamma, FcRbeta, CD3gamma, CD3delta, CD3epsilon, CD5, CD22, CD79a, CD79b and CD66d. In one particular embodiment, the intracellular signaling domain of the anti-MAGE-A4 CARs described herein are derived from CD3zeta. In some embodiments, the signaling domain comprises the amino acid sequence of SEQ ID NO: 30.

As used herein, the term, "costimulatory signaling domain," or "costimulatory domain", refers to the portion of the CAR comprising the intracellular domain of a costimulatory molecule. Costimulatory molecules are cell surface molecules other than antigen receptors or Fc receptors that provide a second signal required for efficient activation and function of T lymphocytes upon binding to antigen. Examples of such co-stimulatory molecules include CD27, CD28, 4-1BB (CD137), OX40 (CD134), CD30, CD40, PD-1, ICOS (CD278), LFA-1, CD2, CD7, LIGHT, NKD2C, B7-H2 and a ligand that specifically binds CD83. Accordingly, while the present disclosure provides exemplary costimulatory domains derived from CD3zeta and 4-1BB, other costimulatory domains are contemplated for use with the CARs described herein. The inclusion of one or more co-stimulatory signaling domains may enhance the efficacy and expansion of T cells expressing CAR receptors. The intracellular signaling and costimulatory signaling domains may be linked in any order in tandem to the carboxyl terminus of the transmembrane domain. In some embodiments, the costimulatory domain comprises the amino acid sequence of SEQ ID NO: 29.

Although scFv-based CARs engineered to contain a signaling domain from CD3 or FcRgamma have been shown to deliver a potent signal for T cell activation and effector function, they are not sufficient to elicit signals that promote T cell survival and expansion in the absence of a concomitant costimulatory signal. Other CARs containing a binding domain, a hinge, a transmembrane and the signaling domain derived from CD3zeta or FcRgamma together with one or more costimulatory signaling domains (e.g., intracellular costimulatory domains derived from CD28, CD137, CD134 and CD278) may more effectively direct antitumor activity as well as increased cytokine secretion, lytic activity, survival and proliferation in CAR expressing T cells in vitro, and in animal models and cancer patients (Milone et al., *Molecular Therapy,* 2009; 17: 1453-1464; Zhong et al., *Molecular Therapy,* 2010; 18: 413-420; Carpenito et al., *PNAS,* 2009; 106:3360-3365).

In various embodiments, the anti-MAGE-A4 CARs of the present disclosure comprise (a) an anti-MAGE-A4 scFv as a binding domain (e.g., an scFv having binding regions (e.g., CDRs or variable domains) from the anti-MAGE-A4 antibody identified in Table 1) (b) a hinge region derived from human CD8alpha, (c) a human CD8alpha transmembrane domain, and (d) a human T cell receptor CD3 zeta chain (CD3) intracellular signaling domain, and optionally one or more costimulatory signaling domains, e.g., 4-1BB. In one embodiment, the different protein domains are arranged from amino to carboxyl terminus in the following order: binding domain, hinge region and transmembrane domain. The intracellular signaling domain and optional co-stimulatory signaling domains are linked to the transmembrane carboxy terminus in any order in tandem to form a single chain chimeric polypeptide. In one embodiment, a nucleic acid construct encoding an anti-MAGE-A4 CAR is a chimeric nucleic acid molecule comprising a nucleic acid molecule comprising different coding sequences, for example, (5' to 3') the coding sequences of a human anti-MAGE-A4 scFv, a human CD8alpha-hinge, a human CD8alpha transmembrane domain and a CD3zeta intracellular signaling domain. In another embodiment, a nucleic acid construct encoding an anti-MAGE-A4 CAR is a chimeric nucleic acid molecule comprising a nucleic acid molecule comprising different coding sequences, for example, (5' to 3') the coding sequences of a human anti-MAGE-A4 scFv, a human CD8alpha-hinge, a human CD8alpha transmembrane domain, a 4-1BB co-stimulatory domain, and a CD3zeta co-stimulatory domain.

In certain embodiments, the polynucleotide encoding the CAR described herein is inserted into a vector. The vector is a vehicle into which a polynucleotide encoding a protein may be covalently inserted so as to bring about the expression of that protein and/or the cloning of the polynucleotide. Such vectors may also be referred to as "expression vectors". The isolated polynucleotide may be inserted into a vector using any suitable methods known in the art, for example, without limitation, the vector may be digested using appropriate restriction enzymes and then may be ligated with the isolated polynucleotide having matching restriction ends. Expression vectors can have the ability to incorporate and express heterologous or modified nucleic acid sequences coding for at least part of a gene product capable of being transcribed in a cell. In most cases, RNA molecules are then translated into a protein. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are discussed infra. An expression vector may comprise additional elements, for example, the expression vector may have two replication systems, thus allowing it to be maintained in two organisms, for example in human cells for expression and in a prokaryotic host for cloning and amplification.

The expression vector may have the necessary 5' upstream and 3' downstream regulatory elements such as promoter sequences such as CMV, PGK and EF1alpha. promoters, ribosome recognition and binding TATA box, and 3' UTR AAUAAA transcription termination sequence for the efficient gene transcription and translation in its respective host cell. Other suitable promoters include the constitutive promoter of simian virus 40 (SV40) early promoter, mouse mammary tumor virus (MMTV), HIV LTR promoter, MoMuLV promoter, avian leukemia virus promoter, EBV immediate early promoter, and rous sarcoma virus promoter. Human gene promoters may also be used, including, but not limited to the actin promoter, the myosin promoter, the hemoglobin promoter, and the creatine kinase promoter. In certain embodiments inducible promoters are also contemplated as part of the vectors expressing chimeric antigen receptor. This provides a molecular switch capable of turning on expression of the polynucleotide sequence of interest or turning off expression. Examples of inducible promoters include, but are not limited to a metallothionine promoter, a glucocorticoid promoter, a progesterone promoter, or a tetracycline promoter.

The expression vector may have additional sequence such as 6×-histidine, c-Myc, and FLAG tags which are incorporated into the expressed CARs. Thus, the expression vector may be engineered to contain 5' and 3' untranslated regulatory sequences that sometimes can function as enhancer sequences, promoter regions and/or terminator sequences that can facilitate or enhance efficient transcription of the nucleic acid(s) of interest carried on the expression vector. An expression vector may also be engineered for replication and/or expression functionality (e.g., transcription and translation) in a particular cell type, cell location, or tissue type. Expression vectors may include a selectable marker for maintenance of the vector in the host or recipient cell.

In various embodiments, the vectors are plasmid, autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40). Examples of expression vectors are LENTI-X™ Bicistronic Expression System (Neo) vectors (Clontrch), pClneo vectors (Promega) for expression in mammalian cells; pLenti4/V5-DEST™, pLenti6/V5-DEST™, and pLenti6.2N5-GW/lacZ (Invitrogen) for lentivirus-mediated gene transfer and expression in mammalian cells. The coding sequences of the CARs disclosed herein can be ligated into such expression vectors for the expression of the chimeric protein in mammalian cells.

In certain embodiments, the nucleic acids encoding the CAR of the present disclosure are provided in a viral vector. A viral vector can be that derived from retrovirus, lentivirus, or foamy virus. As used herein, the term, "viral vector," refers to a nucleic acid vector construct that includes at least one element of viral origin and has the capacity to be packaged into a viral vector particle. The viral vector can contain the coding sequence for the various chimeric proteins described herein in place of nonessential viral genes. The vector and/or particle can be utilized for the purpose of transferring DNA, RNA or other nucleic acids into cells either in vitro or in vivo. Numerous forms of viral vectors are known in the art.

In certain embodiments, the viral vector containing the coding sequence for a CAR described herein is a retroviral vector or a lentiviral vector. The term "retroviral vector" refers to a vector containing structural and functional genetic elements that are primarily derived from a retrovirus. The term "lentiviral vector" refers to a vector containing structural and functional genetic elements outside the LTRs that are primarily derived from a lentivirus.

The retroviral vectors for use herein can be derived from any known retrovirus (e.g., type c retroviruses, such as Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend, Murine Stem Cell Virus (MSCV) and Rous Sarcoma Virus (RSV)). Retroviruses" of the present disclosure also include human T cell leukemia viruses, HTLV-1 and HTLV-2, and the lentiviral family of retroviruses, such as Human Immunodeficiency Viruses, HIV-1, HIV-2, simian immunodeficiency virus (SIV), feline immunodeficiency virus (FIV), equine immunodeficiency virus (EIV), and other classes of retroviruses.

A lentiviral vector for use herein refers to a vector derived from a lentivirus, a group (or genus) of retroviruses that give rise to slowly developing disease. Viruses included within this group include HIV (human immunodeficiency virus; including HIV type 1, and HIV type 2); visna-maedi; a caprine arthritis-encephalitis virus; equine infectious anemia virus; feline immunodeficiency virus (Hy); bovine immune deficiency virus (BIV); and simian immunodeficiency virus (SIV). Preparation of the recombinant lentivirus can be achieved using the methods according to Dull et al. and Zufferey et al. (Dull et al., *J. Virol.,* 1998; 72: 8463-8471 and Zufferey et al., *J. Virol.* 1998; 72:9873-9880).

Retroviral vectors (i.e., both lentiviral and non-lentiviral) for use in the present disclosure can be formed using standard cloning techniques by combining the desired DNA sequences in the order and orientation described herein (Current Protocols in Molecular Biology, Ausubel, F. M. et al. (eds.) Greene Publishing Associates, (1989), Sections 9.10-9.14 and other standard laboratory manuals; Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Suitable sources for obtaining retroviral (i.e., both lentiviral and non-lentiviral) sequences for use in forming the vectors include, for example, genomic RNA and cDNAs available from commercially available sources, including the Type Culture Collection (ATCC), Rockville, Md. The sequences also can be synthesized chemically.

For expression of an anti-MAGE-A4 CAR, the vector may be introduced into a host cell to allow expression of the polypeptide within the host cell. The expression vectors may contain a variety of elements for controlling expression, including without limitation, promoter sequences, transcription initiation sequences, enhancer sequences, selectable markers, and signal sequences. These elements may be selected as appropriate by a person of ordinary skill in the art, as described herein. For example, the promoter sequences may be selected to promote the transcription of the polynucleotide in the vector. Suitable promoter sequences include, without limitation, T7 promoter, T3 promoter, SP6 promoter, beta-actin promoter, EF1a promoter, CMV promoter, and SV40 promoter. Enhancer sequences may be selected to enhance the transcription of the polynucleotide. Selectable markers may be selected to allow selection of the host cells inserted with the vector from those not, for example, the selectable markers may be genes that confer antibiotic resistance. Signal sequences may be selected to allow the expressed polypeptide to be transported outside of the host cell.

For cloning of the polynucleotide, the vector may be introduced into a host cell (an isolated host cell) to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art. For example, the origin of replication may be selected to promote autonomous replication of the vector in the host cell.

In certain embodiments, the present disclosure provides isolated host cells containing the vectors provided herein. The host cells containing the vector may be useful in expression or cloning of the polynucleotide contained in the vector. Suitable host cells can include, without limitation, prokaryotic cells, fungal cells, yeast cells, or higher eukaryotic cells such as mammalian cells. Suitable prokaryotic cells for this purpose include, without limitation, eubacteria, such as Gram-negative or Gram-positive organisms, for example, Enterobactehaceae such as *Escherichia*, e.g., *E. coli, Enterobacter, Erwinia, Klebsiella, Proteus, Salmonella,* e.g., *Salmonella typhimurium, Serratia,* e.g., *Serratia marcescans,* and *Shigella,* as well as Bacilli such as *B. subtilis* and *B. licheniformis, Pseudomonas* such as *P. aeruginosa,* and *Streptomyces.*

The CARs of the present disclosure are introduced into a host cell using transfection and/or transduction techniques known in the art. As used herein, the terms, "transfection," and, "transduction," refer to the processes by which an exogenous nucleic acid sequence is introduced into a host cell. The nucleic acid may be integrated into the host cell DNA or may be maintained extrachromosomally. The nucleic acid may be maintained transiently or may be a stable introduction. Transfection may be accomplished by a variety of means known in the art including but not limited to calcium phosphate-DNA co-precipitation, DEAE-dextran-mediated transfection, polybrene-mediated transfection, electroporation, microinjection, liposome fusion, lipofection, protoplast fusion, retroviral infection, and biolistics. Transduction refers to the delivery of a gene(s) using a viral or retroviral vector by means of viral infection rather than by transfection. In certain embodiments, retroviral vectors are transduced by packaging the vectors into virions prior to contact with a cell. For example, a nucleic acid encoding an anti-MAGE-A4 CAR carried by a retroviral vector can be transduced into a cell through infection and pro virus integration.

As used herein, the term "genetically engineered" or "genetically modified" refers to the addition of extra genetic material in the form of DNA or RNA into the total genetic material in a cell. The terms, "genetically modified cells," "modified cells," and, "redirected cells," are used interchangeably.

In particular, the CAR of the present disclosure is introduced and expressed in immune effector cells so as to redirect their specificity to a target antigen of interest, e.g., a malignant MAGE-A4-expressing cell, such as a malignant cell presenting MAGE-A4 with HLA-A2.

The present disclosure provides methods for making the immune effector cells which express the CAR as described herein. In one embodiment, the method comprises transfecting or transducing immune effector cells isolated from a subject, such as a subject having a MAGE-A4-expressing tumor cell, such that the immune effector cells express one or more CAR as described herein. In certain embodiments, the immune effector cells are isolated from an individual and genetically modified without further manipulation in vitro. Such cells can then be directly re-administered into the individual. In further embodiments, the immune effector cells are first activated and stimulated to proliferate in vitro prior to being genetically modified to express a CAR. In this regard, the immune effector cells may be cultured before or after being genetically modified (i.e., transduced or transfected to express a CAR as described herein).

Prior to in vitro manipulation or genetic modification of the immune effector cells described herein, the source of cells may be obtained from a subject. In particular, the immune effector cells for use with the CARs as described herein comprise T cells. T cells can be obtained from a number of sources, including peripheral blood mononuclear cells, bone marrow, lymph nodes tissue, cord blood, thymus issue, tissue from a site of infection, ascites, pleural effusion, spleen tissue, and tumors. In certain embodiments, T cell can be obtained from a unit of blood collected from the subject using any number of techniques known to the skilled person, such as FICOLL separation. In one embodiment, cells from the circulating blood of an individual are obtained by apheresis. The apheresis product typically contains lymphocytes, including T cells, monocytes, granulocyte, B cells, other nucleated white blood cells, red blood cells, and platelets. In one embodiment, the cells collected by apheresis may be washed to remove the plasma fraction and to place the cells in an appropriate buffer or media for subsequent processing. In one embodiment of the present disclosure, the cells are washed with PBS. In an alternative embodiment, the washed solution lacks calcium, and may lack magnesium or may lack many, if not all, divalent cations. As would be appreciated by those of ordinary skill in the art, a washing step may be accomplished by methods known to those in the art, such as by using a semiautomated flowthrough centrifuge. After washing, the cells may be resuspended in a variety of biocompatible buffers or other saline solution with or without buffer. In certain embodiments, the undesirable components of the apheresis sample may be removed in the cell directly resuspended culture media.

In certain embodiments, T cells are isolated from peripheral blood mononuclear cells (PBMCs) by lysing the red blood cells and depleting the monocytes, for example, by centrifugation through a PERCOLL™ gradient. A specific subpopulation of T cells, such as CD28+, CD4+, CD8+, CD45RA+, and CD45RO+ T cells, can be further isolated by positive or negative selection techniques. For example, enrichment of a T cell population by negative selection can be accomplished with a combination of antibodies directed to surface markers unique to the negatively selected cells. One method for use herein is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. Flow cytometry and cell sorting may also be used to isolate cell populations of interest for use in the present disclosure.

PBMCs may be used directly for genetic modification with the CARs using methods as described herein. In certain embodiments, after isolation of PBMC, T lymphocytes are further isolated and in certain embodiments, both cytotoxic and helper T lymphocytes can be sorted into naive, memory, and effector T cell subpopulations either before or after genetic modification and/or expansion. CD8+ cells can be obtained by using standard methods. In some embodiments, CD8+ cells are further sorted into naive, central memory, and effector cells by identifying cell surface antigens that are associated with each of those types of CD8+ cells. In embodiments, memory T cells are present in both CD62L+ and CD62L-subsets of CD8+ peripheral blood lymphocytes. PBMC are sorted into CD62L-CD8+ and CD62L+CD8+ fractions after staining with anti-CD8 and anti-CD62L antibodies. In some embodiments, the expression of phenotypic markers of central memory TCM include CD45RO, CD62L, CCR7, CD28, CD3, and CD127 and are negative for granzyme B. In some embodiments, central memory T cells are CD45RO+, CD62L+, CD8+ T cells. In some embodiments, effector T cells are negative for CD62L, CCR7, CD28, and CD127, and positive for granzyme B and perforin. In some embodiments, naive CD8+ T lymphocytes are characterized by the expression of phenotypic markers of naive T cells including CD62L, CCR7, CD28, CD3, CD 127, and CD45RA.

In certain embodiments, CD4+ T cells are further sorted into subpopulations. For example, CD4+ T helper cells can be sorted into naive, central memory, and effector cells by identifying cell populations that have cell surface antigens. CD4+ lymphocytes can be obtained by standard methods. In some embodiments, naive CD4+ T lymphocytes are CD45RO−, CD45RA+, CD62L+CD4+ T cell. In some embodiments, central memory CD4+ cells are CD62L positive and CD45RO positive. In some embodiments, effector CD4+ cells are CD62L and CD45RO negative.

The immune effector cells, such as T cells, can be genetically modified following isolation using known methods, or the immune effector cells can be activated and expanded (or differentiated in the case of progenitors) in vitro prior to being genetically modified. In another embodiment, the immune effector cells, such as T cells, are genetically modified with the chimeric antigen receptors described herein (e.g., transduced with a viral vector comprising a nucleic acid encoding a CAR) and then are activated and expanded in vitro. Methods for activating and expanding T cells are known in the art and are described, for example, in U.S. Pat. Nos. 6,905,874; 6,867,041; 6,797,514; WO2012079000. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). In other embodiments, the T cells may be activated and stimulated to proliferate with feeder cells and appropriate antibodies and cytokines using methods such as those described in U.S. Pat. Nos. 6,040,177; 5,827,642; and WO2012129514.

The present disclosure provides a population of modified immune effector cells for the treatment of a patient having a malignancy caused by a MAGE-A4-expressing tumor, e.g., multiple myeloma or melanoma, the modified immune effector cells comprising an anti-MAGE-A4 CAR as disclosed herein.

CAR-expressing immune effector cells prepared as described herein can be utilized in methods and compositions for adoptive immunotherapy in accordance with known techniques, or variations thereof that will be apparent to those skilled in the art based on the instant disclosure. See, e.g., US Patent Application Publication No. 2003/0170238 to Gruenberg et al; see also U.S. Pat. No. 4,690,915 to Rosenberg.

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin.

A treatment-effective amount of cells in the composition is at least 2 cells (for example, at least 1 CD8+ central memory T cell and at least 1 CD4+ helper T cell subset) or is more typically greater than $10^2$ cells, and up to $10^6$ up to and including $10^8$ or $10^9$ cells and can be more than $10^{10}$ cells. The number of cells will depend upon the ultimate use for which the composition is intended as will the type of cells included therein.

The cells may be autologous or heterologous to the patient undergoing therapy. If desired, the treatment may also include administration of mitogens (e.g., PHA) or lymphokines, cytokines, and/or chemokines (e.g., IFN-γ, IL-2, IL-12, TNF-α, IL-18, and TNF-β, GM-CSF, IL-4, IL-13, Flt3-L, RANTES, MIP1α, etc.) as described herein to enhance induction of the immune response.

The CAR expressing immune effector cell populations of the present disclosure may be administered either alone, or as a pharmaceutical composition in combination with diluents and/or with other components such as IL-2 or other cytokines or cell populations. Briefly, pharmaceutical compositions of the present disclosure may comprise a CAR-expressing immune effector cell population, such as T cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure are preferably formulated for intravenous administration.

The anti-tumor immune response induced in a subject by administering CAR expressing T cells described herein using the methods described herein, or other methods known in the art, may include cellular immune responses mediated by cytotoxic T cells capable of killing infected cells, regulatory T cells, and helper T cell responses. Humoral immune responses, mediated primarily by helper T cells capable of activating B cells thus leading to antibody production, may also be induced. A variety of techniques may be used for analyzing the type of immune responses induced by the compositions of the present disclosure, which are well described in the art; e.g., Current Protocols in Immunology, Edited by: John E. Coligan, Ada M. Kruisbeek, David H. Margulies, Ethan M. Shevach, Warren Strober (2001) John Wiley & Sons, NY, N.Y.

Thus, the present disclosure provides for methods of treating an individual diagnosed with or suspected of having, or at risk of developing a malignancy characterized at least in part by the expression of MAGE-A4 by cancer cells (e.g., MAGE-A4 expressing solid tumor cells), comprising administering to the individual a therapeutically effective amount of the CAR-expressing immune effector cells as described herein.

In one embodiment, the present disclosure provides a method of treating a subject diagnosed with a MAGE-A4-expressing cancer comprising removing immune effector cells from a subject diagnosed with a MAGE-A4-expressing cancer, genetically modifying said immune effector cells with a vector comprising a nucleic acid encoding a chimeric antigen receptor of the present disclosure, thereby producing a population of modified immune effector cells, and administering the population of modified immune effector cells to the same subject. In one embodiment, the immune effector cells comprise T cells.

The methods for administering the cell compositions described herein includes any method which is effective to result in reintroduction of ex vivo genetically modified immune effector cells that either directly express a CAR of the present disclosure in the subject or on reintroduction of the genetically modified progenitors of immune effector cells that on introduction into a subject differentiate into mature immune effector cells that express the CAR. One method comprises transducing peripheral blood T cells ex vivo with a nucleic acid construct in accordance with the present disclosure and returning the transduced cells into the subject.

Binding Properties of the Chimeric Antigen Receptors and Corresponding Antibodies As used herein, the term "binding" in the context of the binding of a chimeric antigen receptor or a corresponding antibody to, e.g., a predetermined antigen, such as a cell surface protein or fragment thereof (or to an antigen bound to a cell surface protein such as an HLA molecule). Binding typically refers to an interaction or association between a minimum of two entities or molecular structures, such as an antigen-binding domain:antigen interaction.

For instance, binding affinity typically corresponds to a $K_D$ value of about $10^{-7}$ M or less, such as about $10^{-8}$M or less, such as about $10^{-9}$M or less when determined by, for instance, surface plasmon resonance (SPR) technology in a BIAcore 3000 instrument using the antigen as the ligand and the antibody or chimeric antigen receptor as the analyte (or antiligand). Cell-based binding strategies, such as fluorescent-activated cell sorting (FACS) binding assays, are also routinely used, and FACS data correlates well with other methods such as radioligand competition binding and SPR (Benedict, C A, *J Immunol Methods*. 1997, 201(2):223-31; Geuijen, C A, et al. *J Immunol Methods*. 2005, 302(1-2): 68-77).

Accordingly, a chimeric antigen receptor or corresponding antibody of the present disclosure binds to the predetermined antigen or cell surface molecule (receptor) having an affinity corresponding to a $K_D$ value that is at least ten-fold lower than its affinity for binding to a non-specific antigen (e.g., BSA, casein). As described herein, a chimeric antigen receptor or corresponding antibody of the present disclosure can bind to an HLA-presented MAGE-A4 antigen, e.g., an HLA-A2-presented MAGE-A4 antigen. According to the present disclosure, the affinity of a chimeric antigen receptor or a corresponding antibody with a $K_D$ value that is equal to or less than ten-fold lower than a non-specific antigen may be considered non-detectable binding.

The term "$K_D$" (M) refers to the dissociation equilibrium constant of a particular antigen-binding domain:antigen interaction, or the dissociation equilibrium constant of a corresponding antibody to an antigen. There is an inverse relationship between $K_D$ and binding affinity, therefore the smaller the $K_D$ value, the higher, i.e. stronger, the affinity. Thus, the terms "higher affinity" or "stronger affinity" relate to a higher ability to form an interaction and therefore a smaller $K_D$ value, and conversely the terms "lower affinity" or "weaker affinity" relate to a lower ability to form an interaction and therefore a larger $K_D$ value. In some circumstances, a higher binding affinity (or $K_D$) of a particular molecule (e.g., a chimeric antigen receptor or a corresponding antibody) to its interactive partner molecule (e.g. antigen X) compared to the binding affinity of the molecule (e.g., chimeric antigen receptor or corresponding antibody) to another interactive partner molecule (e.g. antigen Y) may be expressed as a binding ratio determined by dividing the larger $K_D$ value (lower, or weaker, affinity) by the smaller $K_D$ (higher, or stronger, affinity), for example expressed as 5-fold or 10-fold greater binding affinity, as the case may be.

The term "$k_d$" (sec-1 or 1/s) refers to the dissociation rate constant of a particular antigen-binding domain:antigen interaction, or the dissociation rate constant of a chimeric antigen receptor or a corresponding antibody. Said value is also referred to as the $k_{off}$ value.

The term "$k_a$" (M-1×sec-1 or 1/M) refers to the association rate constant of a particular antigen-binding domain: antigen interaction, or the association rate constant of a chimeric antigen receptor or a corresponding antibody.

The term "$K_A$" (M-1 or 1/M) refers to the association equilibrium constant of a particular antigen-binding domain: antigen interaction, or the association equilibrium constant of a chimeric antigen receptor or a corresponding antibody. The association equilibrium constant is obtained by dividing the $k_a$ by the $k_d$.

The term "EC50" or "$EC_{50}$" refers to the half maximal effective concentration, which includes the concentration of a chimeric antigen receptor that induces a response halfway between the baseline and maximum after a specified exposure time. The $EC_{50}$ essentially represents the concentration of a chimeric antigen receptor or antibody, where 50% of its maximal effect is observed. In certain embodiments, the $EC_{50}$ value equals the concentration of a chimeric antigen receptor or a corresponding antibody of the present disclosure that gives half-maximal binding to cells expressing an antigen (e.g., a tumor-associated antigen, such as MAGE-A4), as determined by e.g. a FACS binding assay. Thus, reduced or weaker binding is observed with an increased $EC_{50}$, or half maximal effective concentration value.

In one embodiment, decreased binding can be defined as an increased $EC_{50}$ chimeric antigen receptor or corresponding antibody concentration that enables binding to the half-maximal amount of target cells.

Sequence Variants of the Chimeric Antigen Receptors

The chimeric antigen receptors or the present disclosure may comprise one or more amino acid substitutions, insertions and/or deletions in the framework and/or CDR regions of the heavy and light chain variable domains as compared to the corresponding germline sequences from which the individual antigen-binding domains of the corresponding antibodies were derived. Such mutations can be readily ascertained by comparing the amino acid sequences disclosed herein to germline sequences available from, for example, public antibody sequence databases. The chimeric antigen receptors of the present disclosure may comprise antigen-binding domains which are derived from any of the exemplary CDR or variable region amino acid sequences disclosed herein, wherein one or more amino acids within one or more framework and/or CDR regions are mutated to the corresponding residue(s) of the germline sequence from which the corresponding antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies that comprise one or more individual germline mutations or combinations thereof. In certain embodiments, all of the framework and/or CDR residues within the $V_H$ and/or $V_L$ domains are mutated back to the residues found in the original germline sequence from which the antigen-binding domain was originally derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antigen-binding domain was originally derived). Furthermore, the antigen-binding domains may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence.

Biological Characteristics of the Chimeric Antigen Receptors and Corresponding Antibodies The present disclosure provides chimeric antigen receptors with antigen-binding domains derived from antibodies that bind human MAGE-A4 with high affinity (e.g., nanomolar or sub-nanomolar $K_D$ values).

According to certain embodiments, the present disclosure provides chimeric antigen receptors with antigen-binding domains derived from corresponding antibodies that bind human MAGE-A4 (e.g., at 25° C.) with a $K_D$ of less than about 5 nM as measured by surface plasmon resonance. In certain embodiments, the corresponding antibodies bind MAGE-A4 with a $K_D$ of less than about 20 nM, less than about 10 nM, less than about 8 nM, less than about 7 nM, less than about 6 nM, less than about 5 nM, less than about 4 nM, less than about 3 nM, less than about 2 nM, less than about 1 nM, less than about 800 pM, less than about 700 pM, less than about 500 pM, less than about 400 pM, less than about 300 pM, less than about 200 pM, less than about 100 pM, less than about 50 pM, or less than about 25 pM as measured by surface plasmon resonance.

The present disclosure also provides chimeric antigen receptors with antigen-binding domains derived from corresponding antibodies that bind MAGE-A4 with a dissociative half-life ($t\frac{1}{2}$) of greater than about 10 minutes or greater than about 125 minutes as measured by surface plasmon resonance at 25° C. In certain embodiments, the corresponding antibodies bind MAGE-A4 with a $t\frac{1}{2}$ of greater than about 3 minutes, greater than about 4 minutes, greater than about 10 minutes, greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 100 minutes, greater than about 110 minutes, or greater than about 120 minutes, as measured by surface plasmon resonance at 25° C.

The present disclosure also provides chimeric antigen receptors with antigen-binding domains derived from corresponding antibodies that bind specifically to human cell lines which express endogenous MAGE-A4, as determined by a FACS binding assay.

The present disclosure also provides engineered cells expressing MAGE-A4-specific chimeric antigen receptors that (i) are activated by MAGE-A4-expressing cells, and/or (ii) exhibit inhibition of tumor growth in immunocompromised mice bearing human multiple myeloma or melanoma xenografts.

Preparation of Antigen-Binding Domains

The antigen-binding domains of the chimeric antigen receptors of the present disclosure, which are specific for particular antigens (e.g., MAGE-A4), can be prepared by any antibody generating technology known in the art. In certain embodiments, one or more of the individual components (e.g., heavy and light chains) of the corresponding antibodies of the present disclosure are derived from chimeric, humanized or fully human antibodies. Methods for making such antibodies are well known in the art. For example, one or more of the heavy and/or light chains can be prepared using VELOCIMMUNE™ technology. Using VELOCIMMUNE™ technology (or any other human antibody generating technology), high affinity chimeric antibodies to a particular antigen (e.g., MAGE-A4) are initially isolated having a human variable region and a mouse constant region. The antibodies are characterized and selected for desirable characteristics, including affinity, selectivity, epitope, etc. As discussed herein, these human variable regions (or CDRs) can then be incorporated into the antigen-binding domains of the chimeric antigen receptors.

Polynucleotides and Vectors

The present disclosure also provides polynucleotides and vectors encoding the chimeric antigen receptors discussed herein.

In various embodiments, the polynucleotide may comprise an expression cassette or expression vector (e.g., a plasmid for introduction into a bacterial host cell, or a viral vector such as a baculovirus vector for transfection of an insect host cell, or a plasmid or viral vector such as a lentivirus for transfection of a mammalian host cell).

In various embodiments, the polynucleotides and/or vectors comprise a nucleic acid molecule comprising the nucleotide sequence of SEQ ID NO: 21, or comprise a nucleic acid molecule comprising a nucleotide sequence encoding the polypeptide sequence of SEQ ID NO: 22. In various embodiments, the polynucleotides and/or vectors comprise a nucleic acid molecule comprising the nucleotide sequence of SEQ ID NO: 38, or comprise a nucleic acid molecule comprising a nucleotide sequence encoding the polypeptide sequence of SEQ ID NO: 39. In various embodiments, the polynucleotides and/or vectors comprise a nucleotide sequence encoding the amino acid sequence of SEQ ID NO: 27, SEQ ID NO: 28, SEQ ID NO: 29, or SEQ ID NO: 30.

Methods of Engineering Immune Cells Expressing Chimeric Antigen Receptors

The present disclosure provides methods of preparing immune cells for immunotherapy comprising introducing, ex vivo, into such immune cells the polynucleotides or vectors encoding one of the MAGE-A4-specific chimeric antigen receptors described herein.

The present disclosure provides immune cells comprising a polynucleotide or lentiviral vector encoding one of the MAGE-A4-specific chimeric antigen receptors discussed herein. In some embodiments, these immune cells are used for immunotherapy (e.g., treatment of cancer).

The present disclosure provides methods of genetically modifying immune cells to make them more suitable for allogeneic transplantation. According to a first aspect, the immune cell can be made allogeneic, for instance, by inactivating at least one gene expressing one or more component of T-cell receptor (TCR) as described in WO 2013/176915, which can be combined with the inactivation of a gene encoding or regulating HLA or β2m protein expression. Accordingly, the risk of graft versus host syndrome and graft rejection is significantly reduced. According to further aspect of the present disclosure, the immune cells can be further manipulated to make them more active or limit exhaustion, by inactivating genes encoding proteins that act as "immune checkpoints" that act as regulators of T-cells activation, such as PD1 or CTLA-4.

Engineered Immune Cells

The present disclosure also provides immune cells (e.g., engineered immune cells) comprising a chimeric antigen receptor as described herein. In some cases, the immune cell is an immune effector cell. In some cases, the immune cell is a T cell. In some cases, the immune cell is a T lymphocyte selected from an inflammatory T lymphocyte, a cytotoxic T lymphocyte, a regulatory T lymphocyte, or a helper T lymphocyte. In some cases, the immune cell is a CD8+ cytotoxic T lymphocyte.

In some embodiments, the engineered immune cell is a human T cell comprising a chimeric antigen receptor comprising, from N-terminus to C-terminus: (a) an extracellular ligand-binding domain comprising an anti-MAGE-A4 single chain variable fragment (scFv) domain comprising a light chain variable region (LCVR) and a heavy chain variable region (HCVR); (b) a hinge; (c) a transmembrane domain; and (d) a cytoplasmic domain comprising a costimulatory domain and a signaling domain.

In some embodiments, the scFv domain of the engineered human T cell comprises a HCVR/LCVR amino acid sequence pair comprising the amino acid sequences of SEQ ID NOs: 2/10. In some embodiments, the scFv domain of the engineered human T cell comprises a HCVR/LCVR amino acid sequence pair comprising the amino acid sequences of SEQ ID NOs: 2/37. In some cases, the hinge comprises the amino acid sequence of SEQ ID NO: 27. In some cases, the transmembrane domain comprises the amino acid sequence of SEQ ID NO: 28. In some cases, the costimulatory domain is a 4-1BB costimulatory domain. In some cases, the 4-1BB costimulatory domain comprises the amino acid sequence of SEQ ID NO: 29. In some cases, the signaling domain is a CD3zeta signaling domain. In some cases, the CD3zeta signaling domain comprises the amino acid sequence of SEQ ID NO: 30.

In various embodiments, the engineered human T cell comprises a chimeric antigen receptor comprising the amino acid sequence of SEQ ID NO: 22. In various embodiments, the engineered human T cell comprises a chimeric antigen receptor comprising the amino acid sequence of SEQ ID NO: 39.

Bioequivalents

The present disclosure provides chimeric antigen receptors and engineered cells expressing the chimeric antigen receptors, which have amino acid sequences that vary from those of the exemplary molecules disclosed herein but that retain the ability to bind MAGE-A4, activate immune cells expressing the chimeric antigen receptors in the presence of MAGE-A4-expressing cells, or suppress growth or prolif- eration of MAGE-A4-expressing tumor cells. Such variant molecules may comprise one or more additions, deletions, or substitutions of amino acids when compared to a parent sequence, but exhibit biological activity that is essentially equivalent to that of the described bispecific antigen-binding molecules.

In one embodiment, two engineered immune cells expressing a chimeric antigen receptor of the present dis- closure are bioequivalent if there are no clinically meaning- ful differences in their safety, purity, and potency.

In one embodiment, two engineered immune cells are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two engineered immune cells are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the engineered cell is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the engineered cell (or its target) is measured as a function of time; and (d) in a well-controlled clinical trial that establishes safety, efficacy, or bioavailability or bioequivalence of an engi- neered cell.

Bioequivalent variants of the exemplary engineered cells set forth herein may be constructed by, for example, making various substitutions of residues or sequences or deleting terminal or internal residues or sequences not needed for biological activity.

Species Selectivity and Species Cross-Reactivity

According to certain embodiments of the present disclo- sure, antigen-binding domains are provided which bind to human MAGE-A4, but not to MAGE-A4 from other spe- cies. The present disclosure also provides antigen-binding domains that bind to human MAGE-A4 and to MAGE-A4 from one or more non-human species. In some embodi- ments, the antigen-binding domains of the present disclosure bind to MAGE-A4 286-294 or 230-239. In some embodi- ments, the MAGE-A4 to which an antigen-binding domain binds (e.g., MAGE-A4 286-294 or 230-239) is presented on the surface of a cell by an HLA, e.g., HLA-A2.

According to certain exemplary embodiments of the pres- ent disclosure, antigen-binding domains are provided which bind to human MAGE-A4 and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee MAGE-A4. Moreover, the binding to MAGE-A4 can be in the context of an MHC-presented MAGE-A4, such as an HLA-presented MAGE-A4. An exemplary HLA-presented MAGE-A4 is HLA-A2-bound human MAGE-A4.

Activation and Expansion of Engineered Immune Cells

Whether prior to or after genetic modification of the engineered cells (e.g., T cells), even if the genetically modified immune cells of the present disclosure are acti- vated and proliferate independently of antigen binding mechanisms, the immune cells, particularly T-cells of the present disclosure can be further activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publica- tion No. 20060121005. T cells can be expanded in vitro or in vivo.

Generally, the T cells of the present disclosure are expanded by contact with an agent that stimulates a CD3 TCR complex and a costimulatory molecule on the surface of the T cells to create an activation signal for the T-cell. For example, chemicals such as calcium ionophore A23187, phorbol 12-myristate 13-acetate (PMA), or mitogenic lectins like phytohemagglutinin (PHA) can be used to create an activation signal for the T-cell.

As non-limiting examples, T cell populations may be stimulated in vitro such as by contact with an anti-CD3 antibody, or antigen-binding fragment thereof, or an anti- CD2 antibody immobilized on a surface, or by contact with a protein kinase C activator (e.g., bryostatin) in conjunction with a calcium ionophore. For costimulation of an accessory molecule on the surface of the T cells, a ligand that binds the accessory molecule is used. For example, a population of T cells can be contacted with an anti-CD3 antibody and an anti-CD28 antibody, under conditions appropriate for stimu- lating proliferation of the T cells. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, IL-4, IL-7, GM-CSF, IL-10, IL-2, IL-15, TGFp, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $O_2$). T cells that have been exposed to varied stimulation times may exhibit different characteristics.

In some embodiments, the cells can be expanded by co-culturing with tissue or cells. The cells can also be expanded in vivo, for example in the subject's blood after administrating said cell into the subject.

Therapeutic Applications

The present disclosure provides compositions comprising an engineered cell (e.g., a T cell) expressing a chimeric antigen receptor of the present disclosure and a pharmaceutically acceptable vehicle. In some cases, the engineered cells form a medicament, particularly for immunotherapy. In some cases, the engineered cells are used for the treatment of cancer (e.g., multiple myeloma or melanoma). In some cases, the engineered cells are used in the manufacture of a medicament for immunotherapy and/or the treatment of a cancer (e.g., a MAGE-A4-expressing cancer).

The present disclosure provides methods comprising administering to a subject in need thereof a therapeutic composition comprising an engineered cell (e.g., a T cell) expressing a chimeric antigen receptor as discussed herein. The therapeutic composition can comprise a cell expressing any chimeric antigen receptor as disclosed herein and a pharmaceutically acceptable carrier, diluent or vehicle. As used herein, the expression "a subject in need thereof" means a human or non-human animal that exhibits one or more symptoms or indicia of cancer (e.g., a subject with a MAGE-A4-expressing tumor or suffering from any of the cancers mentioned herein), or who otherwise would benefit from an inhibition or reduction in MAGE-A4 activity or a depletion of MAGE-A4+ cells.

The engineered cells of the present disclosure can be useful, inter alia, for treating any disease or disorder in which stimulation, activation and/or targeting of an immune response would be beneficial. In particular, the engineered cells of the present disclosure may be used for the treatment, prevention and/or amelioration of any disease or disorder associated with or mediated by MAGE-A4 expression or activity or the proliferation of MAGE-A4+ cells. Cells expressing MAGE-A4 which can be inhibited or killed using the engineered cells of the present disclosure include, for example, multiple myeloma cells, melanoma cells, or other solid tumor cells.

The engineered cells of the present disclosure may be used to treat a disease or disorder associated with MAGE-A4 expression including, e.g., a cancer including but not limited to multiple myeloma, synovial sarcoma, esophageal cancer, head and neck cancer, lung cancer, bladder cancer, ovarian cancer, uterine cancer, stomach cancer, cervical cancer, breast cancer, and melanoma. The engineered cells of the present disclosure may generally be used to treat a tumor that expresses MAGE-A4. According to other related embodiments of the present disclosure, methods are provided comprising administering an engineered cell as disclosed herein to a patient who is afflicted with a tumor expressing MAGE-A4, including tumors from the cancers listed above. Analytic/diagnostic methods known in the art, such as tumor scanning, etc., may be used to ascertain whether a patient harbors such a tumor, disease, or condition.

The present disclosure also provides methods for treating residual cancer in a subject. As used herein, the term "residual cancer" means the existence or persistence of one or more cancerous cells in a subject following treatment with an anti-cancer therapy.

According to certain aspects, the present disclosure provides methods for treating a disease or disorder associated with MAGE-A4 expression (e.g., cancer) comprising administering a population of engineered cells described elsewhere herein to a subject after the subject has been determined to have the disease or disorder. For example, the present disclosure provides methods for treating a disease or disorder comprising administering engineered immune cells to a patient 1 day, 2 days, 3 days, 4 days, 5 days, 6 days, 1 week, 2 weeks, 3 weeks or 4 weeks, 2 months, 4 months, 6 months, 8 months, 1 year, or more after the subject has received other immunotherapy or chemotherapy.

The treatments discussed herein can be ameliorating, curative or prophylactic. Treatments may be either part of an autologous immunotherapy or part of an allogeneic immunotherapy. By autologous, it is meant that the cells, cell line or population of cells used for treating patients are originating from the patient or from a Human Leucocyte Antigen (HLA) compatible donor. By allogeneic is meant that the cells, cell line or population of cells used for treating patients are not originating from the patient but from a donor.

Cells that can be used with the disclosed methods are described herein. The treatments can be used to treat patients diagnosed with a pre-malignant or malignant cancer condition characterized by MAGE-A4-expressing cells, especially by an overabundance of MAGE-A4-expressing cells. Such conditions can be found in cancers.

Types of cancers to be treated with the engineered cells of the present disclosure include, but are not limited to, multiple myeloma, synovial sarcoma, esophageal cancer, head and neck cancer, lung cancer, bladder cancer, ovarian cancer, uterine cancer, stomach cancer, cervical cancer, breast cancer, and melanoma.

Compositions and methods of the present disclosure may be used to treat a subject who has been characterized as having cells or tissues expressing MAGE-A4, or is suspected of having cells or tissues expressing MAGE-A4. For example, subjects benefiting from treatment according to the present disclosure include subjects with multiple myeloma, synovial sarcoma, esophageal cancer, head and neck cancer, lung cancer, bladder cancer, ovarian cancer, uterine cancer, stomach cancer, cervical cancer, breast cancer, or melanoma.

The administration of the cells or population of cells according to the present disclosure may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present disclosure are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administered in one or more doses. In some embodiments, the effective amount of cells is administered as a single dose. In some embodiments, the effective amount of cells is administered as more than one dose over a period time. Timing of administration is within the judgment of managing physician and depends on the clinical condition of the patient. The cells or population of cells may be obtained from any source, such as a blood bank or a donor. While individual needs vary, determination of ranges of effective amounts of a given cell type for a particular disease or condition are within the skill of the art. An effective amount means an amount which provides a therapeutic or prophylactic benefit. The dosage administered will be dependent upon the age, health and weight of the recipient, kind of concurrent treatment, if any, frequency of treatment and the nature of the effect desired.

In one embodiment, the effective amount of cells or composition comprising those cells is administered parenterally. This administration can be an intravenous administration. In some cases, administration can be directly done by injection within a tumor.

In certain embodiments of the present disclosure, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efaliztimab treatment for psoriasis patients or other treatments for PML patients. In further embodiments, the T cells of the present disclosure may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycophenolic acid, steroids, FR901228, cytokines, and irradiation.

In a further embodiment, the cell compositions of the present disclosure are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present disclosure are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present disclosure. In an additional embodiment, expanded cells are administered before or following surgery. In certain embodiments, any means (e.g., surgery, chemotherapy, or radiation therapy) may be used to reduce the tumor burden prior to administration of the expanded immune cells of the present disclosure. In one embodiment, reducing the tumor burden prior to administration of the engineered cells of the present disclosure can reduce the potential for, or prevent, cytokine release syndrome or a cytokine storm, a side effect that may be associated with CAR T cell therapy.

Combination Therapies

The present disclosure provides methods which comprise administering engineered cells or a population of cells comprising any of the chimeric antigen receptors described herein in combination with one or more additional therapeutic agents. Exemplary additional therapeutic agents that may be combined with or administered in combination with the cells or population of cells of the present disclosure include, e.g., an anti-tumor agent (e.g. chemotherapeutic agents including melphalan, vincristine (Oncovin), cyclophosphamide (Cytoxan), etoposide (VP-16), doxorubicin (Adriamycin), liposomal doxorubicin (Doxil), obendamustine (Treanda), or any others known to be effective in treating a plasma cell tumor in a subject). In some embodiments, the second therapeutic agent comprises steroids. In some embodiments, the second therapeutic agent comprises targeted therapies including thalidomide, lenalidomide, and bortezomib, which are therapies approved to treat newly diagnosed patients. For example, lenalidomide, pomalidomide, bortezomib, carfilzomib, panobinostat, ixazomib, elotumab, and daratumumab are examples of a second therapeutic agent effective for treating recurrent myeloma. In certain embodiments the second therapeutic agent is a regimen comprising radiotherapy or a stem cell transplant. In certain embodiments, the second therapeutic agent may be an immunomodulatory agent. In certain embodiments, the second therapeutic agent may be a proteasome inhibitor, including bortezomib (Velcade®), carfilzomib (Kyprolis®), ixazomib (Ninlaro®). In certain embodiments the second therapeutic agent may be a histone deacetylase inhibitor such as panobinostat (Farydak®). In certain embodiments, the second therapeutic agent may be a monoclonal antibody, an antibody drug conjugate, a bispecific antibody conjugated to an anti-tumor agent, a checkpoint inhibitor, or combinations thereof. Other agents that may be beneficially administered in combination with the antigen-binding molecules of the present disclosure include cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors. The pharmaceutical compositions of the present disclosure (e.g., pharmaceutical compositions comprising engineered cells or populations of cells as disclosed herein) may also be administered as part of a therapeutic regimen comprising one or more therapeutic combinations selected from a monoclonal antibody other than those described herein, which may interact with a different antigen on the plasma cell surface, a bispecific antibody, which has one arm that binds to an antigen on the tumor cell surface and the other arm binds to an antigen on a T cell, an antibody drug conjugate, a bispecific antibody conjugated with an anti-tumor agent, a checkpoint inhibitor, for example, one that targets, PD-1 or CTLA-4, or combinations thereof. In certain embodiments, the checkpoint inhibitors may be selected from PD-1 inhibitors, such as pembrolizumab (Keytruda®), nivolumab (Opdivo®), or cemiplimab (Libtayo®). In certain embodiments, the checkpoint inhibitors may be selected from PD-L1 inhibitors, such as atezolizumab (Tecentriq®), avelumab (Bavencio®), or Durvalumab (Imfinzi®). In certain embodiments, the checkpoint inhibitors may be selected from CTLA-4 inhibitors, such as ipilimumab (Yervoy®).

The present disclosure also includes therapeutic combinations comprising any of the engineered cells or populations of cells mentioned herein and an inhibitor of one or more of VEGF, Ang2, DLL4, EGFR, ErbB2, ErbB3, ErbB4, EGFRvIII, cMet, IGF1R, B-raf, PDGFR-$\alpha$, PDGFR-$\beta$, FOLH1 (PSMA), PRLR, STEAP1, STEAP2, TMPRSS2, MSLN, CA9, uroplakin, or any of the aforementioned cytokines, wherein the inhibitor is an aptamer, an antisense molecule, a ribozyme, an siRNA, a peptibody, a nanobody or an antibody fragment (e.g., Fab fragment; F(ab')$_2$ fragment; Fd fragment; Fv fragment; scFv; dAb fragment; or other engineered molecules, such as diabodies, triabodies, tetrabodies, minibodies and minimal recognition units). In some embodiments, the engineered cells or population of cells of the present disclosure may also be administered as part of a treatment regimen that also includes radiation treatment and/or conventional chemotherapy.

The additional therapeutically active component(s) may be administered just prior to, concurrent with, or shortly after the administration of the engineered cells of the present disclosure; (for purposes of the present disclosure, such administration regimens are considered the administration of the engineered cells "in combination with" an additional therapeutically active component).

The present disclosure provides pharmaceutical compositions in which an engineered cell or population of cells of the present disclosure is co-formulated with one or more of the additional therapeutically active component(s) as described elsewhere herein.

Administration Regimens

According to certain embodiments of the present disclosure, multiple doses of the engineered cells may be administered to a subject over a defined time course. The methods according to this aspect comprise sequentially administering to a subject multiple doses of the cells. As used herein, "sequentially administering" means that each dose is administered to the subject at a different point in time, e.g., on different days separated by a predetermined interval (e.g., hours, days, weeks or months). The present disclosure provides methods which comprise sequentially administering to the patient a single initial dose, followed by one or more secondary doses, and optionally followed by one or more tertiary doses.

The terms "initial dose," "secondary doses," and "tertiary doses," refer to the temporal sequence of administration of the engineered cells of the present disclosure. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of engineered cells, but generally may differ from one another in terms of frequency of administration. In certain embodiments, however, the amount of engineered cells contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present disclosure, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose which is administered to a patient prior to the administration of the very next dose in the sequence with no intervening doses.

The methods according to this aspect of the present disclosure may comprise administering to a patient any number of secondary and/or tertiary doses. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

EXAMPLES

The following examples are put forth so as to provide those of ordinary skill in the art with a complete disclosure and description of how to make and use the methods and compositions of the present disclosure, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Generation of Anti-MAGE-A4 Antibodies

Anti-MAGE-A4 antibodies were obtained by immunizing a genetically modified mouse (e.g., an engineered mouse comprising DNA encoding human immunoglobulin heavy and kappa light chain variable regions) with a human MAGE-A4 antigen (e.g., hMAGE-A4 230-239 for mAb31345 or hMAGE-A4 286-294 for mAb33229) and HLA-A2.

Following immunization, splenocytes were harvested from each mouse and either (1) fused with mouse myeloma cells to preserve their viability and form hybridoma cells and screened for MAGE-A4 specificity, or (2) B-cell sorted (as described in US Patent Pub. No. 2007/0280945A1) using a human MAGE-A4 fragment as the sorting reagent that binds and identifies reactive antibodies (antigen-positive B cells).

Chimeric antibodies to MAGE-A4 were initially isolated having a human variable region and a mouse constant region. The antibodies were characterized and selected for desirable characteristics, including affinity, selectivity, etc. If necessary, mouse constant regions were replaced with a desired human constant region, for example wild-type or modified IgG1 or IgG4 constant region, to generate a fully human anti-MAGE-A4 antibody. While the constant region selected may vary according to specific use, high affinity antigen-binding and target specificity characteristics reside in the variable region.

Heavy and Light Chain Variable Region Amino Acid and Nucleic Acid Sequences of anti-MAGE-A4 antibodies: Table 1 sets forth the amino acid sequence identifiers of the heavy and light chain variable regions and CDRs of selected anti-MAGE-A4 antibodies of the present disclosure. The mAb31345 and mAb31345* sequences of Table 1 are identical except for one extra C-terminal amino acid in the "called" LCVR sequence of mAb31345* (i.e., the full-length antibodies are identical but one additional amino acid was assigned to the LCVR of mAb31345* when annotating the LCVR region). The corresponding nucleic acid sequence identifiers are set forth in Table 2. A summary of all sequences contained herein is provided in Table 56.

TABLE 1

| Amino Acid Sequence Identifiers | | | | | | | |
| --- | --- | --- | --- | --- | --- | --- | --- |
| Antibody | SEQ ID NOs: | | | | | | |
| Designation | HCVR | HCDR1 | HCDR2 | HCDR3 | LCVR | LCDR1 | LCDR2 | LCDR3 |
| mAb31345 | 2 | 4 | 6 | 8 | 37 | 12 | 14 | 16 |
| mAb31345* | 2 | 4 | 6 | 8 | 10 | 12 | 14 | 16 |
| mAb33229 | 51 | 53 | 55 | 57 | 59 | 61 | 63 | 65 |

TABLE 2

| Nucleic Acid Sequence Identifiers | | | | | | | |
| --- | --- | --- | --- | --- | --- | --- | --- |
| Antibody | SEQ ID NOs: | | | | | | |
| Designation | HCVR | HCDR1 | HCDR2 | HCDR3 | LCVR | LCDR1 | LCDR2 | LCDR3 |
| mAb31345 | 1 | 3 | 5 | 7 | 36 | 11 | 13 | 15 |
| mAb31345* | 1 | 3 | 5 | 7 | 9 | 11 | 13 | 15 |
| mAb33229 | 50 | 52 | 54 | 56 | 58 | 60 | 62 | 64 |

Example 2: Generation of MAGE-A4-Specific Chimeric Antigen Receptors

The anti-MAGE-A4 31345 and 33229 antibodies of Table 1 were reformatted into a VL-VH single chain variable fragment (ScFv) and placed into a chimeric antigen receptor (CAR) construct that used a CD8α hinge and transmembrane domain, 4-1BB costimulatory domain, and a CD3zeta stimulatory domain, or a CD28 hinge, transmembrane, and signaling domain using the HCVR and LCVR nucleotide sequences of an anti-MAGE-A4 antibody corresponding to SEQ ID NOs: 1 and 36, respectively. The full-length nucleic acid and polypeptide heavy chain sequences of the corresponding 31345 anti-MAGE-A4 antibody correspond to SEQ ID NOs: 17 and 18, respectively. The full-length nucleic acid and polypeptide light chain sequences of the corresponding 31345 anti-MAGE-A4 antibody correspond to SEQ ID NOs: 19 and 20, respectively. The full length nucleic acid and polypeptide 31345 HLA-A2/MAGE-A4$_{286-294}$-targeted CAR sequences correspond to SEQ ID NOs: 38 and 39, respectively. As a non-binding control, a similar CAR was designed using the nucleotide sequence of an irrelevant scFv (CAR construct of SEQ ID NO: 34; the polypeptide sequence of the control CAR corresponds to SEQ ID NO: 35). The MAGE-A4-specific CAR was cloned into a lentiviral expression vector (LENTI-X™ Bicistronic Expression System (Neo), Clontech Cat #632181) and lentiviral particles were generated via the LENTI-X™ Packaging Single-Shot (VSV-G) system (Clontech Cat #631276) according to manufacturer protocols. Jurkat cells engineered to express an NFKB-luciferase reporter (Jurkat/NKFBLuc cl 1C11) were then transduced with the CAR construct using RETRONECTIN® Precoated Dishes (Clontech, Cat

T110a) according to manufacturer's protocols. Following selection for at least 2 weeks in 500 µg/ml G418 (Gibco, Cat #11811-098), the following CAR T cell line was generated; Jurkat/NKFBLuc cl 1C11/MAGE-A4 (286-294) 31345 VL-VH CART. As a non-binding control, a similar CAR was designed using the nucleotide sequence of an irrelevant scFv. This CAR T cell line was evaluated for cell surface expression and functional activity in response to MAGE-A4 expressing cells.

Example 3: Cell Surface Expression of MAGE-A4 CAR Constructs in Jurkat Cells and Activation of MAGE-A4 CAR T Cells The relative level of cell surface expression of the MAGE-A4 CAR construct in Jurkat/Jurkat/NKFBLuc cells was assessed by flow cytometry. To stain, cells were plated in staining buffer of PBS without calcium and magnesium (Irving 9240), and 2% FBS (ATCC 30-2020) at a density of 200,000 cells per well in a 96 well V-Bottom plate and stained for 30 mins at 4° C. with 10 µg/ml of Protein L (Genscript Biotin Protein L). Following incubation, cells were washed once in staining buffer, and stained with streptavidin Alexa-647 secondary antibody (Biolegend) at 0.5 µg/ml for 30 mins at 4° C. Cells were then washed and fixed using a 50% solution of BD Cytofix (Becton Dickinson) diluted in staining buffer. Samples were run on the Intellicyt iQue flow cytometer and analyzed by FlowJo 10.2 to calculate the mean fluorescent intensity (MFI). The percent of Protein L positive cells (Table 3) was calculated by taking the percent of Protein L positive cells with respect to the total number of cells.

Activity of the CAR T cell lines was assessed in a CAR T/APC (antigen presenting cell) bioassay. To perform the bioassay, 50,000 CAR T cells were added to Thermo-Nunc 96-well white plates (Thermo Fisher Scientific) in 50 µl of assay media (RPMI media with 10% FBS and 1% P/S/G) followed by the addition of a 3-fold serial dilution of APCs (500,000 cells to 685 cells) in 50 µl of assay media. The following APCs were utilized: IM9 (which endogenously express the MAGE-A4 286-294 peptide), and HEK293 (which are MAGE-A4 286-294 negative). The cell mixtures were incubated in a 37° C., 5% $CO_2$, humidified incubator for 5 hours. NFKB-Luciferase activity was measured using Promega One-Glo and a Perkin Elmer Envision plate reader. Relative luciferase units (RLU) were generated and plotted in GraphPad Prism using a four-parameter logistic equation over an 8-point response curve. The zero APC condition for each dose-response curve was also included in the analysis as a continuation of the three-fold serial dilution and represented as the lowest dose. Maximal CAR T activity was determined by taking the ratio of the highest RLU on the curve to the lowest and is represented in Table 4 as signal: noise (S:N). Results of Protein L staining and MAGE-A4 CAR T cell activation are shown in Tables 3 and 4.

TABLE 3

Protein L staining of CARs in Jurkat/NFKBLuc cl 1C11 cells

| Cell Line | % Protein L positive |
|---|---|
| Jurkat/NFKBLuc cl. 1C11 | 3.9 |
| Jurkat/NFKBLuc cl. 1C11/MAGE-A4 (286-294) 31345 VL-VH CAR T-cells | 49.9 |
| Jurkat/NFKBLuc cl. 1C11/Control VL-VH CAR T-cells | 67.2 |

Table 3 shows the percent of CAR positive Jurkat/NFK-BLuc cells, as measured by protein L staining. The MAGE-A4 specific CAR generated from mAb31345 expressed in 49.9% of cells, while the non-targeting control CAR was expressed in 67.2% of cells, and CAR expression was found in only 3.9% of negative control (Jurkat/NFKBLuc cl. 1C11) cells.

TABLE 4

| Activation of MAGE-A4 CAR T cells in a CAR T cell/APC Bioassay | | | |
|---|---|---|---|
| Antigen | CAR T Cell Maximal Activity (Signal:Noise) | | |
| Presenting Cell | Parental Cell | MAGE-A4 (286-294) 31345 CAR | Control CAR |
| IM9 | 5.2 | 35.0 | 4.9 |
| HEK293 | 1.0 | 0.9 | 0.8 |

Table 4 shows that the HLA-A2:MAGE-A4 (286-294) 31345 CAR T cell line was activated by IM9 cells with a signal to noise ratio of 35.0, while the HLA-A2:MAGE-A4 (286-294) CAR T cell line was not activated by the HEK 293 negative control cell line.

Example 4: Generation of CAR T Cells Expressing a MAGE-A4-Specific CAR

The CAR of Example 2 (containing an anti-MAGE-A4 VL-VH scFv, a huCD8 transmembrane domain, a 4-1BB co-stimulatory domain, and a CD3zeta signaling domain were and constructed using the HCVR and LCVR nucleotide sequences of an anti-MAGE-A4 antibody corresponding to SEQ ID NOs: 1 and 36, respectively) and the non-binding control CAR of Example 2 (CAR construct of SEQ ID NO: 34; the polypeptide sequence of the control CAR corresponds to SEQ ID NO: 35) were cloned into a pLVX lentiviral vector with an EF1a promoter and IRES: eGFP sequence (for tracking CAR-transduced cells) and VSV-pseudotyped lentivirus was produced. CD3+ T cells were then isolated from human peripheral blood mononuclear cells (PBMCs), stimulated with CD3/CD28 microbeads plus 100 U/ml recombinant human IL-2, and transduced with the lentivirus at an MOI=5. The transduced cells were expanded for 19 days with CD3/CD28 microbeads plus 100 U/ml recombinant human IL-2 before being cryopreserved until use during in vivo experiments. These lines of CAR T cells were used to evaluate cytotoxicity in vitro and efficacy in the reduction of tumor burden in vivo.

Example 5: MAGE-A4-Specific CAR T Cells Mediate Cytolysis of MAGE-A4-Expressing Cells CD3+ T cells were isolated from human peripheral blood mononuclear cells (PBMCs), stimulated with CD3/CD28 microbeads plus 100 U/ml recombinant human IL-2, and transduced with the lentivirus at an MOI=5, as described above. The transduced cells were expanded for 19 days with CD3/CD28 microbeads plus 100 U/ml recombinant human IL-2 before setting up a cytolytic assay.

To determine the cytolytic capacity of MAGE-A4-targeted chimeric antigen receptor (CAR) T cells, a cytolytic assay was performed using expanded CAR T cells and various tumor target cell lines that express variable levels of MAGE-A4. On day 19 of expansion, the expanded CAR T cells were co-cultured in triplicate at various ratios with calcein labeled MAGE-A4+ or control target cell lines. Calcein is a cell permeant fluorescent dye with excitation and emission wavelengths of 495 and 515 nm, respectively. After 2.5 hours, the percent cytotoxicity was calculated based on the amount of calcein dye released from the target cells, which occurs when membrane integrity fails, as ((calcein signal–spontaneous calcein release)/(calcein maximum release–spontaneous calcein release))*100. To determine maximum calcein release, target cells were treated with a 1% solution of Triton-X-114 detergent over the course of the assay. To determine spontaneous calcein release, MAGE-A4+ target cells were labeled with calcein and then cultured in the absence of CAR T cells.

2 hour Calcein Cytotoxicity Assay: At harvest, expanding CAR T cells were washed and resuspended in Optimizer cell culture media. Each target cell line was harvested and resuspended at a density of $2\times10^6$/mL before adding calcein-AM dye at a concentration of 8 μM for 35 minutes at 37° C. After calcein labeling, target cells were washed twice to remove extra calcein. Subsequently, T cells and target cells were co-cultured on a 96 well round bottom plate at various ratios and cultured at 37° C. for 2.5 hours when culture supernatant was harvested. For a negative control, target cells were co-cultured with T cells generated using a similar CAR designed to contain an irrelevant scFv that does not recognize HLA-A2-bound MAGE-A4$_{286-294}$. This CAR scFv control was an anti-HLA-A2/HPV16E7(11-19) scFv (in VL-VH orientation). Lentivirus was used as the vector to introduce the scFvs into the cells. As a CAR negative control, untransduced and expanded T cells from the same normal healthy donor was used. As a control for antigen specific CAR T cell mediated killing, the 293T human embryonic kidney cell line expressing SV40 antigen was used, as this cell line is negative for MAGE-A4 expression. To determine if calcein was being spontaneously released from MAGE-A4+ target cell lines, each cell line was cultured in the absence of CAR T cells. To determine the maximum possible release of calcein, target cell lines were cultured and lysed using Optimizer media that was supplemented to contain 1% TRITON™ X-114 detergent. Within the supernatant, the relative calcein levels were measured using a Viktor X4 plate reader and percent cytotoxicity was calculated as ((Calcein signal–Spontaneous Calcein Release)/(Calcein Maximum Release–Spontaneous Calcein Release))*100.

Cell lines used for this assay included the following: A375 human melanoma tumor cell line (ATCC®, Cell line number: CRL-9068™), A375 human melanoma tumor cell line (ATCC, Cell line number: CRL9068™) engineered to over-express HLA-A2 loaded with MAGE-A4$_{286-294}$ peptide, IM9 multiple myeloma cell line (DSMZ, CAT #: ACC569), IM9 multiple myeloma cell line (DSMZ, CAT #: ACC569™) engineered to overexpress HLA-A2 loaded with MAGE-A4$_{286-294}$ peptide, 293T human embryonic kidney cell line expressing SV40 antigen (ATCC®, Cell line number: CRL-3216™), and CaSKI cervical epidermoid carcinoma (ATCC® CRL-1550™) engineered to overexpress HLA-A2 loaded with HPV16E7$_{11-19}$ peptide.

Figure 2A:
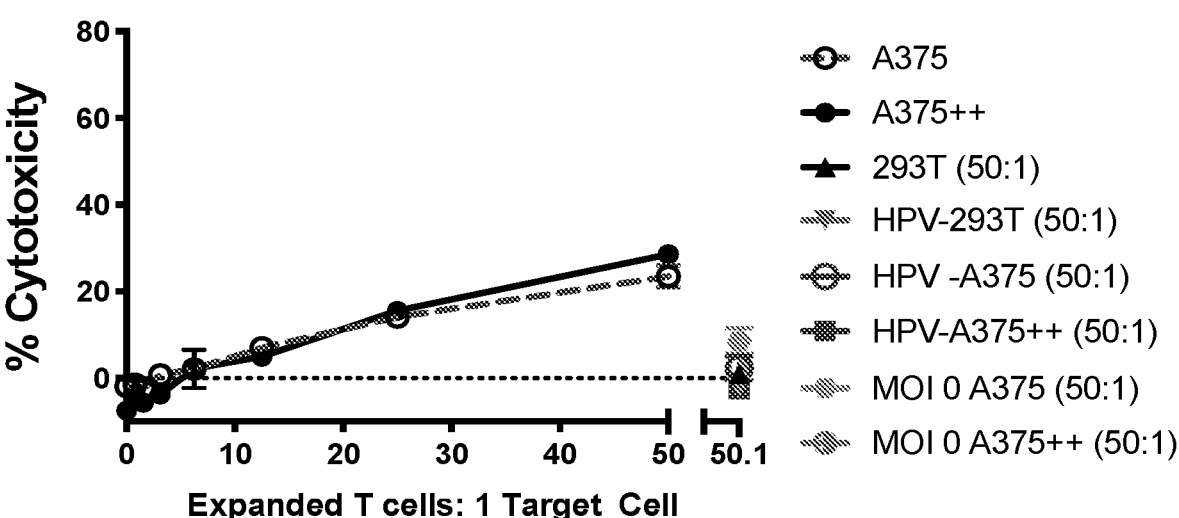
FIG. 2A and FIG. 2B.
Figure 2B:
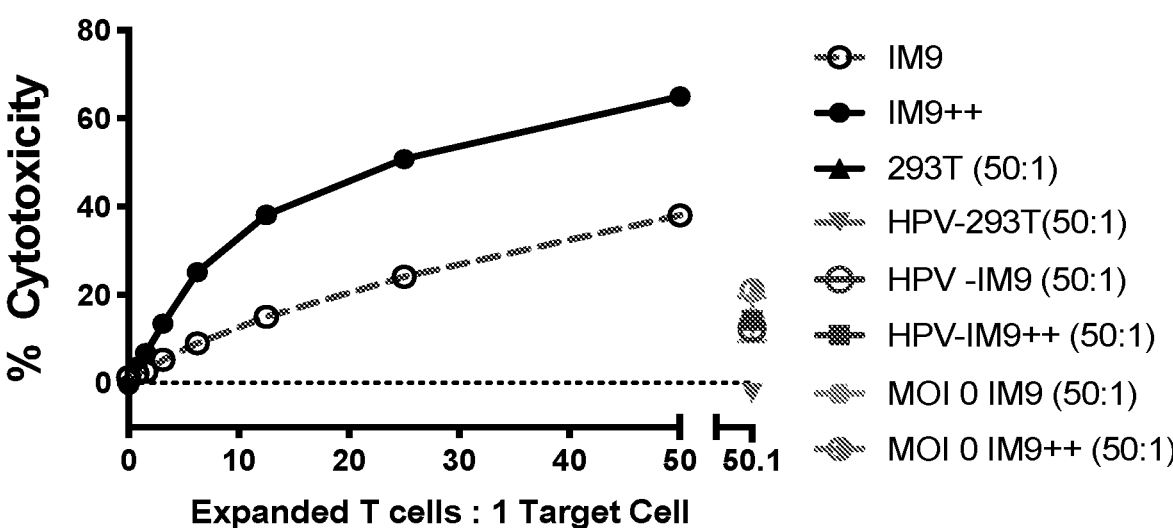

As shown in FIG. 2A and FIG. 2B and Tables 5, 6, and 7, cultures consisting of HLA-A2/MAGE-A4$_{286-294}$-targeted CAR+ T cells generated using the 31345 scFv induced A375 cells (FIG. 2A: open black circles, dashed line), A375 cells overexpressing HLA-A2/MAGE-A4$_{286-294}$ (FIG. 2A: closed black circles, solid line, denoted as A375++), IM9 cells (FIG. 2B: open black circles, dashed line), and IM9 cells overexpressing HLA-A2/MAGE-A4$_{286-294}$ (FIG. 2B: closed black circles, solid line, denoted as IM9++). Relative to A375 cells, a higher level of cytotoxicity was observed against endogenous IM9 cells. Overexpression of HLA-A2/MAGE-A4$_{286-294}$ in A375 cells did not boost the level of cytotoxicity relative to endogenous A375 cells. Without wishing to be bound by theory, this result may be because IM9 cells express higher levels of MAGE-A4 antigen than A375 cells.

TABLE 5

| HLA-A2/MAGE-A4$_{286-294}$-Directed CAR T Cell Cytolysis | | | | | | | | |
|---|---|---|---|---|---|---|---|---|
| CAR T cell: | Target cell | | | | | | | |
| Target | A375 | | A375++ | | IM9 | | IM9++ | |
| cell ratio | Mean | SD | mean | SD | mean | SD | Mean | SD |
| 50 | 23.5 | 2.6 | 28.6 | 1.1 | 38.0 | 0.5 | 64.9 | 0.6 |
| 25 | 14.1 | 0.4 | 15.5 | 1.1 | 24.1 | 1.4 | 50.8 | 0.7 |
| 12.5 | 7.0 | 1.6 | 4.9 | 1.4 | 15.0 | 2.1 | 38.1 | 1.0 |
| 6.25 | 2.1 | 1.2 | 2.2 | 4.4 | 9.0 | 1.3 | 25.2 | 0.1 |
| 3.125 | 0.8 | 0.7 | −3.7 | 0.8 | 5.3 | 1.5 | 13.4 | 1.4 |
| 1.5625 | −2.2 | 1.0 | −5.7 | 1.3 | 2.6 | 2.2 | 6.7 | 0.8 |
| 0.78125 | −1.4 | 1.0 | −3.2 | 2.5 | 2.1 | 2.0 | 3.7 | 0.3 |
| 0 | −1.9 | 0.9 | −7.5 | 1.1 | 1.3 | 1.3 | −0.5 | 0.1 |

SD: standard deviation

TABLE 6

| HLA-A2/MAGE-A4$_{286-294}$-Directed CAR T Cell Cytolysis, Plate 1 | | | | | | | | | | | |
|---|---|---|---|---|---|---|---|---|---|---|---|
| CAR T cell: | Target cell | | | | | | | | | | |
| Target | 293T | | HPV-293T | | HPV-A375 | | HPV-A375++ | | MOI 0 A375 | | MOI 0 A375++ |
| cell ratio | Mean | SD | Mean | SD | Mean | SD | Mean | SD | Mean | SD | Mean | SD |
| 50:1 | 0.9 | 1.7 | −2.1 | 1.6 | 2.3 | 2.8 | −2.6 | 1.2 | 8.6 | 2.9 | 2.8 | 1.7 |

SD: standard deviation

TABLE 7

| HLA-A2/MAGE-A4$_{286-294}$-Directed CAR T Cell Cytolysis, Plate 2 | | | | | | | | | | | |
|---|---|---|---|---|---|---|---|---|---|---|---|
| CAR T cell: | | | | | | | | | | | |
| Target | 293T | | HPV-293T | | HPV-IM9 | | HPV-A375++ | | MOI 0 A375 | | MOI 0 A375++ |
| cell ratio | Mean | SD | Mean | SD | Mean | SD | Mean | SD | Mean | SD | Mean | SD |
| 50:1 | 0.9 | 1.7 | −2.1 | 1.6 | 2.3 | 2.8 | −2.6 | 1.2 | 8.6 | 2.9 | 2.8 | 1.7 |

SD: standard deviation

As seen in Tables 5, 6, and 7, untransduced and expanded (MOI 0) T cells, as well as CAR T cells expressing a CAR that was not specific for MAGE-A4, when cocultured with MAGE-A4+ target cells (A375, A375++, IM9, IM9++) even at the maximum ratio of 50 T cells to one target cell, failed to elicit significant cytolysis of the target cells relative to MAGE-A4+ tumor cells. These results illustrated that cytolysis was only observed when the CAR structure contained the 31345 scFv recognizing HLA-A2/MAGE-$A4_{286-294}$. In addition, the HLA-A2/MAGE-$A4_{286-294}$ targeted CAR T cells demonstrated negligible cytotoxicity against 293T cells that lack MAGE-A4 expression, indicating that MAGE-A4 expression was required for cytolysis to be observed.

Example 6: MAGE-A4-Targeted CAR T Cells Reduce Growth of MAGE-A4-Expressing Tumors In Vivo in a Xenogenic Melanoma Model To determine the in vivo efficacy of HLA-A2/MAGE-$A4_{286-294}$-targeted chimeric antigen receptor (CAR) T cells, a xenogenic tumor study was performed in mice using A375 human melanoma tumor cells, which express MAGE-A4. On day 0, immunodeficient NOD.Cg-Prkdc$^{scid}$Il2rg$^{tm1Wjl}$/SzJ (NSG) mice were subcutaneously injected with $5\times10^6$ HLA-A2$^+$MAGE-A4$^+$ A375 human melanoma tumor cells. On day 10 of the experiment, after tumors had sufficient time to become establish, the mice were intravenously injected with $4\times10^6$ T cells that express either the control CAR (anti-HLA-A2/HPV16E7$_{11-19}$ scFv, in the VL-VH orientation) or an anti-HLA-A2/MAGE-$A4_{286-294}$ CAR (as determined by the frequency of cells expressing GFP, which is a marker for those cells that have been transduced with CAR). Specifically, the mice (n=5 per group) were administered either $4\times10^6$ irrelevant scFc CAR T cells (control scFv CAR) or $4\times10^6$ anti-MAGE-$A4_{286-294}$ CAR T encoding the 31345 scFv CAR. Tumor growth was assessed through day 52 by measuring tumor volumes.

In order to determine tumor volume by external caliper, the greatest longitudinal diameter (length in mm) and the greatest transverse diameter (width in mm) were determined. Tumor volumes based on caliper measurements were calculated by the formula: Volume $(mm^3)=(length\times width^2)/2$.

TABLE 8

HLA-A2/MAGE-$A4_{286-294}$-Directed
CAR T Cells Reduce Tumor Growth

| Day | CAR T Cell Treatment | Average Tumor Size $(mm^3)$ ± SEM |
|---|---|---|
| 10 | Control CAR T cells* Anti-HLA-A2/MAGE-$A4_{286-294}$ CAR T | 76.23 ± 11.63 84.37 ± 5.07 |
| 13 | Control CAR T cells* Anti-HLA-A2/MAGE-$A4_{286-294}$ CAR T | 133.48 ± 9.59 125.27 ± 9.15 |
| 17 | Control CAR T cells* Anti-HLA-A2/MAGE-$A4_{286-294}$ CAR T | 183.313 ± 22.76 121.785 ± 10.23 |
| 20 | Control CAR T cells* Anti-HLA-A2/MAGE-$A4_{286-294}$ CAR T | 464.89 ± 36.93407897 329.56 ± 47.42192007 |
| 24 | Control CAR T cells* Anti-HLA-A2/MAGE-$A4_{286-294}$ CAR T | 977.69 ± 51.55 171.98 ± 40.05 |
| 26 | Control CAR T cells* Anti-HLA-A2/MAGE-$A4_{286-294}$ CAR T | 1341.53 ± 116.36 53.83 ± 25.81 |

TABLE 8-continued

HLA-A2/MAGE-$A4_{286-294}$-Directed
CAR T Cells Reduce Tumor Growth

| Day | CAR T Cell Treatment | Average Tumor Size $(mm^3)$ ± SEM |
|---|---|---|
| 28 | Control CAR T cells* Anti-HLA-A2/MAGE-$A4_{286-294}$ CAR T | 1628.25 ± 97.27 0 ± 0 |
| 32 | Control CAR T cells* Anti-HLA-A2/MAGE-$A4_{286-294}$ CAR T | 2314.27 ± 147.13 0 ± 0 |
| 34 | Control CAR T cells* Anti-HLA-A2/MAGE-$A4_{286-294}$ CAR T | 2759.90 ± 190.94 0 ± 0 |
| 42 | Control CAR T cells* Anti-HLA-A2/MAGE-$A4_{286-294}$ CAR T | Animals Euthanized 0 ± 0 |
| 47 | Control CAR T cells* Anti-HLA-A2/MAGE-$A4_{286-294}$ CAR T | Animals Euthanized 0 ± 0 |
| 55 | Control CAR T cells* Anti-HLA-A2/MAGE-$A4_{286-294}$ CAR T | Animals Euthanized 0 ± 0 |

*Control CAR T cells expressed an anti-HLA-A2/HPV16E7(11-19) scFv CAR

TABLE 9

HLA-A2/MAGE-$A4_{286-294}$-Directed
CAR T Cells Promote Survival

| CAR T Cell Treatment | Number of Tumor-Free Mice (Day 34) |
|---|---|
| Control CAR T cells | 0 of 5 (all euthanized) |
| Anti-HLA-A2/MAGE-$A4_{286-294}$ CAR T cells | 5 of 5 |

Figure 3A:
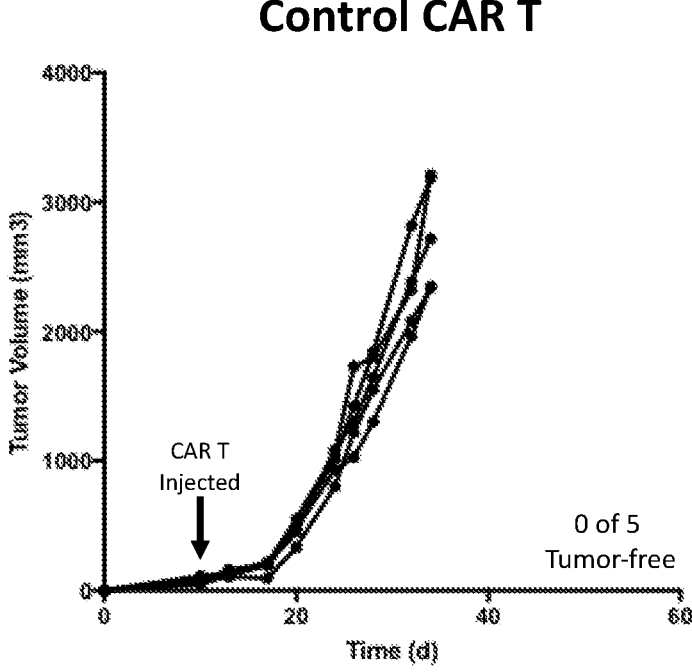
FIG. 3A and FIG. 3B.
Figure 3B:
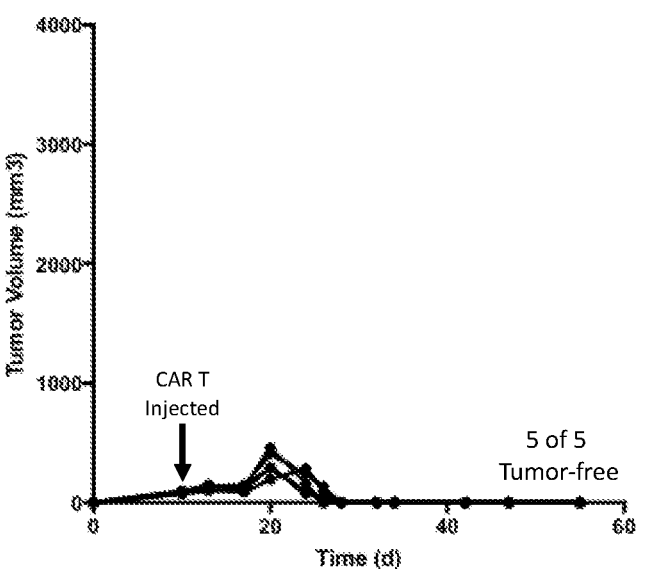

While the A375 tumors grew progressively in mice receiving irrelevant scFv CAR T cells, CAR T cells encoding the 31345 anti-HLA-A2/MAGE-$A4_{286-294}$ scFv CAR suppressed the growth of and subsequently eradicated established A375 tumors in vivo, as shown in Tables 8 and 9, and FIG. 3A and FIG. 3B.

Example 7: MAGE-A4-Targeted CAR T Cells Reduce Growth of MAGE-A4-Expressing Tumors In Vivo in a Xenogenic Multiple Myeloma Model To determine the in vivo efficacy of HLA-A2/MAGE-$A4_{286-294}$-targeted chimeric antigen receptor (CAR) T cells, a xenogenic tumor study was performed in mice using IM9 human multiple myeloma tumor cells, which express MAGE-A4. On day 0, immunodeficient NOD.Cg-Prkdc$^{scid}$Il2rg$^{tm1Wjl}$/SzJ (NSG) mice were subcutaneously injected with $5\times10^6$ HLA-A2$^+$MAGE-A4$^+$ IM9 human multiple myeloma tumor cells. On day 7 of the experiment, after tumors had sufficient time to become established, the mice were intravenously injected with $4\times10^6$ T cells that express either the control CAR (anti-HLA-A2/HPV16E7(11-19) scFv, in the VL-VH orientation) or an anti-HLA-A2/MAGE-$A4_{286-294}$ CAR (as determined by the frequency of cells expressing GFP, which is a marker for those cells that have been transduced with CAR). Specifically, the mice (n=5 per group) were administered either $4\times10^6$ irrelevant scFc CAR T cells (control scFv CAR) or $4\times10^6$ anti-MAGE-$A4_{286-294}$ CAR T encoding the 31345 scFv CAR. Tumor growth was assessed through day 52 by measuring tumor volumes.

In order to determine tumor volume by external caliper, the greatest longitudinal diameter (length in mm) and the greatest transverse diameter (width in mm) were determined. Tumor volumes based on caliper measurements were calculated by the formula: Volume $(mm^3)=(length \times width^2)/2$.

Table 10: HLA-A2/MAGE-A4$_{286-294}$-Directed CAR T Cells Reduce Tumor Growth

| Day | CAR T Cell Treatment | Average Tumor Size (mm³) ± SEM |
|---|---|---|
| 7 | Control CAR T cells* | 69.40 ± 15.45 |
| | Anti-HLA-A2/MAGE-A4$_{286-294}$ CAR T | 60.92 ± 3.61 |
| 10 | Control CAR T cells* | 168.68 ± 42.57 |
| | Anti-HLA-A2/MAGE-A4$_{286-294}$ CAR T | 176.45 ± 12.41 |
| 14 | Control CAR T cells* | 447.01 ± 75.34 |
| | Anti-HLA-A2/MAGE-A4$_{286-294}$ CAR T | 409.01 ± 83.91 |
| 17 | Control CAR T cells* | 1036.89 ± 194.01 |
| | Anti-HLA-A2/MAGE-A4$_{286-294}$ CAR T | 574.02 ±142.44 |
| 21 | Control CAR T cells* | 1838.18 ± 316.87 |
| | Anti-HLA-A2/MAGE-A4$_{286-294}$ CAR T | 884.57 ± 464.47 |
| 23 | Control CAR T cells* | 2043.35 ± 190.25 |
| | Anti-HLA-A2/MAGE-A4$_{286-294}$ CAR T | 1013.67 ± 585.48 |
| 25 | Control CAR T cells* | 3021.93 ± 153.39 |
| | Anti-HLA-A2/MAGE-A4$_{286-294}$ CAR T | 1474.85 ± 914.45 |
| 29 | Control CAR T cells* | Animals Euthanized |
| | Anti-HLA-A2/MAGE-A4$_{286-294}$ CAR T | 2282.63 ± 1418.51 |
| 31 | Control CAR T cells* | Animals Euthanized |
| | Anti-HLA-A2/MAGE-A4$_{286-294}$ CAR T | 2920.38 ± 1832.96 |
| 39 | Control CAR T cells* | Animals Euthanized |
| | Anti-HLA-A2/MAGE-A4$_{286-294}$ CAR T | 0.00 ± 0.00 |
| 44 | Control CAR T cells* | Animals Euthanized |
| | Anti-HLA-A2/MAGE-A4$_{286-294}$ CAR T | 0.00 ± 0.00 |
| 52 | Control CAR T cells* | Animals Euthanized |
| | Anti-HLA-A2/MAGE-A4$_{286-294}$ CAR T | 0.00 ± 0.00 |

*Control CAR T cells expressed an anti-HLA-A2/HPV16E7(11-19) scFv CAR

TABLE 11

HLA-A2/MAGE-A4$_{286-294}$-Directed CAR T Cells Promote Survival

| CAR T Cell Treatment | Number of Tumor-Free Mice (Day 34) |
|---|---|
| Control CAR T cells | 0 of 5 (all euthanized) |
| Anti-HLA-A2/MAGE-A4$_{286-294}$ CAR T cells | 3 of 5 |

Figure 4A:
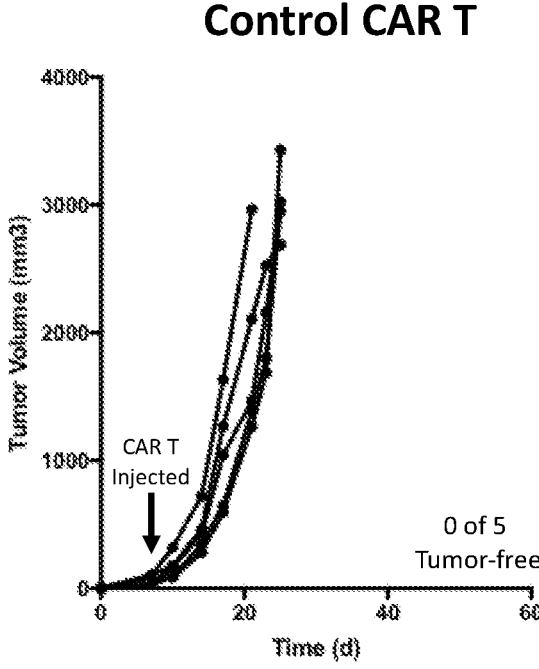
FIG. 4A and FIG. 4B.
Figure 4B:
Figure 4B:
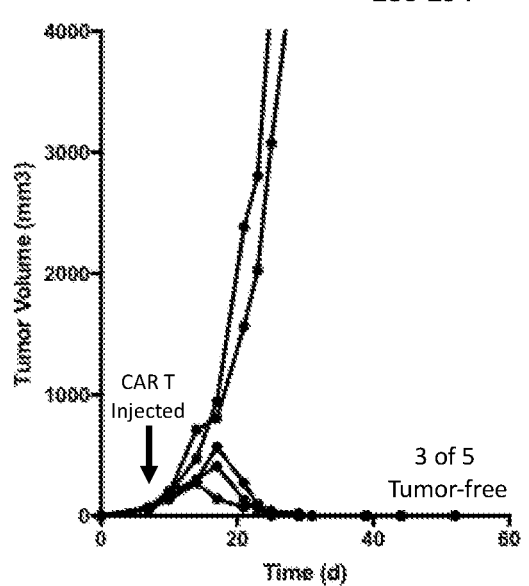

While the IM9 tumors grew progressively in mice receiving irrelevant scFv CAR T cells, CAR T cells encoding the 31345 anti-HLA-A2/MAGE-A4$_{286-294}$ scFv CAR suppressed the growth of and subsequently eradicated established IM9 tumors in 3 of the 5 mice in vivo, as shown in Tables 10 and 11, and FIG. 4A and FIG. 4B.

Example 8: MAGE-A4-Targeted CAR T Cells Reduce Growth of MAGE-A4-Expressing Tumors In Vivo in a Xenogenic A375 Melanoma Model Chimeric antigen receptors containing either an anti-HLA-A2/MAGEA4$_{286-294}$ scFv in the $V_L$-$V_H$ orientation plus either 1) a huCD8 hinge/transmembrane domain, a 4-1BB co-stimulatory domain, and a CD3z signaling domain (BB/z CAR), or 2) huCD28 hinge/transmembrane/costimulatory domains and a CD3z signaling domain (28/z CAR) were constructed using the $V_L$ and $V_H$ sequences of an anti-HLA-A2/MAGEA4$_{286-294}$ antibody, mAb31345. As a non-binding control, a BB/z CAR was designed using a scFv plus a huCD8 hinge/transmembrane domain, a 4-1BB co-stimulatory domain, and a CD3z signaling domain. These CARS were cloned into a pLVX lentiviral vector with an EF1a promoter and IRES:eGFP sequence (for tracking CAR-transduced cells), and VSV-pseudotyped lentivirus was produced.

CD3+ T cells were isolated from human peripheral blood mononuclear cells (PBMCs) from two normal donors ('Donor 1' and 'Donor 2'), stimulated with CD3/CD28 microbeads plus 100 U/ml recombinant human IL-2, and transduced with the lentivirus at an MOI=5. The transduced cells were expanded for 19 days with CD3/CD28 microbeads plus 100 U/ml recombinant human IL-2 before being cryopreserved until use during the in vivo experiment.

To determine the in vivo efficacy of HLA-A2/MAGEA4$_{286-294}$-targeted chimeric antigen receptor (CAR) T cells, a xenogenic tumor study was performed. On day 0, immunodeficient NOD.Cg-Prkdc$^{scid}$Il2rg$^{tm1 Wjl}$/SzJ (NSG) mice were subcutaneously injected with $5 \times 10^6$ HLA-A2$^+$ MAGEA4$^+$ A375 human melanoma tumor cells. Mass spectrometry techniques were used to determine that A375 melanoma cells express approximately 424 cell-surface copies of the MAGEA4$_{286-294}$ peptide. On day 13 after tumors were established, the mice (n=5 per group) were intravenously injected with $4 \times 10^6$ T cells that express either the non-binding control BB/z CAR (Control CAR T), the anti-HLA-A2/MAGEA4$_{286-294}$ BB/z CAR, or the anti-HLA-A2/MAGEA4$_{286-294}$ 28/z CAR (as determined by the frequency of cells expressing GFP, which is a marker for those cells that have been transduced with CAR) from two different donors. Tumor growth was assessed through day 64 by measuring tumor volumes.

In order to determine tumor volume by external caliper, the greatest longitudinal diameter (length in mm) and the greatest transverse diameter (width in mm) were determined. Tumor volumes based on caliper measurements were calculated by the formula: Volume $(mm^3)=(length \times width^2)/2$.

Donor 1: A375 tumors grew progressively in mice receiving either Control CAR T cells or MAGEA4$_{286-294}$ BB/z CAR T cells. By contrast, MAGEA4$_{286-294}$ 28/z suppressed the growth of established A375 tumors in vivo, with 1 of 5 mice tumor-free at day 64. Enhanced efficacy of MAGEA4$_{286-294}$ 28/z CAR vs. MAGEA4$_{286-294}$ BB/z CAR was confirmed, as tumor sizes on days 27, 29, 33, 36, 40 and 44 were statistically significant, with p<0.0001 by 2-way ANOVA test.

Donor 2: A375 tumors grew progressively in mice receiving Control CAR T cells. Treatment with both MAGEA4$_{286-294}$ BB/z and MAGEA4$_{286-294}$ 28/z CAR T cells suppressed A375 tumor growth, but with different kinetics. MAGEA4$_{286-294}$ 28/z CAR T cells acted with faster kinetics, eradicating tumors in 5 of 5 mice by day 27. MAGEA4$_{286-294}$ BB/z CAR T cells worked with slower kinetics, eradicating tumors in 4 of 5 mice by day 44. Enhanced kinetics of anti-tumor activity of MAGEA4$_{286-294}$ 28/z CAR vs. MAGEA4$_{286-294}$ BB/z CAR was confirmed, as tumor sizes on days 19 and 22 are statistically significant, with p=0.0071 and p=0.0008, respectively, by 2-way ANOVA test. Tables 12-27 provide a summary of these data.

TABLE 12

Summary of data, day 7

| CAR T Treatment | Average Tumor Size (mm$^3$) ± SEM on Day 7 | Number of mice still alive (of 5) on day 7 |
|---|---|---|
| Donor 1: Control CAR T | 76.5 ± 9.6 | 5 |
| Donor 1: MAGEA4$_{286-294}$ BB/z CAR T | 73.8 ± 4.0 | 5 |
| Donor 1: MAGEA4$_{286-294}$ 28/z CAR T | 89.9 ± 4.4 | 5 |
| Donor 2: Control CAR T | 102.8 ± .6 | 5 |
| Donor 2: MAGEA4$_{286-294}$ BB/z CAR T | 87.1 ± 9.7 | 5 |
| Donor 2: MAGEA4$_{286-294}$ 28/z CAR T | 83.7 ± 4.0 | 5 |

TABLE 13

Summary of data, day 12

| CAR T Treatment | Average Tumor Size (mm$^3$) ± SEM on Day 12 | Number of mice still alive (of 5) on day 12 |
|---|---|---|
| Donor 1: Control CAR T | 152.1 ± 27.7 | 5 |
| Donor 1: MAGEA4$_{286-294}$ BB/z CAR T | 131.2 ± 22.1 | 5 |
| Donor 1: MAGEA4$_{286-294}$ 28/z CAR T | 153.0 ± 7.0 | 5 |
| Donor 2: Control CAR T | 177.1 ± 26.4 | 5 |
| Donor 2: MAGEA4$_{286-294}$ BB/z CAR T | 154.9 ± 7.3 | 5 |
| Donor 2: MAGEA4$_{286-294}$ 28/z CAR T | 117.2 ± 9.3 | 5 |

TABLE 14

Summary of data, day 15

| CAR T Treatment | Average Tumor Size (mm$^3$) ± SEM on Day 15 | Number of mice still alive (of 5) on day 15 |
|---|---|---|
| Donor 1: Control CAR T | 311.7 ± 61.7 | 5 |
| Donor 1: MAGEA4$_{286-294}$ BB/z CAR T | 308.8 ± 33.2 | 5 |
| Donor 1: MAGEA4$_{286-294}$ 28/z CAR T | 337.9 ± 16.5 | 5 |
| Donor 2: Control CAR T | 443.5 ± 56.9 | 5 |
| Donor 2: MAGEA4$_{286-294}$ BB/z CAR T | 343.2 ± 41.2 | 5 |
| Donor 2: MAGEA4$_{286-294}$ 28/z CAR T | 247.2 ± 42.3 | 5 |

TABLE 15

Summary of data, day 16

| CAR T Treatment | Average Tumor Size (mm$^3$) ± SEM on Day 16 | Number of mice still alive (of 5) on day 16 |
|---|---|---|
| Donor 1: Control CAR T | 336.2 ± 60.9 | 5 |
| Donor 1: MAGEA4$_{286-294}$ BB/z CAR T | 402.6 ± 35.7 | 5 |

TABLE 15-continued

Summary of data, day 16

| CAR T Treatment | Average Tumor Size (mm$^3$) ± SEM on Day 16 | Number of mice still alive (of 5) on day 16 |
|---|---|---|
| Donor 1: MAGEA4$_{286-294}$ 28/z CAR T | 440.6 ± 36.4 | 5 |
| Donor 2: Control CAR T | 541.7 ± 62.6 | 5 |
| Donor 2: MAGEA4$_{286-294}$ BB/z CAR T | 409.9 ± 40.7 | 5 |
| Donor 2: MAGEA4$_{286-294}$ 28/z CAR T | 212.8 ± 33.8 | 5 |

TABLE 16

Summary of data, day 19

| CAR T Treatment | Average Tumor Size (mm$^3$) ± SEM on Day 19 | Number of mice still alive (of 5) on day 19 |
|---|---|---|
| Donor 1: Control CAR T | 731.6 ± 103.9 | 5 |
| Donor 1: MAGEA4$_{286-294}$ BB/z CAR T | 755.6 ± 92.2 | 5 |
| Donor 1: MAGEA4$_{286-294}$ 28/z CAR T | 769.7 ± 86.6 | 5 |
| Donor 2: Control CAR T | 1136.3 ± 122.1 | 5 |
| Donor 2: MAGEA4$_{286-294}$ BB/z CAR T | 603.9 ± 36.8 | 5 |
| Donor 2: MAGEA4$_{286-294}$ 28/z CAR T | 98.4 ± 15.6 | 5 |

TABLE 17

Summary of data, day 22

| CAR T Treatment | Average Tumor Size (mm$^3$) ± SEM on Day 22 | Number of mice still alive (of 5) on day 22 |
|---|---|---|
| Donor 1: Control CAR T | 1021.3 ± 138.5 | 5 |
| Donor 1: MAGEA4$_{286-294}$ BB/z CAR T | 1027.8 ± 111.5 | 5 |
| Donor 1: MAGEA4$_{286-294}$ 28/z CAR T | 785.7 ± 97.4 | 5 |
| Donor 2: Control CAR T | 1725.9 ± 216.2 | 5 |
| Donor 2: MAGEA4$_{286-294}$ BB/z CAR T | 641.5 ± 119.9 | 5 |
| Donor 2: MAGEA4$_{286-294}$ 28/z CAR T | 30.2 ± 13.0 | 5 |

TABLE 18

Summary of data, day 27

| CAR T Treatment | Average Tumor Size (mm$^3$) ± SEM on Day 27 | Number of mice still alive (of 5) on day 27 |
|---|---|---|
| Donor 1: Control CAR T | 1983.6 ± 187.3 | 5 |
| Donor 1: MAGEA4$_{286-294}$ BB/z CAR T | 1759.7 ± 247.6 | 5 |
| Donor 1: MAGEA4$_{286-294}$ 28/z CAR T | 347.9 ± 54.2 | 5 |
| Donor 2: Control CAR T | 2806.0 ± 222.7 | 5 |

TABLE 18-continued

| | Summary of data, day 27 | |
| --- | --- | --- |
| CAR T Treatment | Average Tumor Size (mm$^3$) ± SEM on Day 27 | Number of mice still alive (of 5) on day 27 |
| Donor 2: MAGEA4$_{286-294}$ BB/z CAR T | 258.2 ± 50.5 | 5 |
| Donor 2: MAGEA4$_{286-294}$ 28/z CAR T | 0.0 ± 0.0 | 5 |

TABLE 19

| | Summary of data, day 29 | |
| --- | --- | --- |
| CAR T Treatment | Average Tumor Size (mm$^3$) ± SEM on Day 29 | Number of mice still alive (of 5) on day 29 |
| Donor 1: Control CAR T | 2503.7 ± 169.4 | 5 |
| Donor 1: MAGEA4$_{286-294}$ BB/z CAR T | 1941.9 ± 252.1 | 5 |
| Donor 1: MAGEA4$_{286-294}$ 28/z CAR T | 270.3 ± 49.9 | 5 |
| Donor 2: Control CAR T | 3387.0 ± 154.8 | 5 |
| Donor 2: MAGEA4$_{286-294}$ BB/z CAR T | 203.6 ± 123.4 | 5 |
| Donor 2: MAGEA4$_{286-294}$ 28/z CAR T | 0.0 ± 0.0 | 5 |

TABLE 20

| | Summary of data, day 33 | |
| --- | --- | --- |
| CAR T Treatment | Average Tumor Size (mm$^3$) ± SEM on Day 33 | Number of mice still alive (of 5) on day 33 |
| Donor 1: Control CAR T | Animals Euthanized | 0 |
| Donor 1: MAGEA4$_{286-294}$ BB/z CAR T | 2201.9 ± 321.9 | 5 |
| Donor 1: MAGEA4$_{286-294}$ 28/z CAR T | 202.7 ± 70.7 | 5 |
| Donor 2: Control CAR T | Animals Euthanized | 0 |
| Donor 2: MAGEA4$_{286-294}$ BB/z CAR T | 106.2 ± 80.5 | 5 |
| Donor 2: MAGEA4$_{286-294}$ 28/z CAR T | 0.0 ± 0.0 | 5 |

TABLE 21

| | Summary of data, day 36 | |
| --- | --- | --- |
| CAR T Treatment | Average Tumor Size (mm$^3$) ± SEM on Day 40 | Number of mice still alive (of 5) on day 36 |
| Donor 1: Control CAR T | Animals Euthanized | 0 |
| Donor 1: MAGEA4$_{286-294}$ BB/z CAR T | 2171.2 ± 286.1 | 5 |
| Donor 1: MAGEA4$_{286-294}$ 28/z CAR T | 230.9 ± 106.4 | 5 |
| Donor 2: Control CAR T | Animals Euthanized | 0 |

TABLE 21-continued

| | Summary of data, day 36 | |
| --- | --- | --- |
| CAR T Treatment | Average Tumor Size (mm$^3$) ± SEM on Day 40 | Number of mice still alive (of 5) on day 36 |
| Donor 2: MAGEA4$_{286-294}$ BB/z CAR T | 97.1 ± 83.8 | 5 |
| Donor 2: MAGEA4$_{286-294}$ 28/z CAR T | 0.0 ± 0.0 | 5 |

TABLE 22

| | Summary of data, day 40 | |
| --- | --- | --- |
| CAR T Treatment | Average Tumor Size (mm$^3$) ± SEM on Day 40 | Number of mice still alive (of 5) on day 40 |
| Donor 1: Control CAR T | Animals Euthanized | 0 |
| Donor 1: MAGEA4$_{286-294}$ BB/z CAR T | 2431.9 ± 359.6 | |
| Donor 1: MAGEA4$_{286-294}$ 28/z CAR T | 443.9 ± 175.3 | |
| Donor 2: Control CAR T | Animals Euthanized | 0 |
| Donor 2: MAGEA4$_{286-294}$ BB/z CAR T | 205.7 ± 193.7 | |
| Donor 2: MAGEA4$_{286-294}$ 28/z CAR T | 0.0 ± 0.0 | 5 |

TABLE 23

| | Summary of data, day 44 | |
| --- | --- | --- |
| CAR T Treatment | Average Tumor Size (mm$^3$) ± SEM on Day 44 | Number of mice still alive (of 5) on day 44 |
| Donor 1: Control CAR T | Animals Euthanized | 0 |
| Donor 1: MAGEA4$_{286-294}$ BB/z CAR T | 2892.7 ± 432.7 | 5 |
| Donor 1: MAGEA4$_{286-294}$ 28/z CAR T | 416.7 ± 195.0 | 5 |
| Donor 2: Control CAR T | Animals Euthanized | 0 |
| Donor 2: MAGEA4$_{286-294}$ BB/z CAR T | 166.0 ± 166.0 | 5 |
| Donor 2: MAGEA4$_{286-294}$ 28/z CAR T | 0.0 ± 0.0 | 5 |

TABLE 24

| | Summary of data, day 48 | |
| --- | --- | --- |
| CAR T Treatment | Average Tumor Size (mm$^3$) ± SEM on Day 48 | Number of mice still alive (of 5) on day 48 |
| Donor 1: Control CAR T | Animals Euthanized | 0 |
| Donor 1: MAGEA4$_{286-294}$ BB/z CAR T | 3266.4 ± 1026.4 | 2 |
| Donor 1: MAGEA4$_{286-294}$ 28/z CAR T | 749.7 ± 364.4 | 5 |
| Donor 2: Control CAR T | Animals Euthanized | 0 |
| Donor 2: MAGEA4$_{286-294}$ BB/z CAR T | 292.0 ± 292.0 | 5 |
| Donor 2: MAGEA4$_{286-294}$ 28/z CAR T | 0.0 ± 0.0 | 5 |

TABLE 25

Summary of data, day 50

| CAR T Treatment | Average Tumor Size (mm$^3$) ± SEM on Day 50 | Number of mice still alive (of 5) on day 50 |
|---|---|---|
| Donor 1: Control CAR T | Animals Euthanized | 0 |
| Donor 1: MAGEA4$_{286-294}$ BB/z CAR T | 2835.7 ± 0.0 | 1 |
| Donor 1: MAGEA4$_{286-294}$ 28/z CAR T | 955.8 ± 367.2 | 5 |
| Donor 2: Control CAR T | Animals Euthanized | 0 |
| Donor 2: MAGEA4$_{286-294}$ BB/z CAR T | 349.0 ± 349.0 | 5 |
| Donor 2: MAGEA4$_{286-294}$ 28/z CAR T | 0.0 ± 0.0 | 5 |

TABLE 26

Summary of data, day 57

| CAR T Treatment | Average Tumor Size (mm$^3$) ± SEM on Day 57 | Number of mice still alive (of 5) on day 57 |
|---|---|---|
| Donor 1: Control CAR T | Animals Euthanized | 0 |
| Donor 1: MAGEA4$_{286-294}$ BB/z CAR T | Animals Euthanized | 0 |
| Donor 1: MAGEA4$_{286-294}$ 28/z CAR T | 1311.0 ± 660.5 | 3 |
| Donor 2: Control CAR T | Animals Euthanized | 0 |
| Donor 2: MAGEA4$_{286-294}$ BB/z CAR T | 0.0 ± 0.0 | 4 |
| Donor 2: MAGEA4$_{286-294}$ 28/z CAR T | 0.0 ± 0.0 | 5 |

TABLE 27

Summary of data, day 64

| CAR T Treatment | Average Tumor Size (mm$^3$) ± SEM on Day 64 | Number of mice still alive (of 5) on day 64 |
|---|---|---|
| Donor 1: Control CAR T | Animals Euthanized | 0 |
| Donor 1: MAGEA4$_{286-294}$ BB/z CAR T | Animals Euthanized | 0 |
| Donor 1: MAGEA4$_{286-294}$ 28/z CAR T | 1973.0 ± 990.8 | 3 |
| Donor 2: Control CAR T | Animals Euthanized | 0 |
| Donor 2: MAGEA4$_{286-294}$ BB/z CAR T | 0.0 ± 0.0 | 4 |
| Donor 2: MAGEA4$_{286-294}$ 28/z CAR T | 0.0 ± 0.0 | 5 |

These results demonstrate that MAGE-A4-specific CARs of the present disclosure have potent anti-tumor effects in vivo.

Example 9: MAGE-A4-Targeted CAR T Cells Reduce Growth of MAGE-A4-Expressing Tumors In Vivo in a Xenogenic SK-MEL-37 Melanoma Model Chimeric antigen receptors containing either an anti-HLA-A2/MAGEA4$_{286-294}$ scFv in the $V_L$-$V_H$ orientation plus either 1) a huCD8 hinge/transmembrane domain, a 4-1BB co-stimulatory domain, and a CD3z signaling domain (BB/z CAR), or 2) huCD28 hinge/transmembrane/costimulatory domains and a CD3z signaling domain (28/z CAR) were constructed using the $V_L$ and $V_H$ sequences of an anti-HLA-A2/MAGEA4$_{286-294}$ antibody, mAb31345. As a non-binding control, a BB/z CAR was designed using a different scFv plus a huCD8 hinge/transmembrane domain, a 4-1BB co-stimulatory domain, and a CD3z signaling domain. These CARs were cloned into a pLVX lentiviral vector with an EF1a promoter and IRES:eGFP sequence (for tracking CAR-transduced cells), and VSV-pseudotyped lentivirus was produced.

CD3+ T cells were isolated from human peripheral blood mononuclear cells (PBMCs) from two normal donors ('Donor 1' and 'Donor 2'), stimulated with CD3/CD28 microbeads plus 100 U/ml recombinant human IL-2, and transduced with the lentivirus at an MOI=5. The transduced cells were expanded for 19 days with CD3/CD28 microbeads plus 100 U/ml recombinant human IL-2 before being cryopreserved until use during the in vivo experiment.

To determine the in vivo efficacy of HLA-A2/MAGEA4$_{286-294}$-targeted chimeric antigen receptor (CAR) T cells, a xenogenic tumor study was performed. On day 0, immunodeficient NOD.Cg-Prkdc$^{scid}$Il2rg$^{tm1 Wjl}$/SzJ (NSG) mice were subcutaneously injected with 5×10$^6$ HLA-A2$^+$ MAGEA4$^+$ SK-MEL-37 human melanoma tumor cells. Mass spectrometry techniques were used to determined that SK-MEL-37 melanoma cells express approximately 1,326 cell-surface copies of the MAGEA4$_{286-294}$ peptide. On day 7 after tumors were established, the mice (n=5 per group) were intravenously injected with 4×10$^6$ T cells that express either the non-binding control BB/z CAR (Control CAR T), the anti-HLA-A2/MAGEA4$_{286-294}$ BB/z CAR, or the anti-HLA-A2/MAGEA4$_{286-294}$ 28/z CAR (as determined by the frequency of cells expressing GFP, which is a marker for those cells that have been transduced with CAR) from two different donors. Tumor growth was assessed through day 64 by measuring tumor volumes.

To determine tumor volume by external caliper, the greatest longitudinal diameter (length in mm) and the greatest transverse diameter (width in mm) were determined. Tumor volumes based on caliper measurements were calculated by the formula: Volume (mm$^3$)=(length×width$^2$)/2.

TABLE 28

Summary of CARs

| Parental mAb # | Specificity | Description |
|---|---|---|
| N/A | Non-binding control | Anti-HLA-A2/HPV16E7$_{11-19}$ scFv 17363in VL-VH orientation with huCD8 hinge/transmembrane domain, a 4-1BB co-stimulatory domain, and a CD3z signaling domain (Control CAR) |
| 31345 | HLA-A2/ MAGEA4$_{286-294}$ | Anti-MAGEA4$_{286-294}$ scFv 31345 in VL-VH orientation with huCD8 hinge/transmembrane domain, a 4-1BB co-stimulatory domain, and a CD3z signaling domain (BB/z CAR) |
| 31345 | HLA-A2/ MAGEA4$_{286-294}$ | Anti-MAGEA4$_{286-294}$ scFv 31345 in VL-VH orientation with huCD28 hinge/transmembrane/costimulatory domains and a CD3z signaling domain (28/z CAR) |

Donor 1: SK-MEL-37 tumors grew progressively in mice receiving either Control CAR T cells or MAGEA4$_{286-294}$ BB/z CAR T cells. By contrast, MAGEA4$_{286-294}$ 28/z suppressed the growth of established SK-MEL-37 tumors in vivo. The efficacy of $MAGEA4_{286-294}$ 28/z CAR vs. $MAGEA4_{286-294}$ BB/z CAR was observed from tumor sizes on days 31, 35, 40, 47, 55, and 62, which are statistically significant, with $p<0.0001$ by 2-way ANOVA test.

Donor 2: SK-MEL-37 tumors grew progressively in mice receiving Control CAR T cells. Treatment with $MAGEA4_{286-294}$ BB/z CAR T cells demonstrated efficacy and delayed tumor growth by approximately one week, and $MAGEA4_{286-294}$ 28/z CAR T cells strongly suppressed SK-MEL-37 tumor growth, bringing tumors to undetectable (unpalpable) levels in 5 of 5 mice by day 20. These tumors remained undetectable through days 62-69, upon which time tumors recurred.

Collectively, the results demonstrate that the MAGE-A4 specific CARs of the present disclosure demonstrate in vivo anti-tumor activity and anti-tumor kinetics (Tables 29-45).

TABLE 29

| | Summary of data, day 6 | |
|---|---|---|
| CAR T Treatment | Average Tumor Size $(mm^3) \pm$ SEM on Day 6 | Number of mice still alive (of 5) on day 6 |
| Donor 1: Control CAR T | 80.6 ± 4.2 | 5 |
| Donor 1: $MAGEA4_{286-294}$ BB/z CAR T | 109.4 ± 14.6 | 5 |
| Donor 1: $MAGEA4_{286-294}$ 28/z CAR T | 115.3 ± 7.0 | 5 |
| Donor 2: Control CAR T | 92.6 ± 12.4 | 5 |
| Donor 2: $MAGEA4_{286-294}$ BB/z CAR T | 115.4 ± 16.7 | 5 |
| Donor 2: $MAGEA4_{286-294}$ 28/z CAR T | 112.8 ± 5.5 | 5 |

TABLE 30

| | Summary of data, day 11 | |
|---|---|---|
| CAR T Treatment | Average Tumor Size $(mm^3) \pm$ SEM on Day 11 | Number of mice still alive (of 5) on day 11 |
| Donor 1: Control CAR T | 104.0 ± 9.4 | 5 |
| Donor 1: $MAGEA4_{286-294}$ BB/z CAR T | 133.5 ± 21.1 | 5 |
| Donor 1: $MAGEA4_{286-294}$ 28/z CAR T | 120.8 ± 22.0 | 5 |
| Donor 2: Control CAR T | 87.7 ± 10.6 | 5 |
| Donor 2: $MAGEA4_{286-294}$ BB/z CAR T | 97.3 ± 12.9 | 5 |
| Donor 2: $MAGEA4_{286-294}$ 28/z CAR T | 136.9 ± 23.3 | 5 |

TABLE 31

| | Summary of data, day 13 | |
|---|---|---|
| CAR T Treatment | Average Tumor Size $(mm^3) \pm$ SEM on Day 13 | Number of mice still alive (of 5) on day 13 |
| Donor 1: Control CAR T | 142.2 ± 9.0 | 5 |
| Donor 1: $MAGEA4_{286-294}$ BB/z CAR T | 133.7 ± 20.1 | 5 |
| Donor 1: $MAGEA4_{286-294}$ 28/z CAR T | 106.4 ± 17.0 | 5 |

TABLE 31-continued

| | Summary of data, day 13 | |
|---|---|---|
| CAR T Treatment | Average Tumor Size $(mm^3) \pm$ SEM on Day 13 | Number of mice still alive (of 5) on day 13 |
| Donor 2: Control CAR T | 106.4 ± 14.7 | 5 |
| Donor 2: $MAGEA4_{286-294}$ BB/z CAR T | 83.5 ± 16.4 | 5 |
| Donor 2: $MAGEA4_{286-294}$ 28/z CAR T | 72.7 ± 14.8 | 5 |

TABLE 32

| | Summary of data, day 18 | |
|---|---|---|
| CAR T Treatment | Average Tumor Size $(mm^3) \pm$ SEM on Day 18 | Number of mice still alive (of 5) on day 18 |
| Donor 1: Control CAR T | 181.3 ± 24.4 | 5 |
| Donor 1: $MAGEA4_{286-294}$ BB/z CAR T | 171.3 ± 29.3 | 5 |
| Donor 1: $MAGEA4_{286-294}$ 28/z CAR T | 63.7 ± 6.8 | 5 |
| Donor 2: Control CAR T | 139.8 ± 17.6 | 5 |
| Donor 2: $MAGEA4_{286-294}$ BB/z CAR T | 70.7 ± 6.6 | 5 |
| Donor 2: $MAGEA4_{286-294}$ 28/z CAR T | 14.1 ± 6.5 | 5 |

TABLE 33

| | Summary of data, day 20 | |
|---|---|---|
| CAR T Treatment | Average Tumor Size $(mm^3) \pm$ SEM on Day 20 | Number of mice still alive (of 5) on day 20 |
| Donor 1: Control CAR T | 202.7 ± 16.5 | 5 |
| Donor 1: $MAGEA4_{286-294}$ BB/z CAR T | 194.5 ± 33.0 | 5 |
| Donor 1: $MAGEA4_{286-294}$ 28/z CAR T | 70.0 ± 15.6 | 5 |
| Donor 2: Control CAR T | 174.3 ± 33.7 | 5 |
| Donor 2: $MAGEA4_{286-294}$ BB/z CAR T | 79.4 ± 11.0 | 5 |
| Donor 2: $MAGEA4_{286-294}$ 28/z CAR T | 0.0 ± 0.0 | 5 |

TABLE 34

| | Summary of data, day 24 | |
|---|---|---|
| CAR T Treatment | Average Tumor Size $(mm^3) \pm$ SEM on Day 24 | Number of mice still alive (of 5) on day 24 |
| Donor 1: Control CAR T | 312.5 ± 35.3 | 5 |
| Donor 1: $MAGEA4_{286-294}$ BB/z CAR T | 272.3 ± 66.8 | 5 |
| Donor 1: $MAGEA4_{286-294}$ 28/z CAR T | 52.9 ± 12.2 | 5 |
| Donor 2: Control CAR T | 237.3 ± 37.7 | 5 |
| Donor 2: $MAGEA4_{286-294}$ BB/z CAR T | 78.2 ± 11.2 | 5 |

TABLE 34-continued

| | Summary of data, day 24 | |
| CAR T Treatment | Average Tumor Size (mm$^3$) ± SEM on Day 24 | Number of mice still alive (of 5) on day 24 |
| --- | --- | --- |
| Donor 2: MAGEA4$_{286-294}$ 28/z CAR T | 0.0 ± 0.0 | 5 |

TABLE 35

| | Summary of data, day 27 | |
| CAR T Treatment | Average Tumor Size (mm$^3$) ± SEM on Day 27 | Number of mice still alive (of 5) on day 27 |
| --- | --- | --- |
| Donor 1: Control CAR T | 396.5 ± 44.7 | 5 |
| Donor 1: MAGEA4$_{286-294}$ BB/z CAR T | 328.0 ± 60.3 | 5 |
| Donor 1: MAGEA4$_{286-294}$ 28/z CAR T | 49.9 ± 16.1 | 5 |
| Donor 2: Control CAR T | 371.0 ± 54.6 | 5 |
| Donor 2: MAGEA4$_{286-294}$ BB/z CAR T | 100.0 ± 15.9 | 5 |
| Donor 2: MAGEA4$_{286-294}$ 28/z CAR T | 0.0 ± 0.0 | 5 |

TABLE 36

| | Summary of data, day 31 | |
| CAR T Treatment | Average Tumor Size (mm$^3$) ± SEM on Day 31 | Number of mice still alive (of 5) on day 31 |
| --- | --- | --- |
| Donor 1: Control CAR T | 635.0 ± 73.7 | 5 |
| Donor 1: MAGEA4$_{286-294}$ BB/z CAR T | 610.4 ± 116.4 | 5 |
| Donor 1: MAGEA4$_{286-294}$ 28/z CAR T | 50.5 ± 11.8 | 5 |
| Donor 2: Control CAR T | 512.6 ± 54.2 | 5 |
| Donor 2: MAGEA4$_{286-294}$ BB/z CAR T | 158.0 ± 17.2 | 5 |
| Donor 2: MAGEA4$_{286-294}$ 28/z CAR T | 0.0 ± 0.0 | 5 |

TABLE 37

| | Summary of data, day 35 | |
| CAR T Treatment | Average Tumor Size (mm$^3$) ± SEM on Day 35 | Number of mice still alive (of 5) on day 35 |
| --- | --- | --- |
| Donor 1: Control CAR T | 796.8 ± 132.7 | 5 |
| Donor 1: MAGEA4$_{286-294}$ BB/z CAR T | 803.1 ± 166.7 | 5 |
| Donor 1: MAGEA4$_{286-294}$ 28/z CAR T | 52.6 ± 19.8 | 5 |
| Donor 2: Control CAR T | 724.1 ± 85.7 | 5 |
| Donor 2: MAGEA4$_{286-294}$ BB/z CAR T | 325.4 ± 61.1 | 5 |
| Donor 2: MAGEA4$_{286-294}$ 28/z CAR T | 0.0 ± 0.0 | 5 |

TABLE 38

| | Summary of data, day 40 | |
| CAR T Treatment | Average Tumor Size (mm$^3$) ± SEM on Day 40 | Number of mice still alive (of 5) on day 40 |
| --- | --- | --- |
| Donor 1: Control CAR T | 986.3 ± 136.1 | 5 |
| Donor 1: MAGEA4$_{286-294}$ BB/z CAR T | 1067.8 ± 152.5 | 5 |
| Donor 1: MAGEA4$_{286-294}$ 28/z CAR T | 62.2 ± 28.2 | 5 |
| Donor 2: Control CAR T | 778.5 ± 69.8 | 5 |
| Donor 2: MAGEA4$_{286-294}$ BB/z CAR T | 446.5 ± 71.1 | 5 |
| Donor 2: MAGEA4$_{286-294}$ 28/z CAR T | 0.0 ± 0.0 | 5 |

TABLE 39

| | Summary of data, day 47 | |
| CAR T Treatment | Average Tumor Size (mm$^3$) ± SEM on Day 47 | Number of mice still alive (of 5) on day 47 |
| --- | --- | --- |
| Donor 1: Control CAR T | 1414.9 ± 311.2 | 5 |
| Donor 1: MAGEA4$_{286-294}$ BB/z CAR T | 1205.2 ± 193.7 | 5 |
| Donor 1: MAGEA4$_{286-294}$ 28/z CAR T | 80.5 ± 42.3 | 5 |
| Donor 2: Control CAR T | 804.6 ± 85.8 | 5 |
| Donor 2: MAGEA4$_{286-294}$ BB/z CAR T | 496.7 ± 57.6 | 5 |
| Donor 2: MAGEA4$_{286-294}$ 28/z CAR T | 0.0 ± 0.0 | 5 |

TABLE 40

| | Summary of data, day 55 | |
| CAR T Treatment | Average Tumor Size (mm$^3$) ± SEM on Day 55 | Number of mice still alive (of 5) on day 55 |
| --- | --- | --- |
| Donor 1: Control CAR T | Animals Euthanized | 0 |
| Donor 1: MAGEA4$_{286-294}$ BB/z CAR T | Animals Euthanized | 0 |
| Donor 1: MAGEA4$_{286-294}$ 28/z CAR T | 175.9 ± 76.5 | 5 |
| Donor 2: Control CAR T | Animals Euthanized | 0 |
| Donor 2: MAGEA4$_{286-294}$ BB/z CAR T | 823.1 ± 85.8 | 5 |
| Donor 2: MAGEA4$_{286-294}$ 28/z CAR T | 0.0 ± 0.0 | 5 |

TABLE 41

| | Summary of data, day 62 | |
| CAR T Treatment | Average Tumor Size (mm$^3$) ± SEM on Day 62 | Number of mice still alive (of 5) on day 62 |
| --- | --- | --- |
| Donor 1: Control CAR T | Animals Euthanized | 0 |
| Donor 1: MAGEA4$_{286-294}$ BB/z CAR T | Animals Euthanized | 0 |
| Donor 1: MAGEA4$_{286-294}$ 28/z CAR T | 298.0 ± 110.8 | 5 |

TABLE 41-continued

| | Summary of data, day 62 | |
| --- | --- | --- |
| CAR T Treatment | Average Tumor Size (mm³) ± SEM on Day 62 | Number of mice still alive (of 5) on day 62 |
| Donor 2: Control CAR T | Animals Euthanized | 0 |
| Donor 2: MAGEA4₂₈₆₋₂₉₄ BB/z CAR T | 1048.0 ± 124.3 | 5 |
| Donor 2: MAGEA4₂₈₆₋₂₉₄ 28/z CAR T | 0.0 ± 0.0 | 5 |

TABLE 42

| | Summary of data, day 69 | |
| --- | --- | --- |
| CAR T Treatment | Average Tumor Size (mm³) ± SEM on Day 69 | Number of mice still alive (of 5) on day 69 |
| Donor 1: Control CAR T | Animals Euthanized | 0 |
| Donor 1: MAGEA4₂₈₆₋₂₉₄ BB/z CAR T | Animals Euthanized | 0 |
| Donor 1: MAGEA4₂₈₆₋₂₉₄ 28/z CAR T | 533.3 ± 166.8 | 5 |
| Donor 2: Control CAR T | Animals Euthanized | 0 |
| Donor 2: MAGEA4₂₈₆₋₂₉₄ BB/z CAR T | Animals Euthanized | 0 |
| Donor 2: MAGEA4₂₈₆₋₂₉₄ 28/z CAR T | 7.3 ± 5.6 | 5 |

TABLE 43

| | Summary of data, day 77 | |
| --- | --- | --- |
| CAR T Treatment | Average Tumor Size (mm³) ± SEM on Day 77 | Number of mice still alive (of 5) on day 77 |
| Donor 1: Control CAR T | Animals Euthanized | 0 |
| Donor 1: MAGEA4₂₈₆₋₂₉₄ BB/z CAR T | Animals Euthanized | 0 |
| Donor 1: MAGEA4₂₈₆₋₂₉₄ 28/z CAR T | 759.6 ± 175.7 | 5 |
| Donor 2: Control CAR T | Animals Euthanized | 0 |
| Donor 2: MAGEA4₂₈₆₋₂₉₄ BB/z CAR T | Animals Euthanized | 0 |
| Donor 2: MAGEA4₂₈₆₋₂₉₄ 28/z CAR T | 20.6 ± 10.1 | 5 |

TABLE 44

| | Summary of data, day 84 | |
| --- | --- | --- |
| CAR T Treatment | Average Tumor Size (mm³) ± SEM on Day 84 | Number of mice still alive (of 5) on day 84 |
| Donor 1: Control CAR T | Animals Euthanized | 0 |
| Donor 1: MAGEA4₂₈₆₋₂₉₄ BB/z CAR T | Animals Euthanized | 0 |
| Donor 1: MAGEA4₂₈₆₋₂₉₄ 28/z CAR T | Animals Euthanized | 0 |
| Donor 2: Control CAR T | Animals Euthanized | 0 |
| Donor 2: MAGEA4₂₈₆₋₂₉₄ BB/z CAR T | Animals Euthanized | 0 |
| Donor 2: MAGEA4₂₈₆₋₂₉₄ 28/z CAR T | 73.0 ± 42.6 | 5 |

TABLE 45

| | Summary of data, day 118 | |
| --- | --- | --- |
| CAR T Treatment | Average Tumor Size (mm³) ± SEM on Day 118 | Number of mice still alive (of 5) on day 118 |
| Donor 1: Control CAR T | Animals Euthanized | 0 |
| Donor 1: MAGEA4₂₈₆₋₂₉₄ BB/z CAR T | Animals Euthanized | 0 |
| Donor 1: MAGEA4₂₈₆₋₂₉₄ 28/z CAR T | Animals Euthanized | 0 |

TABLE 45-continued

| | Summary of data, day 118 | |
| --- | --- | --- |
| CAR T Treatment | Average Tumor Size (mm³) ± SEM on Day 118 | Number of mice still alive (of 5) on day 118 |
| Donor 2: Control CAR T | Animals Euthanized | 0 |
| Donor 2: MAGEA4₂₈₆₋₂₉₄ BB/z CAR T | Animals Euthanized | 0 |
| Donor 2: MAGEA4₂₈₆₋₂₉₄ 28/z CAR T | 928.2 ± 291.1 | 5 |

Example 10: MAGE-A4 (230-239)-Targeted CAR T Cells Reduce Growth of MAGE-A4-Expressing Tumors In Vivo in a Xenogenic A375 Melanoma Model Chimeric antigen receptors containing either an anti-HLA-A2/MAGEA4$_{230-239}$ scFv in the $V_L$-$V_H$ orientation plus either 1) a huCD8 hinge/transmembrane domain, a 4-1BB co-stimulatory domain, and a CD3z signaling domain (BB/z CAR), or 2) huCD28 hinge/transmembrane/costimulatory domains and a CD3z signaling domain (28/z CAR) were constructed using the $V_L$ and $V_H$ sequences of mAb33229. As a non-binding control, a 28/z CAR was designed using an irrelevant scFv plus a huCD28 hinge/transmembrane/costimulatory domains and a CD3z signaling domain. These CARs were cloned into a pLVX lentiviral vector with an EF1a promoter and P2A:eGFP sequence (for tracking CAR-transduced cells), and VSV-pseudotyped lentivirus was produced.

CD3+ T cells were isolated from human peripheral blood mononuclear cells (PBMCs) from a normal donor, stimulated with CD3/CD28 microbeads plus 100 U/ml recombinant human IL-2, and transduced with the lentivirus at an MOI=5. The transduced cells were expanded for approximately 14 days with CD3/CD28 microbeads plus 100 U/ml recombinant human IL-2 before being cryopreserved until use during the in vivo experiment.

To determine the in vivo efficacy of anti-HLA-A2/MAGEA4$_{230-239}$-targeted chimeric antigen receptor (CAR) T cells, a xenogenic tumor study was performed. On day 0, immunodeficient NOD.Cg-Prkdc$^{scid}$Il2rg$^{tm1Wjl}$/SzJ (NSG) mice were subcutaneously injected with 5×10⁶ HLA-A2⁺ MAGEA4⁺ A375 human melanoma tumor cells. Mass spectrometry techniques were used to determine that A375 melanoma cells express approximately 553 cell-surface copies of the HLA-A2/MAGEA4$_{230-239}$ peptide. On day 13 after tumors were established, the mice (n=4 or 5 per group) were intravenously injected with 4×10⁶ T cells that express either the non-binding control BB/z CAR (Control CAR T), the anti-HLA-A2/MAGEA4$_{230-239}$ BB/z CAR, or the anti-HLA-A2/MAGEA4$_{230-239}$ 28/z CAR (as determined by the frequency of cells expressing either GFP, which is a marker for those cells that have been transduced with CAR). Tumor growth was assessed through day 28 by measuring tumor volumes.

To determine tumor volume by external caliper, the greatest longitudinal diameter (length in mm) and the greatest transverse diameter (width in mm) were determined. Tumor volumes based on caliper measurements were calculated by the formula: Volume (mm³)=(length× width²)/2.

A375 tumors grew progressively in untreated mice and mice receiving Control CAR T cells. Mice receiving anti-HLA-A2/MAGEA4$_{230-239}$ BB/z CAR T cells demonstrated tumor control, with reduced tumor growth compared to Control CAR T-treated mice on days 19 (p<0.02), 23 (p<0.02) and 26 (p<0.0001) (statistics analyzed by 2-way ANOVA). Anti-HLA-A2/MAGEA4$_{230-239}$ 28/z CART treatment also led to suppression of established A375 tumor growth on days 19 (p=0.007), 23 (p<0.0001), and 26 (p<0.0001) (statistics analyzed by 2-way ANOVA). See Tables 46-54.

TABLE 46

Summary of data, day 7

| CAR T Treatment | Average Tumor Size (mm$^3$) on Day 7 | Tumor size standard error of the mean (SEM) | Number of mice still alive (of 5) on day 7 |
|---|---|---|---|
| Untreated | 59.7 | 9.7 | 4 |
| Control CAR T | 98.1 | 16.2 | 5 |
| MAGEA4$_{230-239}$ BB/z CAR T | 72.8 | 3.9 | 5 |
| MAGEA4$_{230-239}$ 28/z CAR T | 72.3 | 5.9 | 5 |

TABLE 47

Summary of data, day 10

| CAR T Treatment | Average Tumor Size (mm$^3$) on Day 10 | Tumor size standard error of the mean (SEM) | Number of mice still alive (of 5) on day 10 |
|---|---|---|---|
| Untreated | 154.0 | 16.1 | 4 |
| Control CAR T | 163.0 | 21.6 | 5 |
| MAGEA4$_{230-239}$ BB/z CAR T | 146.1 | 4.9 | 5 |
| MAGEA4$_{230-239}$ 28/z CAR T | 148.9 | 14.1 | 5 |

TABLE 48

Summary of data, day 13

| CAR T Treatment | Average Tumor Size (mm$^3$) on Day 13 | Tumor size standard error of the mean (SEM) | Number of mice still alive (of 5) on day 13 |
|---|---|---|---|
| Untreated | 302.9 | 47.2 | 4 |
| Control CAR T | 369.4 | 47.3 | 5 |
| MAGEA4$_{230-239}$ BB/z CAR T | 209.9 | 30.3 | 5 |
| MAGEA4$_{230-239}$ 28/z CAR T | 304.4 | 25.7 | 5 |

TABLE 49

Summary of data, day 17

| CAR T Treatment | Average Tumor Size (mm$^3$) on Day 17 | Tumor size standard error of the mean (SEM) | Number of mice still alive (of 5) on day 17 |
|---|---|---|---|
| Untreated | 702.5 | 105.7 | 4 |
| Control CAR T | 652.7 | 71.3 | 5 |
| MAGEA4$_{230-239}$ BB/z CAR T | 416.1 | 51.4 | 5 |
| MAGEA4$_{230-239}$ 28/z CAR T | 487.1 | 32.0 | 5 |

TABLE 50

Summary of data, day 19

| CAR T Treatment | Average Tumor Size (mm$^3$) on Day 19 | Tumor size standard error of the mean (SEM) | Number of mice still alive (of 5) on day 19 |
|---|---|---|---|
| Untreated | 1191.9 | 174.2 | 4 |
| Control CAR T | 1055.6 | 68.2 | 5 |
| MAGEA4$_{230-239}$ BB/z CAR T | 590.9 | 111.2 | 5 |
| MAGEA4$_{230-239}$ 28/z CAR T | 535.4 | 60.6 | 5 |

TABLE 51

Summary of data, day 23

| CAR T Treatment | Average Tumor Size (mm$^3$) on Day 23 | Tumor size standard error of the mean (SEM) | Number of mice still alive (of 5) on day 23 |
|---|---|---|---|
| Untreated | 1823.6 | 240.4 | 4 |
| Control CAR T | 1583.3 | 74.6 | 5 |
| MAGEA4$_{230-239}$ BB/z CAR T | 1103.7 | 234.8 | 5 |
| MAGEA4$_{230-239}$ 28/z CAR T | 356.2 | 67.3 | 5 |

TABLE 52

Summary of data, day 26

| CAR T Treatment | Average Tumor Size (mm$^3$) on Day 26 | Tumor size standard error of the mean (SEM) | Number of mice still alive (of 5) on day 26 |
|---|---|---|---|
| Untreated | 2605.5 | 196.9 | 4 |
| Control CAR T | 2246.8 | 132.9 | 5 |
| MAGEA4$_{230-239}$ BB/z CAR T | 1435.5 | 498.0 | 4 |
| MAGEA4$_{230-239}$ 28/z CAR T | 332.1 | 132.4 | 5 |

TABLE 53

Summary of data, day 33

| CAR T Treatment | Average Tumor Size (mm$^3$) on Day 33 | Tumor size standard error of the mean (SEM) | Number of mice still alive (of 5) on day 33 |
|---|---|---|---|
| Untreated | Euthanized | Euthanized | 0 |
| Control CAR T | Euthanized | Euthanized | 0 |
| MAGEA4$_{230-239}$ BB/z CAR T | 2618.3 | 652.4 | 4 |
| MAGEA4$_{230-239}$ 28/z CAR T | 712.1 | 302.9 | 5 |

TABLE 54

Summary of data, day 37

| CAR T Treatment | Average Tumor Size (mm$^3$) on Day 37 | Tumor size standard error of the mean (SEM) | Number of mice still alive (of 5) on day 37 |
|---|---|---|---|
| Untreated | Euthanized | Euthanized | 0 |
| Control CAR T | Euthanized | Euthanized | 0 |
| MAGEA4$_{230-239}$ BB/z CAR T | Euthanized | Euthanized | 0 |
| MAGEA4$_{230-239}$ 28/z CAR T | 1021.8 | 387.1 | 5 |

Example 11: Structural Analysis of Fab/Soluble
TCR Binding to HLA-A2 Bound MAGE-A4
(230-239) Polypeptide In an effort to better understand the specific interactions between antibody or TCR and HLA-peptide complex, two x-ray crystal structures and three cryo-electron microscopy (cryo-EM) structures were determined for antibody Fab fragments or engineered soluble portions of TCRs (sTCRs) bound to a complex of HLA-A2 with beta-2-microglobulin (HLA-A2/b2m) displaying the MAGE-A4 230-239 polypeptide in the HLA peptide binding groove (Table 55). X-ray structures of complexes containing two Fabs were determined at 1.4 and 2.5 Å resolution. These two Fabs have highly similar sequences and display near-identical binding modes. A CryoEM structure of a complex containing a 33229 Fab was determined at 3.7 Å resolution, and CryoEM structures of an additional Fab and an sTCR were determined at 3.0 Å and 2.9 Å resolution, respectively. Although they encompass a range of resolutions, in each of the structures the HLA-displayed MAGEA4:230-239 peptide residues are clearly visible in the electron/cryo-EM density maps, allowing for accurate determination of residue-level interactions between the HLA-displayed peptide and complementarity determining regions (CDRs) of the Fab or sTCR.

The structures demonstrate that the Fabs bound the HLA-peptide complex with overall similar orientations. The heavy chain CDRs were situated proximal to the N-terminus of the peptide and light chain CDRs were situated proximal to the C-terminus of the peptide. In each of the Fab-bound structures, the solvent-exposed MAGE-A4 polypeptide residue arginine 235 was located near the central plane that divided the heavy and light chain CDRs. The four Fabs recognized and bound three distinct rotamers of arginine 235. The remainder of the HLA-displayed peptide conformation was very similar across the structures.

The sTCR bound the HLA-peptide complex in an orientation typical for TCRs, with the α chain closer to the N-terminal side of the peptide, and β chain closer to the C-terminal side. The CDRs of the sTCR were shifted closer to the N-terminus of the peptide relative to the Fabs. The sTCR bound to a rotamer of peptide residue arginine 235 that was distinct from those observed in the four Fab-containing structures.

Contacts between the Fab or sTCR and peptide are summarized in Table 55. "Contacts" here are defined as Fab/sTCR residues with non-hydrogen atoms that are within 3.5 Å of non-hydrogen atoms of the HLA-displayed peptide, and can involve hydrogen bonds, charge-charge interactions, or hydrophobic/van der Waals interactions. The bound peptide is numbered according to the residue positions in the MAGE-A4 polypeptide, as follows:

```
Amino      G   V   Y   D   G   R   E   H   T   V  (SEQ ID
acid                                               NO: 49)
Position  230 231 232 233 234 235 236 237 238 239
```

Peptide contacts made by each of the Fabs are concentrated almost exclusively in CDRs HCDR3, LCDR1, and LCDR3. The HCDR3 of each antibody made multiple contacts with the side chain of MAGE-A4 residue 233. The HCDR3 and/or LCDR3 of each Fab contacted the side chain of residue 235. The backbone carbonyl of peptide residue 236 was contacted by the LCDR1 of each Fab. None of the four Fabs contact peptide residues 230, 231, 232, 234, or 239, most of which are inaccessible to Fab binding because they are buried within the HLA groove. Although peptide residue 234 is solvent exposed, its lack of side chain as a glycine limits is ability for CDR contacts. Nonetheless, substitutions at this glycine 234 might diminish binding activity for these antibodies due to the resulting steric clash between a bulkier peptide residue and HCDR3 loops that are in close proximity.

The sTCR contacted residue 233 via its α1 and α3 loops, as well as peptide residue 235 via its β1 and β3 loops. Peptide residues 230, 231, 232, 234, 236, 237, 238, 239 were not contacted by the sTCR; therefore the peptide contact coverage of the sTCR was less complete than each of the Fabs mentioned above, or than observed in other structures of TCRs bound to decameric peptides (e.g., PDB 3QDG).

TABLE 55

| | Peptide contacts | | | | | | | | | |
|---|---|---|---|---|---|---|---|---|---|---|
| | Contacts with MAGEA4: 230-239 peptide (CDR and residues shown) | | | | | | | | | |
| Molecule | G 230 | V 231 | Y 232 | D 233 | G 234 | R 235 | E 236 | H 237 | T 238 | V 239 |
| Fab1 | N/A | N/A | N/A | H3: A108, I109 | N/A | H3: D112 L3: S91, Y92 | L1: S30, Y32 | L3: Y92 | E68 | N/A |
| Fab2 | N/A | N/A | N/A | H3: A108, I109 | N/A | H3: D112 L3: S91, Y92 | L1: T30, Y32 | L3: Y92 | N/A | N/A |
| Fab3 | N/A | N/A | N/A | H3: P101, T102 | N/A | L3: S91, Y92 | H3: Y108 L1: Y32 | N/A | N/A | N/A |
| Fab4 (from mAb 33229) | N/A | N/A | N/A | H3: R101, R102, T103 | N/A | H3: Y106 | L1: Y32 | N/A | N/A | N/A |
| sTCR | N/A | N/A | N/A | α1: S31 α3: G97, Y99 | N/A | β1: E30 β3: F95 | N/A | N/A | N/A | N/A |

Description of Sequences

TABLE 56

| | Sequence Identifiers | | |
| --- | --- | --- | --- |
| SEQ ID NO. | DNA/Polypeptide | Sequence | |
| 1 | DNA | mAb31345 and mAb31345* HCVR | |
| 2 | Polypeptide | mAb31345 and mAb31345* HCVR | |
| 3 | DNA | mAb31345 and mAb31345* HCDR1 | |
| 4 | Polypeptide | mAb31345 and mAb31345* HCDR1 | |
| 5 | DNA | mAb31345 and mAb31345* HCDR2 | |
| 6 | Polypeptide | mAb31345 and mAb31345* HCDR2 | |
| 7 | DNA | mAb31345 and mAb31345* HCDR3 | |
| 8 | Polypeptide | mAb31345 and mAb31345* HCDR3 | |
| 9 | DNA | mAb31345* LCVR | |
| 10 | Polypeptide | mAb31345* LCVR | |
| 11 | DNA | mAb31345 and mAb31345* LCDR1 | |
| 12 | Polypeptide | mAb31345 and mAb31345* LCDR1 | |
| 13 | DNA | mAb31345 and mAb31345* LCDR2 | |
| 14 | Polypeptide | mAb31345 and mAb31345* LCDR2 | |
| 15 | DNA | mAb31345 and mAb31345* LCDR3 | |
| 16 | Polypeptide | mAb31345 and mAb31345* LCDR3 | |
| 17 | DNA | mAb31345 and mAb31345* HC | |
| 18 | Polypeptide | mAb31345 and mAb31345* HC | |
| 19 | DNA | mAb31345 and mAb31345* LC | |
| 20 | Polypeptide | mAb31345 and mAb31345* LC | |
| 21 | DNA | Full length 31345* HLA-A2/MAGE-A4$_{286-294}$-targeted CAR (4-1BB costimulatory domain) | |
| 22 | Polypeptide | Full length 31345* HLA-A2/MAGE-A4$_{286-294}$-targeted CAR (4-1BB costimulatory domain) | |
| 23 | Polypeptide | (G4S)$_1$ linker | |
| 24 | Polypeptide | (G4S)$_2$ linker | |
| 25 | Polypeptide | (G4S)$_3$ linker | |
| 26 | Polypeptide | GSTSGSGKPGSGEGSTKG linker | |
| 27 | Polypeptide | CD8α hinge | |
| 28 | Polypeptide | CD8 Transmembrane domain | |
| 29 | Polypeptide | 4-1BB costimulatory domain | |
| 30 | Polypeptide | CD3zeta signaling domain | |
| 31 | DNA | Full length MAGE-A4 | |
| 32 | Polypeptide | Full length MAGE-A4 | |
| 33 | Polypeptide | MAGE-A4 (286-294) | |
| 34 | DNA | Anti-HLA-A2/HPV16E7(11-19) scFv control CAR | |
| 35 | Polypeptide | Anti-HLA-A2/HPV16E7(11-19) scFv control CAR | |
| 36 | DNA | mAb31345 LCVR | |
| 37 | Polypeptide | mAb31345 LCVR | |
| 38 | DNA | Full length 31345 HLA-A2/MAGE-A4$_{286-294}$-targeted CAR (4-1BB costimulatory domain) | |
| 39 | Polypeptide | Full length 31345 HLA-A2/MAGE-A4$_{286-294}$-targeted CAR (4-1BB costimulatory domain) | |

TABLE 56-continued

| | Sequence Identifiers | | |
| --- | --- | --- | --- |
| SEQ ID NO. | DNA/Polypeptide | Sequence | |
| 40 | Polypeptide | 2A peptide and green fluorescent protein | |
| 41 | Polypeptide | CD28 hinge | |
| 42 | DNA | CD28 hinge | |
| 43 | Polypeptide | CD28 transmembrane | |
| 44 | DNA | CD28 transmembrane | |
| 45 | Polypeptide | CD28 costimulatory | |
| 46 | DNA | CD28 costimulatory | |
| 47 | Polypeptide | Full length 31345 HLA-A2/MAGE-A4$_{286-294}$-targeted CAR (CD28 costimulatory domain) | |
| 48 | DNA | Full length 31345 HLA-A2/MAGE-A4$_{286-294}$-targeted CAR (CD28 costimulatory domain) | |
| 49 | Polypeptide | MAGE-A4 (230-239) | |
| 50 | DNA | mAb33229 HCVR | |
| 51 | Polypeptide | mAb33229 HCVR | |
| 52 | DNA | mAb33229 HCDR1 | |
| 53 | Polypeptide | mAb33229 HCDR1 | |
| 54 | DNA | mAb33229 HCDR2 | |
| 55 | Polypeptide | mAb33229 HCDR2 | |
| 56 | DNA | mAb33229 HCDR3 | |
| 57 | Polypeptide | mAb33229 HCDR3 | |
| 58 | DNA | mAb33229 LCVR | |
| 59 | Polypeptide | mAb33229 LCVR | |
| 60 | DNA | mAb33229 LCDR1 | |
| 61 | Polypeptide | mAb33229 LCDR1 | |
| 62 | DNA | mAb33229 LCDR2 | |
| 63 | Polypeptide | mAb33229 LCDR2 | |
| 64 | DNA | mAb33229 LCDR3 | |
| 65 | Polypeptide | mAb33229 LCDR3 | |
| 66 | DNA | mAb33229 HC | |
| 67 | Polypeptide | mAb33229 HC | |
| 68 | DNA | mAb33229 LC | |
| 69 | Polypeptide | mAb33229 LC | |
| 70 | DNA | Full length 33229 HLA-A2/MAGE-A4$_{230-239}$-targeted CAR (4-1BB costimulatory domain) | |
| 71 | Polypeptide | Full length 33229 HLA-A2/MAGE-A4$_{230-239}$-targeted CAR (4-1BB costimulatory domain) | |
| 72 | DNA | Full length 33229 HLA-A2/MAGE-A4$_{230-239}$-targeted CAR (CD28 costimulatory domain) | |
| 73 | Polypeptide | Full length 33229 HLA-A2/MAGE-A4$_{230-239}$-targeted CAR (CD28 costimulatory domain) | |
| 74 | Polypeptide | Full length 31345* HLA-A2/MAGE-A4$_{286-294}$-targeted CAR (CD28 costimulatory domain) | |
| 75 | DNA | Full length 31345* HLA-A2/MAGE-A4$_{286-294}$-targeted CAR (CD28 costimulatory domain) | |
| 76 | Polypeptide | Full length 31345 HLA-A2/MAGE-A4$_{286-294}$-targeted CAR (4-1BB costimulatory domain) with P2A/GFP sequence | |
| 77 | Polypeptide | Full length 31345 HLA-A2/MAGE-A4$_{286-294}$-targeted CAR (CD28 costimulatory domain) with P2A/GFP sequence | |
| 78 | Polypeptide | Full length 31345* HLA-A2/MAGE-A4$_{286-294}$-targeted CAR (4-1BB costimulatory domain) with P2A/GFP sequence | |

TABLE 56-continued

| Sequence Identifiers | | |
| --- | --- | --- |
| SEQ ID NO. | DNA/Polypeptide | Sequence |
| 79 | Polypeptide | Full length 31345* HLA-A2/MAGE-A4$_{286\text{-}294}$-targeted CAR (CD28 costimulatory domain) with P2A/GFP sequence |
| 80 | Polypeptide | Full length 33229 HLA-A2/MAGE-A4$_{230\text{-}239}$-targeted CAR (4-1BB costimulatory domain) with P2A/GFP sequence |
| 81 | Polypeptide | Full length 33229 HLA-A2/MAGE-A4$_{230\text{-}239}$-targeted CAR (CD28 costimulatory |

TABLE 56-continued

| Sequence Identifiers | | |
| --- | --- | --- |
| SEQ ID NO. | DNA/Polypeptide | Sequence |
| | | domain) with P2A/GFP sequence |

Annotated Sequences

In the following annotated sequences, the parts are identified by alternating non-underlined sections with underlined sections, and the order of the parts corresponds to the order listed below each sequence (i.e., the first non-underlined section is the VL, the following underlined section is the (G4S)3, the following non-underlined section is the VH, and so on).

MAGEA4(286-294) 31345 VL-VH BBz CAR P2A-GFP (SEQ ID NO: 76)

DIQMTQSPSSLSASVGDRVTITCRASQSISSYLNWYQQKPGKAPKLLIYAASSLQSGVPSRFS

GSGSGTDFTLTISSLQPEDFATYYCQQSYSTPPITFGQGTRLEIKGGGGSGGGGSGGGGSQVQ

LVESGGGLVKPGGSLRLSCAASGFTFSEYYMTWIRQAPGQGLEWVSYISSSGFNIYYADSVK

GRFTISRDNAKNSLFLQMNSLRVEDTAVYYCAREGVTDGMDVWGQGTTVTVSSGGGGSTT

TPAPRPPTPAPTIASQPLSLRPEACRPAAGGAVHTRGLDFACDIYIWAPLAGTCGVLLLSLVI

TLYCKRGRKKLLYIFKQPFMRPVQTTQEEDGCSCRFPEEEEGGCELRVKFSRSADAPAYQQ

GQNQLYNELNLGRREEYDVLDKRRGRDPEMGGKPRRKNPQEGLYNELQKDKMAEAYSEI

GMKGERRRGKGHDGLYQGLSTATKDTYDALHMQALPPRGSGATNFSLLKQAGDVEENPG

PMVSKGEELFTGVVPILVELDGDVNGHKFSVSGEGEGDATYGKLTLKFICTTGKLPVPWPTL

VTTLTYGVQCFSRYPDHMKQHDFFKSAMPEGYVQERTIFFKDDGNYKTRAEVKFEGDTLV

NRIELKGIDFKEDGNILGHKLEYNYNSHNVYIMADKQKNGIKVNFKIRHNIEDGSVQLADH

YQQNTPIGDGPVLLPDNHYLSTQSALSKDPNEKRDHMVLLEFVTAAGITLGMDELYK

VL
(G4S)3
VH
G4S
CD8 hinge/TM
4-1BB costimulatory domain
CD3Z
P2A/GFP

MAGEA4(286-294) 31345 VL-VH CD28hinge/TM/cytoCD3z CAR P2A-GFP (SEQ ID NO: 77)

DIQMTQSPSSLSASVGDRVTITCRASQSISSYLNWYQQKPGKAPKLLIYAASSLQSGVPSRFS

GSGSGTDFTLTISSLQPEDFATYYCQQSYSTPPITFGQGTRLEIKGGGGSGGGGSGGGGSQVQ

LVESGGGLVKPGGSLRLSCAASGFTFSEYYMTWIRQAPGQGLEWVSYISSSGFNIYYADSVK

GRFTISRDNAKNSLFLQMNSLRVEDTAVYYCAREGVTDGMDVWGQGTTVTVSSGGGGSIE

VMYPPPYLDNEKSNGTIIHVKGKHLCPSPLFPGPSKPFWVLVVVGGVLACYSLLVTVAFIIF

WVRSKRSRLLHSDYMNMTPRRPGPTRKHYQPYAPPRDFAAYRSRVKFSRSADAPAYQQGQ

NQLYNELNLGRREEYDVLDKRRGRDPEMGGKPRRKNPQEGLYNELQKDKMAEAYSEIGM

KGERRRGKGHDGLYQGLSTATKDTYDALHMQALPPRGSGATNFSLLKQAGDVEENPGPM

VSKGEELFTGVVPILVELDGDVNGHKFSVSGEGEGDATYGKLTLKFICTTGKLPVPWPTLVT

TLTYGVQCFSRYPDHMKQHDFFKSAMPEGYVQERTIFFKDDGNYKTRAEVKFEGDTLVNRI

ELKGIDFKEDGNILGHKLEYNYNSHNVYIMADKQKNGIKVNFKIRHNIEDGSVQLADHYQQ

NTPIGDGPVLLPDNHYLSTQSALSKDPNEKRDHMVLLEFVTAAGITLGMDELYK

-continued
```
VL
(G4S)3
VH
G4S
CD28 hinge
CD28 TM
CD28 costimulatory domain
CD3Z
P2A/GFP MAGEA4(286-294) 31345* VL-VH BBz CAR P2A-GFP
                                             (SEQ ID NO: 78)
DIQMTQSPSSLSASVGDRVTITCRASQSISSYLNWYQQKPGKAPKLLIYAASSLQSGVPSRFS

GSGSGTDFTLTISSLQPEDFATYYCQQSYSTPPITFGQGTRLEIKRGGGGSGGGGSGGGGSQV

QLVESGGGLVKPGGSLRLSCAASGFTFSEYYMTWIRQAPGQGLEWVSYISSSGFNIYYADSV

KGRFTISRDNAKNSLFLQMNSLRVEDTAVYYCAREGVTDGMDVWGQGTTVTVSSGGGGS

TTTPAPRPPTPAPTIASQPLSLRPEACRPAAGGAVHTRGLDFACDIYIWAPLAGTCGVLLLSL

VITLYCKRGRKKLLYIFKQPFMRPVQTTQEEDGCSCRFPEEEEGGCELRVKFSRSADAPAYQ

QGQNQLYNELNLGRREEYDVLDKRRGRDPEMGGKPRRKNPQEGLYNELQKDKMAEAYSE

IGMKGERRRGKGHDGLYQGLSTATKDTYDALHMQALPPRGSGATNFSLLKQAGDVEENPG

PMVSKGEELFTGVVPILVELDGDVNGHKFSVSGEGEGDATYGKLTLKFICTTGKLPVPWPTL

VTTLTYGVQCFSRYPDHMKQHDFFKSAMPEGYVQERTIFFKDDGNYKTRAEVKFEGDTLV

NRIELKGIDFKEDGNILGHKLEYNYNSHNVYIMADKQKNGIKVNFKIRHNIEDGSVQLADH

YQQNTPIGDGPVLLPDNHYLSTQSALSKDPNEKRDHMVLLEFVTAAGITLGMDELYK
VL
(G4S)3
VH
G4S
CD8 hinge/TM
4-1BB costimulatory domain
CD3Z
P2A/GFP MAGEA4(286-294) 31345* VL-VH CD28hinge/TM/cytoCD3z CAR P2A-GFP
                                             (SEQ ID NO: 79)
DIQMTQSPSSLSASVGDRVTITCRASQSISSYLNWYQQKPGKAPKLLIYAASSLQSGVPSRFS

GSGSGTDFTLTISSLQPEDFATYYCQQSYSTPPITFGQGTRLEIKRGGGGSGGGGSGGGGSQV

QLVESGGGLVKPGGSLRLSCAASGFTFSEYYMTWIRQAPGQGLEWVSYISSSGFNIYYADSV

KGRFTISRDNAKNSLFLQMNSLRVEDTAVYYCAREGVTDGMDVWGQGTTVTVSSGGGGSI

EVMYPPPYLDNEKSNGTIIHVKGKHLCPSPLFPGPSKPFWVLVVVGGVLACYSLLVTVAFIIF

WVRSKRSRLLHSDYMNMTPRRPGPTRKHYQPYAPPRDFAAYRSRVKFSRSADAPAYQQGQ

NQLYNELNLGRREEYDVLDKRRGRDPEMGGKPRRKNPQEGLYNELQKDKMAEAYSEIGM

KGERRRGKGHDGLYQGLSTATKDTYDALHMQALPPRGSGATNFSLLKQAGDVEENPGPM

VSKGEELFTGVVPILVELDGDVNGHKFSVSGEGEGDATYGKLTLKFICTTGKLPVPWPTLVT

TLTYGVQCFSRYPDHMKQHDFFKSAMPEGYVQERTIFFKDDGNYKTRAEVKFEGDTLVNRI

ELKGIDFKEDGNILGHKLEYNYNSHNVYIMADKQKNGIKVNFKIRHNIEDGSVQLADHYQQ

NTPIGDGPVLLPDNHYLSTQSALSKDPNEKRDHMVLLEFVTAAGITLGMDELYK
VL
(G4S)3
VH
G4S
CD28 hinge
CD28 TM
CD28 costimulatory domain
CD3Z
P2A/GFP
```

-continued

MAGEA4(230-239) 33229 VL-VH BBz CAR P2A-GFP (SEQ ID NO: 80)

DIQMTQSPSSLSASVGDRVTITCQASQDISNYLNWYQQKRGKAPKLLIYDASILETGVPSRFS

GSGSGTDFTFTISSLQPEDIATYFCQQFDNVPLTFGGGTKVEIKGGGGSGGGGSGGGGSEVQ

LVESGGGLVQPGRSLRLSCAASGFTFDDYAMHWVRQAPGKGLEWVSGISWNSGSIAYADS

VKGRFTISRDNAKNSLYLQMNSLRSEDTALYHCAKDWRRTNYYGMDVWGQGTTVTVSSG

GGGSTTTPAPRPPTPAPTIASQPLSLRPEACRPAAGGAVHTRGLDFACDIYIWAPLAGTCGVL

LLSLVITLYCKRGRKKLLYIFKQPFMRPVQTTQEEDGCSCRFPEEEEGGCELRVKFSRSADAP

AYQQGQNQLYNELNLGRREEYDVLDKRRGRDPEMGGKPRRKNPQEGLYNELQKDKMAE

AYSEIGMKGERRRGKGHDGLYQGLSTATKDTYDALHMQALPPRGSGATNFSLLKQAGDVE

ENPGPMVSKGEELFTGVVPILVELDGDVNGHKFSVSGEGEGDATYGKLTLKFICTTGKLPVP

WPTLVTTLTYGVQCFSRYPDHMKQHDFFKSAMPEGYVQERTIFFKDDGNYKTRAEVKFEG

DTLVNRIELKGIDFKEDGNILGHKLEYNYNSHNVYIMADKQKNGIKVNFKIRHNIEDGSVQL

ADHYQQNTPIGDGPVLLPDNHYLSTQSALSKDPNEKRDHMVLLEFVTAAGITLGMDELYK
VL
(G4S)3
VH
G4S
CD8 hinge/TM
4-1BB costimulatory domain
CD3Z
P2A/GFP MAGEA4(230-239) 33229 VL-VH CD28hinge/TM/cytoCD3z CAR P2A-GFP (SEQ ID NO: 81)

DIQMTQSPSSLSASVGDRVTITCQASQDISNYLNWYQQKRGKAPKLLIYDASILETGVPSRFS

GSGSGTDFTFTISSLQPEDIATYFCQQFDNVPLTFGGGTKVEIKGGGGSGGGGSGGGGSEVQ

LVESGGGLVQPGRSLRLSCAASGFTFDDYAMHWVRQAPGKGLEWVSGISWNSGSIAYADS

VKGRFTISRDNAKNSLYLQMNSLRSEDTALYHCAKDWRRTNYYGMDVWGQGTTVTVSSG

GGGSIEVMYPPPYLDNEKSNGTIIHVKGKHLCPSPLFPGPSKPFWVLVVVGGVLACYSLLVT

VAFIIFWVRSKRSRLLHSDYMNMTPRRPGPTRKHYQPYAPPRDFAAYRSRVKFSRSADAPA

YQQGQNQLYNELNLGRREEYDVLDKRRGRDPEMGGKPRRKNPQEGLYNELQKDKMAEA

YSEIGMKGERRRGKGHDGLYQGLSTATKDTYDALHMQALPPRGSGATNFSLLKQAGDVEE

NPGPMVSKGEELFTGVVPILVELDGDVNGHKFSVSGEGEGDATYGKLTLKFICTTGKLPVP

WPTLVTTLTYGVQCFSRYPDHMKQHDFFKSAMPEGYVQERTIFFKDDGNYKTRAEVKFEG

DTLVNRIELKGIDFKEDGNILGHKLEYNYNSHNVYIMADKQKNGIKVNFKIRHNIEDGSVQL

ADHYQQNTPIGDGPVLLPDNHYLSTQSALSKDPNEKRDHMVLLEFVTAAGITLGMDELYK
VL
(G4S)3
VH
G4S
CD28 hinge
CD28 TM
CD28 costimulatory domain
CD3Z
P2A/GFP The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A Melanoma-Associated Antigen A4 (MAGE-A4)-specific chimeric antigen receptor comprising, from N-terminus to C-terminus:
   (a) an extracellular ligand-binding domain comprising an anti-MAGE-A4 antigen-binding domain;
   (b) a hinge;
   (c) a transmembrane domain; and
   (d) a cytoplasmic domain comprising a costimulatory domain, and a signaling domain;
   wherein the extracellular ligand-binding domain is an anti-MAGE-A4 single chain variable fragment (scFv) domain comprising a light chain variable region (LCVR) and a heavy chain variable region (HCVR) joined by a linker,
   wherein:
      (A) the LCVR comprises LCDR1, LCDR2, and LCDR3 domains comprising the amino acid sequences of SEQ ID NOs: 12, 14, and 16, respectively, and the HCVR comprises HCDR1, HCDR2, and HCDR3 domains comprising the amino acid sequences of SEQ ID NOs: 4, 6, and 8, respectively, or
      (B) the LCVR comprises LCDR1, LCDR2, and LCDR3 domains comprising the amino acid sequences of SEQ ID NOs: 61, 63, and 65, respectively, and the HCVR comprises HCDR1, HCDR2, and HCDR3 domains comprising the amino acid sequences of SEQ ID NOs: 53, 55, and 57, respectively.

2. The chimeric antigen receptor of claim 1, wherein the LCVR comprises LCDR1, LCDR2, and LCDR3 domains comprising the amino acid sequences of SEQ ID NOs: 12, 14, and 16, respectively, and the HCVR comprises HCDR1, HCDR2, and HCDR3 domains comprising the amino acid sequences of SEQ ID NOs: 4, 6, and 8, respectively.

3. The chimeric antigen receptor of claim 1, wherein the LCVR comprises LCDR1, LCDR2, and LCDR3 domains comprising the amino acid sequences of SEQ ID NOs: 61, 63, and 65, respectively, and the HCVR comprises HCDR1, HCDR2, and HCDR3 domains comprising the amino acid sequences of SEQ ID NOs: 53, 55, and 57, respectively.

4. The chimeric antigen receptor of claim 1, wherein the hinge and the transmembrane domain are from a CD28 polypeptide, the costimulatory domain comprises a CD28 costimulatory domain, and the signaling domain comprises a CD3zeta signaling domain.

5. The chimeric antigen receptor of claim 1, wherein the hinge and the transmembrane domain are from a CD8α polypeptide, the costimulatory domain comprises a 4-1BB costimulatory domain, and the signaling domain comprises a CD3zeta signaling domain.

6. The chimeric antigen receptor of claim 2, wherein the LCVR comprises the amino acid sequence of SEQ ID NO: 37 and the HCVR comprises the amino acid sequence of SEQ ID NO: 2.

7. The chimeric antigen receptor of claim 3, wherein the LCVR comprises the amino acid sequence of SEQ ID NO: 59 and the HCVR comprises the amino acid sequence of SEQ ID NO: 51.

8. The chimeric antigen receptor of claim 1, further comprising a peptide linker between the extracellular ligand-binding domain and the hinge.

9. The chimeric antigen receptor of claim 1, wherein the linker comprises an amino acid sequence selected from the group consisting of SEQ ID NOs: 23-26.

10. The chimeric antigen receptor of claim 1, wherein:
   (a) the hinge comprises the amino acid sequence of SEQ ID NO: 41;
   (b) the transmembrane domain comprises the amino acid sequence of SEQ ID NO: 43;
   (c) the costimulatory domain comprises the amino acid sequence of SEQ ID NO: 45; and/or
   (d) the signaling domain comprises the amino acid sequence of SEQ ID NO: 30.

11. The chimeric antigen receptor of claim 2, wherein the chimeric antigen receptor comprises the amino acid sequence of SEQ ID NO: 47.

12. The chimeric antigen receptor of claim 3, wherein the chimeric antigen receptor comprises the amino acid sequence of SEQ ID NO: 73.

13. An isolated nucleic acid molecule encoding the chimeric antigen receptor of claim 1.

14. An isolated nucleic acid molecule encoding the chimeric antigen receptor of claim 11, wherein the nucleic acid molecule comprises a nucleotide sequence of SEQ ID NO: 48.

15. An isolated nucleic acid molecule encoding the chimeric antigen receptor of claim 12, wherein the nucleic acid molecule comprises a nucleotide sequence of SEQ ID NO: 72.

16. A vector comprising the nucleic acid molecule of claim 13.

17. The vector of claim 16, wherein the vector is a DNA vector, an RNA vector, a plasmid, a lentivirus vector, an adenovirus vector, or a retroviral vector.

18. A cell comprising the vector of claim 16.

19. An engineered cell comprising a chimeric antigen receptor of claim 1.

20. The engineered cell of claim 19, wherein the engineered cell is a T lymphocyte.

21. The engineered cell of claim 20, wherein the T lymphocyte is an inflammatory T lymphocyte, a cytotoxic T lymphocyte, a regulatory T lymphocyte, or a helper T lymphocyte.

22. The engineered cell of claim 21 that is a CD8+ cytotoxic T lymphocyte.

23. A population of engineered cells, which is obtained by:

(a) providing a population of immune cells, which have been obtained from a subject;

(b) introducing into the immune cells a nucleic acid molecule encoding a chimeric antigen receptor of claim 1;

(c) culturing the immune cells under conditions to express the nucleic acid molecules; and (d) isolating the immune cells expressing the chimeric antigen receptor at the cells' surface.

24. A pharmaceutical composition comprising a genetically-modified human T cell and a pharmaceutically acceptable carrier, wherein the genetically-modified human T cell comprises a chimeric antigen receptor of claim 1.

25. A method for treating a MAGE-A4-expressing cancer, the method comprising administering the pharmaceutical composition of claim 24 to a subject.

26. The method of claim 25, wherein the MAGE-A4-expressing cancer is selected from the group consisting of multiple myeloma, synovial sarcoma, esophageal cancer, head and neck cancer, lung cancer, bladder cancer, ovarian cancer, uterine cancer, stomach cancer, cervical cancer, breast cancer, and melanoma.

27. The method of claim 26, wherein the MAGE-A4-expressing cancer is multiple myeloma.

28. A method of engineering a population of cells to express a chimeric antigen receptor, comprising:

(a) providing a population of immune cells;

(b) introducing into the immune cells a nucleic acid molecule encoding a chimeric antigen receptor of claim 1;

(c) culturing the immune cells under conditions to express the nucleic acid molecule; and (d) isolating the immune cells expressing the chimeric antigen receptor at the cells' surface.

29. The method of claim 28, wherein the population of immune cells in (a) is obtained from a subject.

30. An antibody or antigen-binding fragment thereof that specifically binds Melanoma-Associated Antigen A4 (MAGE-A4), wherein the antibody or antigen-binding fragment comprises a heavy chain variable region (HCVR) comprising three heavy chain complementarity determining regions, HCDR1, HCDR2 and HCDR3, comprising the amino acid sequences of SEQ ID NOs: 4, 6 and 8, respectively, and a light chain variable region (LCVR) comprising three light chain complementarity determining regions, LCDR1, LCDR2 and LCDR3, comprising the amino acid sequences of SEQ ID NOs: 12, 14 and 16.

31. The antibody or antigen-binding fragment thereof of claim 30, wherein the HCVR comprises the amino acid sequence of SEQ ID NO: 2, and the LCVR comprises the amino acid sequence of SEQ ID NO: 37.

32. An antibody or antigen-binding fragment thereof that specifically binds Melanoma-Associated Antigen A4 (MAGE-A4), wherein the antibody or antigen-binding fragment comprises a heavy chain variable region (HCVR) comprising three heavy chain complementarity determining regions, HCDR1, HCDR2 and HCDR3, comprising the amino acid sequences of SEQ ID NOs: 53, 55 and 57, respectively, and a light chain variable region (LCVR) comprising three light chain complementarity determining regions, LCDR1, LCDR2 and LCDR3, comprising the amino acid sequences of SEQ ID NOs: 61, 63 and 65.

33. The antibody or antigen-binding fragment thereof of claim 32, wherein the HCVR comprises the amino acid sequence of SEQ ID NO: 51, and the LCVR comprises the amino acid sequence of SEQ ID NO: 59.

34. An engineered cell comprising a chimeric antigen receptor of claim 11.

35. An engineered cell comprising a chimeric antigen receptor of claim 12.

* * * * *

SEQUENCE LISTING

<160> NUMBER OF SEQ ID NOS: 81

<210> SEQ ID NO 1
<211> LENGTH: 354
<212> TYPE: DNA
<213> ORGANISM: Artificial Sequence
<220> FEATURE:
<223> OTHER INFORMATION: Synthetic

<400> SEQUENCE: 1
caggtgcagc tggtggagtc tggggggaggc ttggtcaagc ctggagggtc cctgagactc      60
tcctgtgcag cctctggatt cactttcagt gaatactaca tgacctggat ccgccaggct     120
ccagggcagg ggctggagtg ggtttcatac attagtagta gtggttttaa catatactac     180
gcagactctg tgaagggccg attcaccatc tcaagggaca acgccaagaa ctcactgttt     240
ctgcaaatga acagcctgag agtcgaggac acggccgtat attactgtgc gagagaaggt     300
gtaacggacg gtatggacgt ctggggccaa gggaccacgg tcaccgtctc ctca           354

<210> SEQ ID NO 2
<211> LENGTH: 118
<212> TYPE: PRT
<213> ORGANISM: Artificial Sequence
<220> FEATURE:
<223> OTHER INFORMATION: Synthetic

<400> SEQUENCE: 2

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Glu Tyr
            20                  25                  30

Tyr Met Thr Trp Ile Arg Gln Ala Pro Gly Gln Gly Leu Glu Trp Val
        35                  40                  45

Ser Tyr Ile Ser Ser Ser Gly Phe Asn Ile Tyr Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Val Glu Asp Thr Ala Val Tyr Tyr Cys
                85                  90                  95

Ala Arg Glu Gly Val Thr Asp Gly Met Asp Val Trp Gly Gln Gly Thr
            100                 105                 110

Thr Val Thr Val Ser Ser
        115

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggattcactt tcagtgaata ctac                                             24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Ser Glu Tyr Tyr
1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
attagtagta gtggttttaa cata                                          24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Ser Ser Ser Gly Phe Asn Ile
1               5

<210> SEQ ID NO 7
<211> LENGTH: 33
<212> TYPE: DNA
<213> ORGANISM: Artificial Sequence
<220> FEATURE:
<223> OTHER INFORMATION: Synthetic

<400> SEQUENCE: 7
gcgagagaag gtgtaacgga cggtatggac gtc                                33

<210> SEQ ID NO 8
<211> LENGTH: 11
<212> TYPE: PRT
<213> ORGANISM: Artificial Sequence
<220> FEATURE:
<223> OTHER INFORMATION: Synthetic

<400> SEQUENCE: 8

Ala Arg Glu Gly Val Thr Asp Gly Met Asp Val
1               5                   10

<210> SEQ ID NO 9
<211> LENGTH: 327
<212> TYPE: DNA
<213> ORGANISM: Artificial Sequence
<220> FEATURE:
<223> OTHER INFORMATION: Synthetic

<400> SEQUENCE: 9
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta cccctccgat caccttcggc          300
caagggacac gactggagat taaacga                                               327

<210> SEQ ID NO 10
<211> LENGTH: 109
<212> TYPE: PRT
<213> ORGANISM: Artificial Sequence
<220> FEATURE:
<223> OTHER INFORMATION: Synthetic

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg
            100                 105

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
cagagcatta gcagctat                                                         18

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Gln Ser Ile Ser Ser Tyr
1               5

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 gctgcatcc                                                                   9

<210> SEQ ID NO 14
<211> LENGTH: 3
<212> TYPE: PRT
<213> ORGANISM: Artificial Sequence
<220> FEATURE:

<223> OTHER INFORMATION: Synthetic

<400> SEQUENCE: 14

Ala Ala Ser
1

<210> SEQ ID NO 15
<211> LENGTH: 30
<212> TYPE: DNA
<213> ORGANISM: Artificial Sequence
<220> FEATURE:
<223> OTHER INFORMATION: Synthetic

<400> SEQUENCE: 15
caacagagtt acagtaccccc tccgatcacc                                    30

<210> SEQ ID NO 16
<211> LENGTH: 10
<212> TYPE: PRT
<213> ORGANISM: Artificial Sequence
<220> FEATURE:
<223> OTHER INFORMATION: Synthetic

<400> SEQUENCE: 16

Gln Gln Ser Tyr Ser Thr Pro Pro Ile Thr
1               5                   10

<210> SEQ ID NO 17
<211> LENGTH: 1347
<212> TYPE: DNA
<213> ORGANISM: Artificial Sequence
<220> FEATURE:
<223> OTHER INFORMATION: Synthetic

<400> SEQUENCE: 17
caggtgcagc tggtggagtc tggggggaggc ttggtcaagc ctggagggtc cctgagactc      60
tcctgtgcag cctctggatt cactttcagt gaatactaca tgacctggat ccgccaggct     120
ccagggcagg ggctggagtg ggtttcatac attagtagta gtggtttttaa catatactac     180 gcagactctg tgaagggccg attcaccatc tcaaggggaca acgccaagaa ctcactgttt     240
ctgcaaatga acagcctgag agtcgaggac acggccgtat attactgtgc gagagaaggt     300
gtaacggacg gtatggacgt ctggggccaa gggaccacgg tcaccgtctc ctcagcctcc     360
accaagggcc catcggtctt cccccctggcg ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct tgggcaccca gacctacatc     600
tgcaacgtga atcacaagcc cagcaacacc aaggtggaca agaaagttga gcccaaatct     660
tgtgacaaaa ctcacacatg cccaccgtgc ccagcacctg aactcctggg gggaccgtca     720
gtcttcctct tcccccccaaa acccaaggac accctcatga tctcccggac ccctgaggtc     780
acatgcgtgg tggtggacgt gagccacgaa gaccctgagg tcaagttcaa ctggtacgtg     840
gacggcgtgg aggtgcataa tgccaagaca aagccgcggg aggagcagta caacagcacg     900
taccgtgtgg tcagcgtcct caccgtcctg caccaggact ggctgaatgg caaggagtac     960
aagtgcaagg tctccaacaa agccctccca gcccccatcg agaaaaccat ctccaaagcc    1020
aaagggcagc cccgagaacc acaggtgtac accctgcccc catcccggga tgagctgacc    1080
aagaaccagg tcagcctgac ctgcctggtc aaaggcttct atcccagcga catcgccgtg    1140

```
gagtgggaga gcaatgggca gccggagaac aactacaaga ccacgcctcc cgtgctggac      1200
tccgacggct ccttcttcct ctacagcaag ctcaccgtgg acaagagcag gtggcagcag      1260
gggaacgtct tctcatgctc cgtgatgcat gaggctctgc acaaccacta cacgcagaag      1320
tccctctccc tgtctccggg taaatga      1347
```

```
<210> SEQ ID NO 18
<211> LENGTH: 448
<212> TYPE: PRT
<213> ORGANISM: Artificial Sequence
<220> FEATURE:
<223> OTHER INFORMATION: Synthetic

<400> SEQUENCE: 18

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Glu Tyr
            20                  25                  30

Tyr Met Thr Trp Ile Arg Gln Ala Pro Gly Gln Gly Leu Glu Trp Val
        35                  40                  45

Ser Tyr Ile Ser Ser Ser Gly Phe Asn Ile Tyr Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Val Glu Asp Thr Ala Val Tyr Tyr Cys
                85                  90                  95

Ala Arg Glu Gly Val Thr Asp Gly Met Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320
```

-continued

```
Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445
```

<210> SEQ ID NO 19
<211> LENGTH: 648
<212> TYPE: DNA
<213> ORGANISM: Artificial Sequence
<220> FEATURE:
<223> OTHER INFORMATION: Synthetic

<400> SEQUENCE: 19

```
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccgtca     180
aggttcagtg gcagtggatc tgggacagat ttcactctca ccatcagcag tctgcaacct     240
gaagattttg caacttacta ctgtcaacag agttacagta cccctccgat caccttcggc     300
caagggacac gactggagat taaacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaagtctacg cctgcgaagt cacccatcag     600
ggcctgagct cgcccgtcac aaagagcttc aacaggggag agtgttag              648
```

<210> SEQ ID NO 20
<211> LENGTH: 215
<212> TYPE: PRT
<213> ORGANISM: Artificial Sequence
<220> FEATURE:
<223> OTHER INFORMATION: Synthetic

<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
```

```
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 21
<211> LENGTH: 1413
<212> TYPE: DNA
<213> ORGANISM: Artificial Sequence
<220> FEATURE:
<223> OTHER INFORMATION: Synthetic

<400> SEQUENCE: 21
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccgtca     180
aggttcagtg gcagtggatc tgggacagat ttcactctca ccatcagcag tctgcaacct     240
gaagattttg caacttacta ctgtcaacag agttacagta cccctccgat caccttcggc     300
caagggacac gactggagat taaacgaggt ggaggcggta gtggcggagg cggaagtggt     360
ggaggaggct cacaggtgca gctggtggag tctgggggag gcttggtcaa gcctggaggg     420
tccctgagac tctcctgtgc agcctctgga ttcactttca gtaatacta catgacctgg      480 atccgccagg ctccagggca ggggctggag tgggtttcat acattagtag tagtggtttt     540
aacatatact acgcagactc tgtgaagggc cgattcacca tctcaaggga caacgccaag     600
aactcactgt ttctgcaaat gaacagcctg agagtcgagg acacggccgt atattactgt     660
gcgagagaag gtgtaacgga cggtatggac gtctgggggcc aagggaccac ggtcaccgtc    720
tcctcaggag gtggtggaag tactaccact cctgctcccc gcccccaac acctgctcca      780 actattgcat cccaaccact ctccctcaga cccgaagctt gtcgcccgc cgccggaggt      840 gctgttcaca ctagaggact cgattttgct tgcgacattt atatctgggc cccacttgca     900
ggtacttgcg agtattgct gctctcactt gttattactc tttattgcaa acggggcaga      960
aagaaactcc tgtatatatt caaacaacca tttatgagac cagtacaaac tactcaagag    1020
gaagatggct gtagctgccg atttccagaa gaagaagaag gaggatgtga actgagagtg    1080
aagttcagca ggagcgcaga cgccccccgcg taccagcagg ccagaaacca gctctataac    1140
gagctcaatc taggacgaag agaggagtac gatgtttttgg acaagagacg tggccgggac   1200
```

-continued

```
cctgagatgg ggggaaagcc gagaaggaag aaccctcagg aaggcctgta caatgaactg      1260
cagaaagata agatggcgga ggcctacagt gagattggga tgaaaggcga gcgccggagg      1320 ggcaagggc acgatggcct ttaccagggt ctcagtacag ccaccaagga cacctacgac      1380
gcccttcaca tgcaggccct gcccctcgc taa                                    1413
```

```
<210> SEQ ID NO 22
<211> LENGTH: 470
<212> TYPE: PRT
<213> ORGANISM: Artificial Sequence
<220> FEATURE:
<223> OTHER INFORMATION: Synthetic

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg Gly Gly Gly
            100                 105                 110

Gly Ser Gly Gly Gly Gly Ser Gly Gly Gly Ser Gln Val Gln Leu
            115                 120                 125

Val Glu Ser Gly Gly Gly Leu Val Lys Pro Gly Gly Ser Leu Arg Leu
        130                 135                 140

Ser Cys Ala Ala Ser Gly Phe Thr Phe Ser Glu Tyr Tyr Met Thr Trp
145                 150                 155                 160

Ile Arg Gln Ala Pro Gly Gln Gly Leu Glu Trp Val Ser Tyr Ile Ser
                165                 170                 175

Ser Ser Gly Phe Asn Ile Tyr Tyr Ala Asp Ser Val Lys Gly Arg Phe
            180                 185                 190

Thr Ile Ser Arg Asp Asn Ala Lys Asn Ser Leu Phe Leu Gln Met Asn
            195                 200                 205

Ser Leu Arg Val Glu Asp Thr Ala Val Tyr Tyr Cys Ala Arg Glu Gly
        210                 215                 220

Val Thr Asp Gly Met Asp Val Trp Gly Gln Gly Thr Thr Val Thr Val
225                 230                 235                 240

Ser Ser Gly Gly Gly Gly Ser Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
            275                 280                 285

Phe Ala Cys Asp Ile Tyr Ile Trp Ala Pro Leu Ala Gly Thr Cys Gly
        290                 295                 300

Val Leu Leu Leu Ser Leu Val Ile Thr Leu Tyr Cys Lys Arg Gly Arg
305                 310                 315                 320

Lys Lys Leu Leu Tyr Ile Phe Lys Gln Pro Phe Met Arg Pro Val Gln
```

-continued

```
            325             330             335
Thr Thr Gln Glu Glu Asp Gly Cys Ser Cys Arg Phe Pro Glu Glu Glu
            340             345             350

Glu Gly Gly Cys Glu Leu Arg Val Lys Phe Ser Arg Ser Ala Asp Ala
            355             360             365

Pro Ala Tyr Gln Gln Gly Gln Asn Gln Leu Tyr Asn Glu Leu Asn Leu
        370             375             380

Gly Arg Arg Glu Glu Tyr Asp Val Leu Asp Lys Arg Arg Gly Arg Asp
385             390             395             400

Pro Glu Met Gly Gly Lys Pro Arg Arg Lys Asn Pro Gln Glu Gly Leu
            405             410             415

Tyr Asn Glu Leu Gln Lys Asp Lys Met Ala Glu Ala Tyr Ser Glu Ile
            420             425             430

Gly Met Lys Gly Glu Arg Arg Arg Gly Lys Gly His Asp Gly Leu Tyr
            435             440             445

Gln Gly Leu Ser Thr Ala Thr Lys Asp Thr Tyr Asp Ala Leu His Met
        450             455             460

Gln Ala Leu Pro Pro Arg
465             470
```

```
<210> SEQ ID NO 23
<211> LENGTH: 5
<212> TYPE: PRT
<213> ORGANISM: Artificial Sequence
<220> FEATURE:
<223> OTHER INFORMATION: Synthetic

<400> SEQUENCE: 23

Gly Gly Gly Gly Ser
1               5

<210> SEQ ID NO 24
<211> LENGTH: 10
<212> TYPE: PRT
<213> ORGANISM: Artificial Sequence
<220> FEATURE:
<223> OTHER INFORMATION: Synthetic

<400> SEQUENCE: 24

Gly Gly Gly Gly Ser Gly Gly Gly Gly Ser
1               5                   10

<210> SEQ ID NO 25
<211> LENGTH: 15
<212> TYPE: PRT
<213> ORGANISM: Artificial Sequence
<220> FEATURE:
<223> OTHER INFORMATION: Synthetic

<400> SEQUENCE: 25

Gly Gly Gly Gly Ser Gly Gly Gly Gly Ser Gly Gly Gly Gly Ser
1               5                   10                  15

<210> SEQ ID NO 26
<211> LENGTH: 18
<212> TYPE: PRT
<213> ORGANISM: Artificial Sequence
<220> FEATURE:
<223> OTHER INFORMATION: Synthetic

<400> SEQUENCE: 26

Gly Ser Thr Ser Gly Ser Gly Lys Pro Gly Ser Gly Glu Gly Ser Thr
```

```
1               5              10             15

Lys Gly

<210> SEQ ID NO 27
<211> LENGTH: 45
<212> TYPE: PRT
<213> ORGANISM: Artificial Sequence
<220> FEATURE:
<223> OTHER INFORMATION: Synthetic

<400> SEQUENCE: 27

Thr Thr Thr Pro Ala Pro Arg Pro Pro Thr Pro Ala Pro Thr Ile Ala
1               5              10             15

Ser Gln Pro Leu Ser Leu Arg Pro Glu Ala Cys Arg Pro Ala Ala Gly
            20             25             30

Gly Ala Val His Thr Arg Gly Leu Asp Phe Ala Cys Asp
            35             40             45

<210> SEQ ID NO 28
<211> LENGTH: 24
<212> TYPE: PRT
<213> ORGANISM: Artificial Sequence
<220> FEATURE:
<223> OTHER INFORMATION: Synthetic

<400> SEQUENCE: 28

Ile Tyr Ile Trp Ala Pro Leu Ala Gly Thr Cys Gly Val Leu Leu Leu
1               5              10             15

Ser Leu Val Ile Thr Leu Tyr Cys
            20

<210> SEQ ID NO 29
<211> LENGTH: 42
<212> TYPE: PRT
<213> ORGANISM: Artificial Sequence
<220> FEATURE:
<223> OTHER INFORMATION: Synthetic

<400> SEQUENCE: 29

Lys Arg Gly Arg Lys Lys Leu Leu Tyr Ile Phe Lys Gln Pro Phe Met
1               5              10             15

Arg Pro Val Gln Thr Thr Gln Glu Glu Asp Gly Cys Ser Cys Arg Phe
            20             25             30

Pro Glu Glu Glu Glu Gly Gly Cys Glu Leu
            35             40

<210> SEQ ID NO 30
<211> LENGTH: 112
<212> TYPE: PRT
<213> ORGANISM: Artificial Sequence
<220> FEATURE:
<223> OTHER INFORMATION: Synthetic

<400> SEQUENCE: 30

Arg Val Lys Phe Ser Arg Ser Ala Asp Ala Pro Ala Tyr Lys Gln Gly
1               5              10             15

Gln Asn Gln Leu Tyr Asn Glu Leu Asn Leu Gly Arg Arg Glu Glu Tyr
            20             25             30

Asp Val Leu Asp Lys Arg Arg Gly Arg Asp Pro Glu Met Gly Gly Lys
            35             40             45

Pro Arg Arg Lys Asn Pro Gln Glu Gly Leu Tyr Asn Glu Leu Gln Lys
     50             55             60
```

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 31
<211> LENGTH: 1724
<212> TYPE: DNA
<213> ORGANISM: Artificial Sequence
<220> FEATURE:
<223> OTHER INFORMATION: Synthetic

<400> SEQUENCE: 31
agagacaagc gagcttctgc gtctgactcg cagcttgaga ctggcggagg gaagcccgcc        60
caggctctat aaggagacaa ggttctgagc agacaggcca accggaggac aggattccct       120
ggaggccaca gaggagcacc aaggagaaga tctgcctgtg ggtccccatt gcccagcttt       180
tgcctgcact cttgcctgct gccctgacca gagtcatcat gtcttctgag cagaagagtc       240
agcactgcaa gcctgaggaa ggcgttgagg cccaagaaga ggccctgggc ctggtgggtg       300
cacaggctcc tactactgag gagcaggagg ctgctgtctc ctcctcctct cctctggtcc       360
ctggcaccct ggaggaagtg cctgctgctg agtcagcagg tcctccccag agtcctcagg       420
gagcctctgc cttacccact accatcagct tcacttgctg gaggcaaccc aatgagggtt       480
ccagcagcca agaagaggag gggccaagca cctcgcctga cgcagagtcc ttgttccgag       540
aagcactcag taacaaggtg gatgagttgg ctcattttct gctccgcaag tatcgagcca       600
aggagctggt cacaaaggca gaaatgctgg agagagtcat caaaaattac aagcgctgct       660
ttcctgtgat cttcggcaaa gcctccgagt ccctgaagat gatctttggc attgacgtga       720
aggaagtgga ccccgccagc aacacctaca cccttgtcac ctgcctgggc ctttcctatg       780
atggcctgct gggtaataat cagatctttc caagacagg ccttctgata atcgtcctgg        840
gcacaattgc aatggagggc gacagcgcct ctgaggagga aatctgggag gagctgggtg       900
tgatgggggt gtatgatggg agggagcaca ctgtctatgg ggagcccagg aaactgctca       960
cccaagattg ggtgcaggaa aactacctgg agtaccggca ggtacccggc agtaatcctg      1020
cgcgctatga gttcctgtgg ggtccaaggg ctctggctga aaccagctat gtgaaagtcc      1080
tggagcatgt ggtcagggtc aatgcaagag ttcgcattgc ctacccatcc ctgcgtgaag      1140
cagctttgtt agaggaggaa gagggagtct gagcatgagt tgcagccagg gctgtgggga      1200
aggggcaggg ctgggccagt gcatctaaca gccctgtgca gcagcttccc ttgcctcgtg      1260
taacatgagg cccattcttc actctgtttg aagaaaatag tcagtgttct tagtagtggg      1320
tttctatttt gttggatgac ttggagattt atctctgttt cctttacaa ttgttgaaat       1380 gttccttta atggatggtt gaattaactt cagcatccaa gttatgaat cgtagttaac        1440 gtatattgct gttaatatag tttaggagta agagtcttgt tttttattca gattgggaaa      1500
tccgttctat tttgtgaatt tgggacataa aacagcagt ggagtaagta tttagaagtg       1560
tgaattcacc gtgaaatagg tgagataaat taaaagatac ttaattcccg ccttatgcct      1620
cagtctattc tgtaaaattt aaaaaatata tatgcatacc tggatttcct tggcttcgtg      1680
aatgtaagag aaattaaatc tgaataaata attctttctg ttaa                       1724

```
<210> SEQ ID NO 32
<211> LENGTH: 317
<212> TYPE: PRT
<213> ORGANISM: Artificial Sequence
<220> FEATURE:
<223> OTHER INFORMATION: Synthetic

<400> SEQUENCE: 32

Met Ser Ser Glu Gln Lys Ser Gln His Cys Lys Pro Glu Glu Gly Val
1               5                   10                  15

Glu Ala Gln Glu Glu Ala Leu Gly Leu Val Gly Ala Gln Ala Pro Thr
            20                  25                  30

Thr Glu Glu Gln Glu Ala Ala Val Ser Ser Ser Ser Pro Leu Val Pro
        35                  40                  45

Gly Thr Leu Glu Glu Val Pro Ala Ala Glu Ser Ala Gly Pro Pro Gln
    50                  55                  60

Ser Pro Gln Gly Ala Ser Ala Leu Pro Thr Thr Ile Ser Phe Thr Cys
65                  70                  75                  80

Trp Arg Gln Pro Asn Glu Gly Ser Ser Ser Gln Glu Glu Glu Gly Pro
                85                  90                  95

Ser Thr Ser Pro Asp Ala Glu Ser Leu Phe Arg Glu Ala Leu Ser Asn
            100                 105                 110

Lys Val Asp Glu Leu Ala His Phe Leu Leu Arg Lys Tyr Arg Ala Lys
            115                 120                 125

Glu Leu Val Thr Lys Ala Glu Met Leu Glu Arg Val Ile Lys Asn Tyr
    130                 135                 140

Lys Arg Cys Phe Pro Val Ile Phe Gly Lys Ala Ser Glu Ser Leu Lys
145                 150                 155                 160

Met Ile Phe Gly Ile Asp Val Lys Glu Val Asp Pro Ala Ser Asn Thr
                165                 170                 175

Tyr Thr Leu Val Thr Cys Leu Gly Leu Ser Tyr Asp Gly Leu Leu Gly
            180                 185                 190

Asn Asn Gln Ile Phe Pro Lys Thr Gly Leu Leu Ile Ile Val Leu Gly
            195                 200                 205

Thr Ile Ala Met Glu Gly Asp Ser Ala Ser Glu Glu Glu Ile Trp Glu
    210                 215                 220

Glu Leu Gly Val Met Gly Val Tyr Asp Gly Arg Glu His Thr Val Tyr
225                 230                 235                 240

Gly Glu Pro Arg Lys Leu Leu Thr Gln Asp Trp Val Gln Glu Asn Tyr
                245                 250                 255

Leu Glu Tyr Arg Gln Val Pro Gly Ser Asn Pro Ala Arg Tyr Glu Phe
            260                 265                 270

Leu Trp Gly Pro Arg Ala Leu Ala Glu Thr Ser Tyr Val Lys Val Leu
            275                 280                 285

Glu His Val Val Arg Val Asn Ala Arg Val Arg Ile Ala Tyr Pro Ser
    290                 295                 300

Leu Arg Glu Ala Ala Leu Leu Glu Glu Glu Glu Gly Val
305                 310                 315

<210> SEQ ID NO 33
<211> LENGTH: 9
<212> TYPE: PRT
<213> ORGANISM: Artificial Sequence
<220> FEATURE:
<223> OTHER INFORMATION: Synthetic

<400> SEQUENCE: 33
```

-continued

```
Lys Val Leu Glu His Val Val Arg Val
1               5

<210> SEQ ID NO 34
<211> LENGTH: 1437
<212> TYPE: DNA
<213> ORGANISM: Artificial Sequence
<220> FEATURE:
<223> OTHER INFORMATION: Synthetic

<400> SEQUENCE: 34
gacatccaga tgacccagtc tccatcctcc ctgtctgcat ctgtaggaga cagagtcacc     60
atcacttgcc gggcaagtca gagcattagc agctatttaa attggtatca acagaaacca    120
gggaaagccc ctaagctcct gatctatgct gtttccattt tgcaaagtgg ggtcccatca    180
aggttcagtg gcagtggatc tgggacagat ttcactctca ccatcaactc tctgcaacct    240
gaagattttg caacttactc ctgtcaacag acttacagta cccctccgat caccttcggc    300
caagggacac gactggagat taaaggtgga ggcggtagtg gcggaggcgg aagtggtgga    360
ggaggctcag aggtgcagct gttggagtct gggggaggct tggtacaacc tgggggggtcc    420 ctgagactct cctgtgcagc ctctggattc acctttagca gttatgccat gacctgggtc    480
cgccaggctc agggatgggg actggagtgg gtctcagtta ttagtggtag tggtagtgaa    540
acatactacg cagactccgt gaagggccgg ttcaccatct ccagagacaa ttccaaaaac    600
acactgtatc tgcaaatgaa cagcctgaga gccgaagaca cggccgtata ttactgtgtg    660
aaagattctt cgtataggag ctcgtcgagg gcctactact actacggaat ggacgtctgg    720
ggcctaggga ccacggtcac cgtctcctca ggaggtggtg aagtactac cactcctgct     780 ccccgccccc caacacctgc tccaactatt gcatcccaac cactctccct cagacccgaa    840
gcttgtcgcc ccgccgccgg aggtgctgtt cacactagag gactcgattt tgcttgcgac    900
atttatatct gggcccccact tgcaggtact tgcggagtat tgctgctctc acttgttatt    960
actctttatt gcaaacgggg cagaaagaaa ctcctgtata tattcaaaca accatttatg   1020
agaccagtac aaactactca agaggaagat ggctgtagct gccgatttcc agaagaagaa   1080
gaaggaggat gtgaactgag agtgaagttc agcaggagcg cagacgcccc cgcgtacaag   1140
cagggccaga accagctcta taacgagctc aatctaggac gaagagagga gtacgatgtt   1200
ttggacaaga cgtggccg ggaccctgag atggggggaa agccgagaag gaagaaccct    1260
caggaaggcc tgtacaatga actgcagaaa gataagatgg cggaggccta cagtgagatt   1320
gggatgaaag cgagcgccg gaggggcaag gggcacgatg gcctttacca gggtctcagt   1380
acagccacca aggacaccta cgacgccctt cacatgcagg ccctgccccc tcgctaa      1437

<210> SEQ ID NO 35
<211> LENGTH: 478
<212> TYPE: PRT
<213> ORGANISM: Artificial Sequence
<220> FEATURE:
<223> OTHER INFORMATION: Synthetic

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

```
Tyr Ala Val Ser Ile Leu Gln Ser Gly Val Pro Ser Arg Phe Ser Gly
    50                      55                  60

Ser Gly Ser Gly Thr Asp Phe Thr Leu Thr Ile Asn Ser Leu Gln Pro
65                  70                  75                      80

Glu Asp Phe Ala Thr Tyr Ser Cys Gln Gln Thr Tyr Ser Thr Pro Pro
                85                  90                  95

Ile Thr Phe Gly Gln Gly Thr Arg Leu Glu Ile Lys Gly Gly Gly Gly
                100                 105                 110

Ser Gly Gly Gly Gly Ser Gly Gly Gly Ser Glu Val Gln Leu Leu
                115                 120                 125

Glu Ser Gly Gly Gly Leu Val Gln Pro Gly Gly Ser Leu Arg Leu Ser
    130                 135                 140

Cys Ala Ala Ser Gly Phe Thr Phe Ser Ser Tyr Ala Met Thr Trp Val
145                 150                 155                 160

Arg Gln Ala Pro Gly Met Gly Leu Glu Trp Val Ser Val Ile Ser Gly
                165                 170                 175

Ser Gly Ser Glu Thr Tyr Tyr Ala Asp Ser Val Lys Gly Arg Phe Thr
                180                 185                 190

Ile Ser Arg Asp Asn Ser Lys Asn Thr Leu Tyr Leu Gln Met Asn Ser
                195                 200                 205

Leu Arg Ala Glu Asp Thr Ala Val Tyr Tyr Cys Val Lys Asp Ser Ser
    210                 215                 220

Tyr Arg Ser Ser Ser Arg Ala Tyr Tyr Tyr Gly Met Asp Val Trp
225                 230                 235                 240

Gly Leu Gly Thr Thr Val Thr Val Ser Ser Gly Gly Gly Ser Thr
                245                 250                 255

Thr Thr Pro Ala Pro Arg Pro Pro Thr Pro Ala Pro Thr Ile Ala Ser
                260                 265                 270

Gln Pro Leu Ser Leu Arg Pro Glu Ala Cys Arg Pro Ala Ala Gly Gly
    275                 280                 285

Ala Val His Thr Arg Gly Leu Asp Phe Ala Cys Asp Ile Tyr Ile Trp
    290                 295                 300

Ala Pro Leu Ala Gly Thr Cys Gly Val Leu Leu Leu Ser Leu Val Ile
305                 310                 315                 320

Thr Leu Tyr Cys Lys Arg Gly Arg Lys Lys Leu Leu Tyr Ile Phe Lys
                325                 330                 335

Gln Pro Phe Met Arg Pro Val Gln Thr Thr Gln Glu Glu Asp Gly Cys
                340                 345                 350

Ser Cys Arg Phe Pro Glu Glu Glu Glu Gly Gly Cys Glu Leu Arg Val
                355                 360                 365

Lys Phe Ser Arg Ser Ala Asp Ala Pro Ala Tyr Lys Gln Gly Gln Asn
    370                 375                 380

Gln Leu Tyr Asn Glu Leu Asn Leu Gly Arg Arg Glu Glu Tyr Asp Val
385                 390                 395                 400

Leu Asp Lys Arg Arg Gly Arg Asp Pro Glu Met Gly Gly Lys Pro Arg
                405                 410                 415

Arg Lys Asn Pro Gln Glu Gly Leu Tyr Asn Glu Leu Gln Lys Asp Lys
                420                 425                 430

Met Ala Glu Ala Tyr Ser Glu Ile Gly Met Lys Gly Glu Arg Arg Arg
                435                 440                 445

Gly Lys Gly His Asp Gly Leu Tyr Gln Gly Leu Ser Thr Ala Thr Lys
    450                 455                 460
```

Asp Thr Tyr Asp Ala Leu His Met Gln Ala Leu Pro Pro Arg
465                 470                 475

<210> SEQ ID NO 36
<211> LENGTH: 324
<212> TYPE: DNA
<213> ORGANISM: Artificial Sequence
<220> FEATURE:
<223> OTHER INFORMATION: Synthetic

<400> SEQUENCE: 36
gacatccaga tgacccagtc tccatcctcc ctgtctgcat ctgtaggaga cagagtcacc        60
atcacttgcc gggcaagtca gagcattagc agctatttaa attggtatca gcagaaacca       120
gggaaagccc ctaagctcct gatctatgct gcatccagtt tgcaaagtgg ggtcccgtca       180
aggttcagtg gcagtggatc tgggacagat ttcactctca ccatcagcag tctgcaacct       240
gaagattttg caacttacta ctgtcaacag agttacagta cccctccgat caccttcggc       300
caagggacac gactggagat taaa                                             324

<210> SEQ ID NO 37
<211> LENGTH: 108
<212> TYPE: PRT
<213> ORGANISM: Artificial Sequence
<220> FEATURE:
<223> OTHER INFORMATION: Synthetic

<400> SEQUENCE: 37

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 38
<211> LENGTH: 1410
<212> TYPE: DNA
<213> ORGANISM: Artificial Sequence
<220> FEATURE:
<223> OTHER INFORMATION: Synthetic

<400> SEQUENCE: 38
gacatccaga tgacccagtc tccatcctcc ctgtctgcat ctgtaggaga cagagtcacc        60
atcacttgcc gggcaagtca gagcattagc agctatttaa attggtatca gcagaaacca       120
gggaaagccc ctaagctcct gatctatgct gcatccagtt tgcaaagtgg ggtcccgtca       180
aggttcagtg gcagtggatc tgggacagat ttcactctca ccatcagcag tctgcaacct       240
gaagattttg caacttacta ctgtcaacag agttacagta cccctccgat caccttcggc       300
caagggacac gactggagat taaaggtgga ggcggtagtg gcggaggcgg aagtggtgga       360
ggaggctcac aggtgcagct ggtggagtct ggggaggct tggtcaagcc tggagggtcc       420

```
ctgagactct cctgtgcagc ctctggattc actttcagtg aatactacat gacctggatc      480
cgccaggctc cagggcaggg gctggagtgg gtttcataca ttagtagtag tggttttaac      540
atatactacg cagactctgt gaagggccga ttcaccatct caagggacaa cgccaagaac      600
tcactgtttc tgcaaatgaa cagcctgaga gtcgaggaca cggccgtata ttactgtgcg      660
agagaaggtg taacggacgg tatggacgtc tggggccaag ggaccacggt caccgtctcc      720
tcaggaggtg gtggaagtac taccactcct gctccccgcc cccaacacc tgctccaact      780 attgcatccc aaccactctc cctcagaccc gaagcttgtc gccccgccgc cggaggtgct      840
gttcacacta gaggactcga ttttgcttgc gacatttata tctgggcccc acttgcaggt      900
acttgcggag tattgctgct ctcacttgtt attactcttt attgcaaacg gggcagaaag      960
aaactcctgt atatattcaa acaaccattt atgagaccag tacaaactac tcaagaggaa     1020
gatggctgta gctgccgatt ccagaagaa gaagaaggag gatgtgaact gagagtgaag     1080
ttcagcagga gcgcagacgc ccccgcgtac cagcagggcc agaaccagct ctataacgag     1140
ctcaatctag gacgaagaga ggagtacgat gttttggaca agagacgtgg ccgggaccct     1200
gagatggggg gaaagccgag aaggaagaac cctcaggaag gcctgtacaa tgaactgcag     1260
aaagataaga tggcggaggc ctacagtgag attgggatga aaggcgagcg ccggagggggc     1320 aaggggcacg atggccttta ccagggtctc agtacagcca ccaaggacac ctacgacgcc     1380
cttcacatgc aggccctgcc ccctcgctaa                                      1410
```

<210> SEQ ID NO 39
<211> LENGTH: 469
<212> TYPE: PRT
<213> ORGANISM: Artificial Sequence
<220> FEATURE:
<223> OTHER INFORMATION: Synthetic

<400> SEQUENCE: 39

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Gly Gly Gly Gly
            100                 105                 110

Ser Gly Gly Gly Gly Ser Gly Gly Gly Gly Ser Gln Val Gln Leu Val
        115                 120                 125

Glu Ser Gly Gly Gly Leu Val Lys Pro Gly Gly Ser Leu Arg Leu Ser
    130                 135                 140

Cys Ala Ala Ser Gly Phe Thr Phe Ser Glu Tyr Tyr Met Thr Trp Ile
145                 150                 155                 160

Arg Gln Ala Pro Gly Gln Gly Leu Glu Trp Val Ser Tyr Ile Ser Ser
                165                 170                 175

Ser Gly Phe Asn Ile Tyr Tyr Ala Asp Ser Val Lys Gly Arg Phe Thr
```

```
                180                 185                 190
Ile Ser Arg Asp Asn Ala Lys Asn Ser Leu Phe Leu Gln Met Asn Ser
        195                 200                 205

Leu Arg Val Glu Asp Thr Ala Val Tyr Tyr Cys Ala Arg Glu Gly Val
    210                 215                 220

Thr Asp Gly Met Asp Val Trp Gly Gln Gly Thr Thr Val Thr Val Ser
225                 230                 235                 240

Ser Gly Gly Gly Gly Ser Thr Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270

Cys Arg Pro Ala Ala Gly Gly Ala Val His Thr Arg Gly Leu Asp Phe
        275                 280                 285

Ala Cys Asp Ile Tyr Ile Trp Ala Pro Leu Ala Gly Thr Cys Gly Val
    290                 295                 300

Leu Leu Leu Ser Leu Val Ile Thr Leu Tyr Cys Lys Arg Gly Arg Lys
305                 310                 315                 320

Lys Leu Leu Tyr Ile Phe Lys Gln Pro Phe Met Arg Pro Val Gln Thr
                325                 330                 335

Thr Gln Glu Glu Asp Gly Cys Ser Cys Arg Phe Pro Glu Glu Glu Glu
            340                 345                 350

Gly Gly Cys Glu Leu Arg Val Lys Phe Ser Arg Ser Ala Asp Ala Pro
        355                 360                 365

Ala Tyr Gln Gln Gly Gln Asn Gln Leu Tyr Asn Glu Leu Asn Leu Gly
    370                 375                 380

Arg Arg Glu Glu Tyr Asp Val Leu Asp Lys Arg Arg Gly Arg Asp Pro
385                 390                 395                 400

Glu Met Gly Gly Lys Pro Arg Arg Lys Asn Pro Gln Glu Gly Leu Tyr
                405                 410                 415

Asn Glu Leu Gln Lys Asp Lys Met Ala Glu Ala Tyr Ser Glu Ile Gly
            420                 425                 430

Met Lys Gly Glu Arg Arg Arg Gly Lys Gly His Asp Gly Leu Tyr Gln
        435                 440                 445

Gly Leu Ser Thr Ala Thr Lys Asp Thr Tyr Asp Ala Leu His Met Gln
    450                 455                 460

Ala Leu Pro Pro Arg
465
```

```
<210> SEQ ID NO 40
<211> LENGTH: 261
<212> TYPE: PRT
<213> ORGANISM: Artificial Sequence
<220> FEATURE:
<223> OTHER INFORMATION: Synthetic

<400> SEQUENCE: 40

Gly Ser Gly Ala Thr Asn Phe Ser Leu Leu Lys Gln Ala Gly Asp Val
1               5                   10                  15

Glu Glu Asn Pro Gly Pro Met Val Ser Lys Gly Glu Glu Leu Phe Thr
                20                  25                  30

Gly Val Val Pro Ile Leu Val Glu Leu Asp Gly Asp Val Asn Gly His
            35                  40                  45

Lys Phe Ser Val Ser Gly Glu Gly Glu Gly Asp Ala Thr Tyr Gly Lys
    50                  55                  60

Leu Thr Leu Lys Phe Ile Cys Thr Thr Gly Lys Leu Pro Val Pro Trp
```

```
65                   70                   75                   80

Pro Thr Leu Val Thr Thr Leu Thr Tyr Gly Val Gln Cys Phe Ser Arg
                 85                   90                   95

Tyr Pro Asp His Met Lys Gln His Asp Phe Phe Lys Ser Ala Met Pro
             100                 105                 110

Glu Gly Tyr Val Gln Glu Arg Thr Ile Phe Phe Lys Asp Asp Gly Asn
         115                 120                 125

Tyr Lys Thr Arg Ala Glu Val Lys Phe Glu Gly Asp Thr Leu Val Asn
     130                 135                 140

Arg Ile Glu Leu Lys Gly Ile Asp Phe Lys Glu Asp Gly Asn Ile Leu
145                 150                 155                 160

Gly His Lys Leu Glu Tyr Asn Tyr Asn Ser His Asn Val Tyr Ile Met
                 165                 170                 175

Ala Asp Lys Gln Lys Asn Gly Ile Lys Val Asn Phe Lys Ile Arg His
             180                 185                 190

Asn Ile Glu Asp Gly Ser Val Gln Leu Ala Asp His Tyr Gln Gln Asn
             195                 200                 205

Thr Pro Ile Gly Asp Gly Pro Val Leu Leu Pro Asp Asn His Tyr Leu
     210                 215                 220

Ser Thr Gln Ser Ala Leu Ser Lys Asp Pro Asn Glu Lys Arg Asp His
225                 230                 235                 240

Met Val Leu Leu Glu Phe Val Thr Ala Ala Gly Ile Thr Leu Gly Met
                 245                 250                 255

Asp Glu Leu Tyr Lys
             260

<210> SEQ ID NO 41
<211> LENGTH: 39
<212> TYPE: PRT
<213> ORGANISM: Artificial Sequence
<220> FEATURE:
<223> OTHER INFORMATION: Synthetic

<400> SEQUENCE: 41

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
             20                  25                  30

Phe Pro Gly Pro Ser Lys Pro
         35

<210> SEQ ID NO 42
<211> LENGTH: 117
<212> TYPE: DNA
<213> ORGANISM: Artificial Sequence
<220> FEATURE:
<223> OTHER INFORMATION: Synthetic

<400> SEQUENCE: 42
atcgaagtga tgtaccccccc tccatatctg gataacgaga agagcaatgg cacaatcatc      60
cacgtgaagg gcaagcacct gtgcccttct ccactgttcc ccggccctag caagccc         117

<210> SEQ ID NO 43
<211> LENGTH: 27
<212> TYPE: PRT
<213> ORGANISM: Artificial Sequence
<220> FEATURE:
<223> OTHER INFORMATION: Synthetic
```

<400> SEQUENCE: 43

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 44
<211> LENGTH: 81
<212> TYPE: DNA
<213> ORGANISM: Artificial Sequence
<220> FEATURE:
<223> OTHER INFORMATION: Synthetic

<400> SEQUENCE: 44 tttttgggtgc tggtggtggt gggaggcgtg ctggcctgtt actccctgct ggtgaccgtg          60
gccttcatca tctttttgggt g                                                    81

<210> SEQ ID NO 45
<211> LENGTH: 41
<212> TYPE: PRT
<213> ORGANISM: Artificial Sequence
<220> FEATURE:
<223> OTHER INFORMATION: Synthetic

<400> SEQUENCE: 45

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 46
<211> LENGTH: 123
<212> TYPE: DNA
<213> ORGANISM: Artificial Sequence
<220> FEATURE:
<223> OTHER INFORMATION: Synthetic

<400> SEQUENCE: 46
agaagcaaga gatccaggct gctgcactct gactatatga atatgacccc taggcgccca          60
ggccccacaa gaaagcacta ccagccatat gcaccaccta gggacttcgc agcataccgc          120
agc                                                                        123

<210> SEQ ID NO 47
<211> LENGTH: 465
<212> TYPE: PRT
<213> ORGANISM: Artificial Sequence
<220> FEATURE:
<223> OTHER INFORMATION: Synthetic

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

-continued

```
Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Ser Tyr Ser Thr Pro Pro
            85              90              95

Ile Thr Phe Gly Gln Gly Thr Arg Leu Glu Ile Lys Gly Gly Gly Gly
        100             105             110

Ser Gly Gly Gly Gly Ser Gly Gly Gly Ser Gln Val Gln Leu Val
        115             120             125

Glu Ser Gly Gly Gly Leu Val Lys Pro Gly Gly Ser Leu Arg Leu Ser
    130             135             140

Cys Ala Ala Ser Gly Phe Thr Phe Ser Glu Tyr Tyr Met Thr Trp Ile
145             150             155             160

Arg Gln Ala Pro Gly Gln Gly Leu Glu Trp Val Ser Tyr Ile Ser Ser
            165             170             175

Ser Gly Phe Asn Ile Tyr Tyr Ala Asp Ser Val Lys Gly Arg Phe Thr
            180             185             190

Ile Ser Arg Asp Asn Ala Lys Asn Ser Leu Phe Leu Gln Met Asn Ser
        195             200             205

Leu Arg Val Glu Asp Thr Ala Val Tyr Tyr Cys Ala Arg Glu Gly Val
    210             215             220

Thr Asp Gly Met Asp Val Trp Gly Gln Gly Thr Thr Val Thr Val Ser
225             230             235             240

Ser Gly Gly Gly Gly Ser Ile Glu Val Met Tyr Pro Pro Pro Tyr Leu
            245             250             255

Asp Asn Glu Lys Ser Asn Gly Thr Ile Ile His Val Lys Gly Lys His
        260             265             270

Leu Cys Pro Ser Pro Leu Phe Pro Gly Pro Ser Lys Pro Phe Trp Val
        275             280             285

Leu Val Val Val Gly Gly Val Leu Ala Cys Tyr Ser Leu Leu Val Thr
    290             295             300

Val Ala Phe Ile Ile Phe Trp Val Arg Ser Lys Arg Ser Arg Leu Leu
305             310             315             320

His Ser Asp Tyr Met Asn Met Thr Pro Arg Arg Pro Gly Pro Thr Arg
            325             330             335

Lys His Tyr Gln Pro Tyr Ala Pro Pro Arg Asp Phe Ala Ala Tyr Arg
            340             345             350

Ser Arg Val Lys Phe Ser Arg Ser Ala Asp Ala Pro Ala Tyr Gln Gln
        355             360             365

Gly Gln Asn Gln Leu Tyr Asn Glu Leu Asn Leu Gly Arg Arg Glu Glu
    370             375             380

Tyr Asp Val Leu Asp Lys Arg Arg Gly Arg Asp Pro Glu Met Gly Gly
385             390             395             400

Lys Pro Arg Arg Lys Asn Pro Gln Glu Gly Leu Tyr Asn Glu Leu Gln
            405             410             415

Lys Asp Lys Met Ala Glu Ala Tyr Ser Glu Ile Gly Met Lys Gly Glu
        420             425             430

Arg Arg Arg Gly Lys Gly His Asp Gly Leu Tyr Gln Gly Leu Ser Thr
        435             440             445

Ala Thr Lys Asp Thr Tyr Asp Ala Leu His Met Gln Ala Leu Pro Pro
    450             455             460

Arg
465
```

<210> SEQ ID NO 48
<211> LENGTH: 1395
<212> TYPE: DNA
<213> ORGANISM: Artificial Sequence
<220> FEATURE:
<223> OTHER INFORMATION: Synthetic

<400> SEQUENCE: 48
gacatccaga tgacccagag cccaagctcc ctgtccgcct ctgtgggcga tagggtgacc      60
atcacatgcc gggccagcca gtccatctct agctacctga actggtatca gcagaagcca     120
ggcaaggccc ccaagctgct gatctacgca gcatcctctc tgcagtccgg agtgccatct     180
cggttctctg gaagcggatc cggaaccgac tttacccctga caatcagctc cctgcagcct     240
gaggattttg ccacatacta ttgccagcag tcttatagca cccccccat cacattcggc      300 cagggcaccc gcctggagat caagggagga ggaggaagcg gcggaggagg ctccggcggc     360
ggcggctctc aggtgcagct ggtggagagc ggaggaggcc tggtgaagcc tggaggaagc     420
ctgaggctgt cctgtgcagc atctggcttc acctttttccg agtactatat gacatggatc     480
agacaggcac caggacaggg actggagtgg gtgtcctaca tctctagctc cggcttcaat     540
atctactatg ccgactctgt gaagggccgg ttcaccatct ctagggataa cgccaagaat     600
agcctgttcc tgcagatgaa ctccctgcgc gtggaggaca ccgccgtgta ctattgtgca     660
agggagggag tgacagacgg aatggacgtg tggggacagg gaaccacagt gaccgtgtct     720
agcggaggag gaggatctat cgaagtgatg tacccacccc cttatctgga taacgagaag     780
agcaatggca caatcatcca cgtgaagggc aagcacctgt gccctctcc tctgttccca      840 ggccccagca agccattttg ggtgctggtg gtggtgggag gcgtgctggc ctgttactcc     900
ctgctggtga ccgtggcctt catcatcttt tgggtgagat ctaagcgcag ccggctgctg     960
cactctgact atatgaatat gaccccacgg agacctggcc caacaagaaa gcactaccag     1020
ccatatgcac caccaaggga cttcgcagcc tacagaagca gggtgaagtt ttccaggtct     1080
gccgatgcac cagcatacca gcaggacag aaccagctgt ataacgagct gaatctgggc     1140
aggcgcgagg agtatgacgt gctggataag aggagaggcc gcgatcctga gatgggaggc     1200
aagccaaggc gcaagaaccc tcaggagggc ctgtacaatg agctgcagaa ggacaagatg     1260
gccgaggcct atagcgagat cggcatgaag ggagagcgga aaggggcaa gggacacgat     1320 ggcctgtacc agggcctgtc caccgccaca aaggacacct atgatgccct gcacatgcag     1380
gccctgcctc caagg                                                      1395

<210> SEQ ID NO 49
<211> LENGTH: 10
<212> TYPE: PRT
<213> ORGANISM: Artificial Sequence
<220> FEATURE:
<223> OTHER INFORMATION: Synthetic

<400> SEQUENCE: 49

Gly Val Tyr Asn Gly Arg Glu His Thr Val
1               5                   10

<210> SEQ ID NO 50
<211> LENGTH: 363
<212> TYPE: DNA
<213> ORGANISM: Artificial Sequence
<220> FEATURE:
<223> OTHER INFORMATION: Synthetic

<400> SEQUENCE: 50

```
gaagtgcagc tggtggagtc tggggggaggc ttggtacagc ctggcaggtc cctgagactc        60
tcctgcgcag cctctggatt cacctttgat gattatgcca tgcactgggt ccggcaagct       120
ccagggaagg gcctggagtg ggtctcaggt atcagttgga atagtggtag catagcctat       180
gcggactctg tgaagggccg attcaccatc tccagagaca cgccaagaa ctccctgtat        240 ctgcaaatga acagtctgag aagtgaggac acggccttgt atcactgtgc aaaagattgg       300
cgaagaacca attactacgg tatggacgtc tggggccaag ggaccacggt caccgtctcc       360
tca                                                                     363
```

```
<210> SEQ ID NO 51
<211> LENGTH: 121
<212> TYPE: PRT
<213> ORGANISM: Artificial Sequence
<220> FEATURE:
<223> OTHER INFORMATION: Synthetic

<400> SEQUENCE: 51

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ser Glu Asp Thr Ala Leu Tyr His Cys
                85                  90                  95

Ala Lys Asp Trp Arg Arg Thr Asn Tyr Tyr Gly Met Asp Val Trp Gly
            100                 105                 110

Gln Gly Thr Thr Val Thr Val Ser Ser
        115                 120
```

```
<210> SEQ ID NO 52
<211> LENGTH: 24
<212> TYPE: DNA
<213> ORGANISM: Artificial Sequence
<220> FEATURE:
<223> OTHER INFORMATION: Synthetic

<400> SEQUENCE: 52
ggattcacct ttgatgatta tgcc                                              24
```

```
<210> SEQ ID NO 53
<211> LENGTH: 8
<212> TYPE: PRT
<213> ORGANISM: Artificial Sequence
<220> FEATURE:
<223> OTHER INFORMATION: Synthetic

<400> SEQUENCE: 53

Gly Phe Thr Phe Asp Asp Tyr Ala
1               5
```

```
<210> SEQ ID NO 54
<211> LENGTH: 24
<212> TYPE: DNA
<213> ORGANISM: Artificial Sequence
```

```
<220> FEATURE:
<223> OTHER INFORMATION: Synthetic

<400> SEQUENCE: 54
atcagttgga atagtggtag cata                                              24

<210> SEQ ID NO 55
<211> LENGTH: 8
<212> TYPE: PRT
<213> ORGANISM: Artificial Sequence
<220> FEATURE:
<223> OTHER INFORMATION: Synthetic

<400> SEQUENCE: 55

Ile Ser Trp Asn Ser Gly Ser Ile
1               5

<210> SEQ ID NO 56
<211> LENGTH: 42
<212> TYPE: DNA
<213> ORGANISM: Artificial Sequence
<220> FEATURE:
<223> OTHER INFORMATION: Synthetic

<400> SEQUENCE: 56
gcaaaagatt ggcgaagaac caattactac ggtatggacg tc                        42

<210> SEQ ID NO 57
<211> LENGTH: 14
<212> TYPE: PRT
<213> ORGANISM: Artificial Sequence
<220> FEATURE:
<223> OTHER INFORMATION: Synthetic

<400> SEQUENCE: 57

Ala Lys Asp Trp Arg Arg Thr Asn Tyr Tyr Gly Met Asp Val
1               5                   10

<210> SEQ ID NO 58
<211> LENGTH: 321
<212> TYPE: DNA
<213> ORGANISM: Artificial Sequence
<220> FEATURE:
<223> OTHER INFORMATION: Synthetic

<400> SEQUENCE: 58
gacatccaga tgacccagtc tccatcctcc ctgtctgcat ctgtaggaga cagagtcacc     60
atcacttgcc aggcgagtca ggacattagc aactatttaa attggtatca gcaaaaacga    120
gggaaagccc ctaagctcct gatctacgat gcatccattt ggaaacagg ggtcccatca     180 aggttcagtg aagtggatc tgggacagat tttactttca ccatcagcag cctgcagcct     240
gaagatattg caacatattt ctgtcaacag tttgataatg tcccgctcac tttcggcgga    300
gggaccaagg tggagatcaa a                                               321

<210> SEQ ID NO 59
<211> LENGTH: 107
<212> TYPE: PRT
<213> ORGANISM: Artificial Sequence
<220> FEATURE:
<223> OTHER INFORMATION: Synthetic

<400> SEQUENCE: 59

Asp Ile Gln Met Thr Gln Ser Pro Ser Ser Leu Ser Ala Ser Val Gly
1               5                   10                  15
```

-continued

```
Asp Arg Val Thr Ile Thr Cys Gln Ala Ser Gln Asp Ile Ser Asn Tyr
        20                  25                  30

Leu Asn Trp Tyr Gln Gln Lys Arg Gly Lys Ala Pro Lys Leu Leu Ile
        35                  40                  45

Tyr Asp Ala Ser Ile Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Phe Asp Asn Val Pro Leu
                85                  90                  95

Thr Phe Gly Gly Gly Thr Lys Val Glu Ile Lys
            100                 105
```

<210> SEQ ID NO 60
<211> LENGTH: 18
<212> TYPE: DNA
<213> ORGANISM: Artificial Sequence
<220> FEATURE:
<223> OTHER INFORMATION: Synthetic

<400> SEQUENCE: 60
caggacatta gcaactat                                                                      18

<210> SEQ ID NO 61
<211> LENGTH: 6
<212> TYPE: PRT
<213> ORGANISM: Artificial Sequence
<220> FEATURE:
<223> OTHER INFORMATION: Synthetic

<400> SEQUENCE: 61

```
Gln Asp Ile Ser Asn Tyr
1               5
```

<210> SEQ ID NO 62
<211> LENGTH: 9
<212> TYPE: DNA
<213> ORGANISM: Artificial Sequence
<220> FEATURE:
<223> OTHER INFORMATION: Synthetic

<400> SEQUENCE: 62 gatgcatcc                                                                                 9

<210> SEQ ID NO 63
<211> LENGTH: 3
<212> TYPE: PRT
<213> ORGANISM: Artificial Sequence
<220> FEATURE:
<223> OTHER INFORMATION: Synthetic

<400> SEQUENCE: 63

```
Asp Ala Ser
1
```

<210> SEQ ID NO 64
<211> LENGTH: 27
<212> TYPE: DNA
<213> ORGANISM: Artificial Sequence
<220> FEATURE:
<223> OTHER INFORMATION: Synthetic

<400> SEQUENCE: 64
caacagtttg ataatgtccc gctcact                                        27

<210> SEQ ID NO 65
<211> LENGTH: 9
<212> TYPE: PRT
<213> ORGANISM: Artificial Sequence
<220> FEATURE:
<223> OTHER INFORMATION: Synthetic

<400> SEQUENCE: 65

Gln Gln Phe Asp Asn Val Pro Leu Thr
1               5

<210> SEQ ID NO 66
<211> LENGTH: 1344
<212> TYPE: DNA
<213> ORGANISM: Artificial Sequence
<220> FEATURE:
<223> OTHER INFORMATION: Synthetic

<400> SEQUENCE: 66
gaagtgcagc tggtggagtc tgggggaggc ttggtacagc ctggcaggtc cctgagactc      60
tcctgcgcag cctctggatt cacctttgat gattatgcca tgcactgggt ccggcaagct     120
ccagggaagg gcctggagtg ggtctcaggt atcagttgga atagtggtag catagcctat     180
gcggactctg tgaagggccg attcaccatc tccagagaca cgccaagaa ctccctgtat      240 ctgcaaatga acagtctgag aagtgaggac acggccttgt atcactgtgc aaaagattgg     300
cgaagaacca attactacgg tatgacgtc tggggccaag ggaccacggt caccgtctcc      360
tcagcctcca ccaagggccc atcggtcttc cccctggcgc cctgctccag gagcacctcc     420
gagagcacag ccgccctggg ctgcctggtc aaggactact ccccgaacc ggtgacggtg      480 tcgtggaact caggcgccct gaccagcggc gtgcacacct ccccggctgt cctacagtcc     540
tcaggactct actccctcag cagcgtggtg accgtgccct ccagcagctt gggcacgaag     600
acctacacct gcaacgtaga tcacaagccc agcaacacca aggtggacaa gagagttgag     660
tccaaatatg gtcccccatg cccaccgtgc ccagcaccac ctgtggcagg accatcagtc     720
ttcctgttcc ccccaaaacc caaggacact ctcatgatct cccggacccc tgaggtcacg     780
tgcgtggtgg tggacgtgag ccaggaagac cccgaggtcc agttcaactg gtacgtggat     840
ggcgtggagg tgcataatgc caagacaaag ccgcgggagg agcagttcaa cagcacgtac     900
cgtgtggtca gcgtcctcac cgtcctgcac caggactggc tgaacggcaa ggagtacaag     960
tgcaaggtct ccaacaaagg cctcccgtcc tccatcgaga aaaccatctc caaagccaaa    1020
gggcagcccc gagagccaca ggtgtacacc ctgcccccat cccaggagga gatgaccaag    1080
aaccaggtca gcctgacctg cctggtcaaa ggcttctacc ccagcgacat cgccgtggag    1140
tgggagagca atgggcagcc ggagaacaac tacaagacca cgcctcccgt gctggactcc    1200
gacggctcct tcttcctcta cagcaggctc accgtggaca gagcaggtg gcaggagggg     1260 aatgtcttct catgctccgt gatgcatgag gctctgcaca accactacac acagaagtcc    1320
ctctccctgt ctctgggtaa atga                                          1344

<210> SEQ ID NO 67
<211> LENGTH: 447
<212> TYPE: PRT
<213> ORGANISM: Artificial Sequence
<220> FEATURE:
<223> OTHER INFORMATION: Synthetic

```
<400> SEQUENCE: 67

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ser Glu Asp Thr Ala Leu Tyr His Cys
                85                  90                  95

Ala Lys Asp Trp Arg Arg Thr Asn Tyr Tyr Gly Met Asp Val Trp Gly
            100                 105                 110

Gln Gly Thr Thr Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415
```

Trp Gln Glu Gly Asn Val Phe Ser Cys Ser Val Met His Glu Ala Leu
            420                 425             430

His Asn His Tyr Thr Gln Lys Ser Leu Ser Leu Ser Leu Gly Lys
        435                 440             445

<210> SEQ ID NO 68
<211> LENGTH: 645
<212> TYPE: DNA
<213> ORGANISM: Artificial Sequence
<220> FEATURE:
<223> OTHER INFORMATION: Synthetic

<400> SEQUENCE: 68
gacatccaga tgacccagtc tccatcctcc ctgtctgcat ctgtaggaga cagagtcacc        60
atcacttgcc aggcgagtca ggacattagc aactatttaa attggtatca gcaaaaacga       120
gggaaagccc ctaagctcct gatctacgat gcatccattt tggaaacagg ggtcccatca       180
aggttcagtg gaagtggatc tgggacagat tttactttca ccatcagcag cctgcagcct       240
gaagatattg caacatattt ctgtcaacag tttgataatg tcccgctcac tttcggcgga       300
gggaccaagg tggagatcaa acgaactgtg gctgcaccat ctgtcttcat cttcccgcca       360
tctgatgagc agttgaaatc tggaactgcc tctgttgtgt gcctgctgaa taacttctat       420
cccagagagg ccaaagtaca gtggaaggtg gataacgccc tccaatcggg taactcccag       480
gagagtgtca cagagcagga cagcaaggac agcacctaca gcctcagcag caccctgacg       540
ctgagcaaag cagactacga gaaacacaaa gtctacgcct gcgaagtcac ccatcagggc       600
ctgagctcgc ccgtcacaaa gagcttcaac aggggagagt gttag                       645

<210> SEQ ID NO 69
<211> LENGTH: 214
<212> TYPE: PRT
<213> ORGANISM: Artificial Sequence
<220> FEATURE:
<223> OTHER INFORMATION: Synthetic

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Arg Gly Lys Ala Pro Lys Leu Leu Ile
        35                  40                  45

Tyr Asp Ala Ser Ile Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Phe Asp Asn Val Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

-continued

```
Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
        195             200             205

Phe Asn Arg Gly Glu Cys
    210
```

```
<210> SEQ ID NO 70
<211> LENGTH: 1413
<212> TYPE: DNA
<213> ORGANISM: Artificial Sequence
<220> FEATURE:
<223> OTHER INFORMATION: Synthetic

<400> SEQUENCE: 70
gacatccaga tgacccagag cccaagctcc ctgagcgcct ccgtgggcga ccgggtgaca     60
atcacctgcc aggccagcca ggatatctcc aactacctga attggtatca gcagaagagg    120
ggcaaggccc ccaagctgct gatctacgac gcctctatcc tggagacagg cgtgcctagc    180
cgcttttctg gaagcggatc cggaaccgac ttcaccttca ccatctctag cctgcagcca    240
gaggacatcg ccacctattt ctgccagcag tttgataatg tgcccctgac attcggcggc    300
ggcaccaagg tggagatcaa gggaggagga ggatccggag gaggaggatc tggcggcggc    360
ggcagcgagg tgcagctggt ggagagcggc ggcggcctgg tgcagccagg cagatctctg    420
aggctgagct gtgccgcctc cggcttcaca tttgacgatt acgccatgca ctgggtgcgg    480
caggcaccag gcaagggact ggagtgggtg tctggcatca gctggaactc tggcagcatc    540
gcctatgccg actccgtgaa gggccgcttt accatcagcc gggataacgc caagaattcc    600
ctgtacctgc agatgaattc cctgagatct gaggacacag ccctgtatca ctgcgccaag    660
gattggcgga gaaccaacta ctatggcatg acgtgtggg gccagggcac cacagtgaca    720
gtgtcctctg gaggaggagg atccaccaca accctgcac acggcccccc taccagca      780 cctaccatcg cctctcagcc actgagcctg agaccagagg catgtaggcc tgcagcagga    840
ggagccgtgc acaccagagg cctggacttc gcctgcgata tctacatctg ggcacctctg    900
gcaggaacat gtggcgtgct gctgctgagc ctggtcatca ccctgtactg caagcgcggc    960
cggaagaagc tgctgtatat cttcaagcag ccttttatgc ggccagtgca gacaacccag   1020
gaggaggacg gctgctcttg tagattccct gaagaagagg agggaggatg tgagctgagg   1080
gtgaagtttt cccggtctgc cgatgcacca gcataccagc agggacagaa ccagctgtat   1140
aacgagctga atctgggcag gcgcgaggag tacgacgtgc tggataagcg gagaggcagg   1200
gatccagaga tgggcggcaa gccaaggcgc aagaacccc aggagggcct gtacaatgag    1260
ctgcagaagg acaagatggc cgaggcctat agcgagatcg gcatgaaggg agagcggaga   1320
aggggcaagg gacacgatgg cctgtaccag ggcctgtcca gccaccaa ggacacatat      1380 gatgccctgc acatgcaggc cctgccacca agg                                1413
```

```
<210> SEQ ID NO 71
<211> LENGTH: 471
<212> TYPE: PRT
<213> ORGANISM: Artificial Sequence
<220> FEATURE:
<223> OTHER INFORMATION: Synthetic

<400> SEQUENCE: 71
```

-continued

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Arg Gly Lys Ala Pro Lys Leu Leu Ile
        35                  40                  45

Tyr Asp Ala Ser Ile Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Phe Asp Asn Val Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Glu Val Gln Leu Val Glu
            115                 120                 125

Ser Gly Gly Gly Leu Val Gln Pro Gly Arg Ser Leu Arg Leu Ser Cys
        130                 135                 140

Ala Ala Ser Gly Phe Thr Phe Asp Asp Tyr Ala Met His Trp Val Arg
145                 150                 155                 160

Gln Ala Pro Gly Lys Gly Leu Glu Trp Val Ser Gly Ile Ser Trp Asn
            165                 170                 175

Ser Gly Ser Ile Ala Tyr Ala Asp Ser Val Lys Gly Arg Phe Thr Ile
            180                 185                 190

Ser Arg Asp Asn Ala Lys Asn Ser Leu Tyr Leu Gln Met Asn Ser Leu
        195                 200                 205

Arg Ser Glu Asp Thr Ala Leu Tyr His Cys Ala Lys Asp Trp Arg Arg
    210                 215                 220

Thr Asn Tyr Tyr Gly Met Asp Val Trp Gly Gln Gly Thr Thr Val Thr
225                 230                 235                 240

Val Ser Ser Gly Gly Gly Gly Ser Thr Thr Thr Pro Ala Pro Arg Pro
            245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
            275                 280                 285

Asp Phe Ala Cys Asp Ile Tyr Ile Trp Ala Pro Leu Ala Gly Thr Cys
    290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
            325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
            355                 360                 365

Ala Pro Ala Tyr Gln Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415
```

-continued

```
Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470
```

<210> SEQ ID NO 72
<211> LENGTH: 1401
<212> TYPE: DNA
<213> ORGANISM: Artificial Sequence
<220> FEATURE:
<223> OTHER INFORMATION: Synthetic

<400> SEQUENCE: 72

```
gacatccaga tgacccagag cccaagctcc ctgagcgcct ccgtgggcga ccgggtgacc      60
atcacatgcc aggcctctca ggatatcagc aactacctga attggtatca gcagaagagg     120
ggcaaggccc caaagctgct gatctacgac gcatccatcc tggagaccgg agtgccatct     180
cgcttttctg gcagcggctc cggcacagat ttcacctttta caatctctag cctgcagcct     240
gaggacatcg ccacctattt ctgccagcag tttgataatg tgccactgac cttcggcggc     300
ggcacaaagg tggagatcaa gggaggagga ggatccggag gaggaggatc tggcggcggc     360
ggcagcgagg tgcagctggt ggagagcggc ggcggcctgg tgcagccagg cagatccctg     420
aggctgtctt gtgccgccag cggcttcacc tttgacgatt acgccatgca ctgggtgcgg     480
caggcaccag gcaagggact ggagtgggtg tctggcatca gctggaactc tggcagcatc     540
gcctatgccg actccgtgaa gggccgcttc acaatcagcc gggataacgc caagaattcc     600
ctgtacctgc agatgaattc cctgagatct gaggacaccg ccctgtatca ctgtgccaag     660
gattggcgga acaaaacta ctatggcatg gacgtgtggg gccagggcac cacagtgacc     720
gtgtcctctg gaggaggagg atctatcgaa gtgatgtacc ccctccata tctggataac     780 gagaagagca atggcacaat catccacgtg aagggcaagc acctgtgccc ttctccactg     840
ttccccggcc ctagcaagcc ctttttgggtg ctggtggtgg tgggaggcgt gctggcctgt     900
tactccctgc tggtgaccgt ggccttcatc atcttttggg tgagaagcaa gagatccagg     960
ctgctgcact ctgactatat gaatatgacc cctaggcgcc caggccccac aagaaagcac    1020
taccagccat atgcaccacc tagggacttc gcagcatacc gcagcagggt gaagttttcc    1080
cggtctgccg atgcacctgc ataccagcag ggacagaacc agctgtataa cgagctgaat    1140
ctgggccgga gagaggagta tgacgtgctg ataaagaggc gcggcagaga tccagagatg    1200
ggcggcaagc cacggagaaa gaaccccccag gagggcctgt acaatgagct gcagaaggac    1260
aagatggccg aggcctatag cgagatcggc atgaagggag agaggcgccg gggcaaggga    1320
cacgatggcc tgtaccaggg cctgtccacc gccacaaagg acacctatga tgcactgcac    1380
atgcaggccc tgccaccaag g                                               1401
```

<210> SEQ ID NO 73
<211> LENGTH: 467
<212> TYPE: PRT
<213> ORGANISM: Artificial Sequence
<220> FEATURE:
<223> OTHER INFORMATION: Synthetic

<400> SEQUENCE: 73

-continued

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Arg Gly Lys Ala Pro Lys Leu Leu Ile
        35                  40                  45

Tyr Asp Ala Ser Ile Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Phe Asp Asn Val Pro Leu
            85                  90                  95

Thr Phe Gly Gly Gly Thr Lys Val Glu Ile Lys Gly Gly Gly Gly Ser
        100                 105                 110

Gly Gly Gly Gly Ser Gly Gly Gly Ser Glu Val Gln Leu Val Glu
        115                 120                 125

Ser Gly Gly Gly Leu Val Gln Pro Gly Arg Ser Leu Arg Leu Ser Cys
    130                 135                 140

Ala Ala Ser Gly Phe Thr Phe Asp Asp Tyr Ala Met His Trp Val Arg
145                 150                 155                 160

Gln Ala Pro Gly Lys Gly Leu Glu Trp Val Ser Gly Ile Ser Trp Asn
            165                 170                 175

Ser Gly Ser Ile Ala Tyr Ala Asp Ser Val Lys Gly Arg Phe Thr Ile
        180                 185                 190

Ser Arg Asp Asn Ala Lys Asn Ser Leu Tyr Leu Gln Met Asn Ser Leu
        195                 200                 205

Arg Ser Glu Asp Thr Ala Leu Tyr His Cys Ala Lys Asp Trp Arg Arg
    210                 215                 220

Thr Asn Tyr Tyr Gly Met Asp Val Trp Gly Gln Gly Thr Thr Val Thr
225                 230                 235                 240

Val Ser Ser Gly Gly Gly Gly Ser Ile Glu Val Met Tyr Pro Pro Pro
            245                 250                 255

Tyr Leu Asp Asn Glu Lys Ser Asn Gly Thr Ile Ile His Val Lys Gly
            260                 265                 270

Lys His Leu Cys Pro Ser Pro Leu Phe Pro Gly Pro Ser Lys Pro Phe
        275                 280                 285

Trp Val Leu Val Val Val Gly Gly Val Leu Ala Cys Tyr Ser Leu Leu
    290                 295                 300

Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
            325                 330                 335

Thr Arg Lys His Tyr Gln Pro Tyr Ala Pro Pro Arg Asp Phe Ala Ala
            340                 345                 350

Tyr Arg Ser Arg Val Lys Phe Ser Arg Ser Ala Asp Ala Pro Ala Tyr
        355                 360                 365

Gln Gln Gly Gln Asn Gln Leu Tyr Asn Glu Leu Asn Leu Gly Arg Arg
    370                 375                 380

Glu Glu Tyr Asp Val Leu Asp Lys Arg Arg Gly Arg Asp Pro Glu Met
385                 390                 395                 400

Gly Gly Lys Pro Arg Arg Lys Asn Pro Gln Glu Gly Leu Tyr Asn Glu
            405                 410                 415
```

Leu Gln Lys Asp Lys Met Ala Glu Ala Tyr Ser Glu Ile Gly Met Lys
            420                 425                 430

Gly Glu Arg Arg Arg Gly Lys Gly His Asp Gly Leu Tyr Gln Gly Leu
            435                 440                 445

Ser Thr Ala Thr Lys Asp Thr Tyr Asp Ala Leu His Met Gln Ala Leu
    450                 455                 460

Pro Pro Arg
465

<210> SEQ ID NO 74
<211> LENGTH: 466
<212> TYPE: PRT
<213> ORGANISM: Artificial Sequence
<220> FEATURE:
<223> OTHER INFORMATION: Synthetic

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg Gly Gly Gly
            100                 105                 110

Gly Ser Gly Gly Gly Gly Ser Gly Gly Gly Ser Gln Val Gln Leu
            115                 120                 125

Val Glu Ser Gly Gly Gly Leu Val Lys Pro Gly Gly Ser Leu Arg Leu
    130                 135                 140

Ser Cys Ala Ala Ser Gly Phe Thr Phe Ser Glu Tyr Tyr Met Thr Trp
145                 150                 155                 160

Ile Arg Gln Ala Pro Gly Gln Gly Leu Glu Trp Val Ser Tyr Ile Ser
            165                 170                 175

Ser Ser Gly Phe Asn Ile Tyr Tyr Ala Asp Ser Val Lys Gly Arg Phe
            180                 185                 190

Thr Ile Ser Arg Asp Asn Ala Lys Asn Ser Leu Phe Leu Gln Met Asn
            195                 200                 205

Ser Leu Arg Val Glu Asp Thr Ala Val Tyr Tyr Cys Ala Arg Glu Gly
    210                 215                 220

Val Thr Asp Gly Met Asp Val Trp Gly Gln Gly Thr Thr Val Thr Val
225                 230                 235                 240

Ser Ser Gly Gly Gly Gly Ser Ile Glu Val Met Tyr Pro Pro Pro Tyr
            245                 250                 255

Leu Asp Asn Glu Lys Ser Asn Gly Thr Ile Ile His Val Lys Gly Lys
            260                 265                 270

His Leu Cys Pro Ser Pro Leu Phe Pro Gly Pro Ser Lys Pro Phe Trp
            275                 280                 285

Val Leu Val Val Val Gly Gly Val Leu Ala Cys Tyr Ser Leu Leu Val
    290                 295                 300

-continued

```
Thr Val Ala Phe Ile Ile Phe Trp Val Arg Ser Lys Arg Ser Arg Leu
305             310             315             320

Leu His Ser Asp Tyr Met Asn Met Thr Pro Arg Arg Pro Gly Pro Thr
            325             330             335

Arg Lys His Tyr Gln Pro Tyr Ala Pro Pro Arg Asp Phe Ala Ala Tyr
            340             345             350

Arg Ser Arg Val Lys Phe Ser Arg Ser Ala Asp Ala Pro Ala Tyr Gln
            355             360             365

Gln Gly Gln Asn Gln Leu Tyr Asn Glu Leu Asn Leu Gly Arg Arg Glu
        370             375             380

Glu Tyr Asp Val Leu Asp Lys Arg Arg Gly Arg Asp Pro Glu Met Gly
385             390             395             400

Gly Lys Pro Arg Arg Lys Asn Pro Gln Glu Gly Leu Tyr Asn Glu Leu
            405             410             415

Gln Lys Asp Lys Met Ala Glu Ala Tyr Ser Glu Ile Gly Met Lys Gly
            420             425             430

Glu Arg Arg Arg Gly Lys Gly His Asp Gly Leu Tyr Gln Gly Leu Ser
            435             440             445

Thr Ala Thr Lys Asp Thr Tyr Asp Ala Leu His Met Gln Ala Leu Pro
    450             455             460

Pro Arg
465
```

```
<210> SEQ ID NO 75
<211> LENGTH: 1398
<212> TYPE: DNA
<213> ORGANISM: Artificial Sequence
<220> FEATURE:
<223> OTHER INFORMATION: Synthetic

<400> SEQUENCE: 75
gacatccaga tgacccagag cccaagctcc ctgtccgcct ctgtgggcga tagggtgacc      60
atcacatgcc gggccagcca gtccatctct agctacctga actggtatca gcagaagcca     120
ggcaaggccc ccaagctgct gatctacgca gcatcctctc tgcagtccgg agtgccatct     180
cggttctctg gaagcggatc cggaaccgac tttaccctga caatcagctc cctgcagcct     240
gaggattttg ccacatacta ttgccagcag tcttatagca cccccccctat cacattcggc     300 cagggcaccc gcctggagat caagagggga ggaggaggaa gcggcggagg aggctccggc     360
ggcggcggct ctcaggtgca gctggtggag agcggaggag gcctggtgaa gcctggagga     420
agcctgaggc tgtcctgtgc agcatctggc ttcacctttt ccgagtacta tatgacatgg     480
atcagacagg caccaggaca gggactggag tgggtgtcct acatctctag ctccggcttc     540
aatatctact atgccgactc tgtgaagggc cggttcacca tctctaggga taacgccaag     600
aatagcctgt tcctgcagat gaactccctg cgcgtggagg acaccgccgt gtactattgt     660
gcaagggagg gagtgacaga cggaatggac gtgtggggac agggaaccac agtgaccgtg     720
tctagcggag gaggaggatc tatcgaagtg atgtacccac cccttatct ggataacgag     780 aagagcaatg gcacaatcat ccacgtgaag ggcaagcacc tgtgcccctc tcctctgttc     840
ccaggcccca gcaagccatt ttgggtgctg gtggtggtgg gaggcgtgct ggcctgttac     900
tccctgctgg tgaccgtggc cttcatcatc ttttgggtga atctaagcg cagccggctg     960 ctgcactctg actatatgaa tatgacccca cggagacctg gcccaacaag aaagcactac    1020
cagccatatg caccaccaag ggacttcgca gcctacagaa gcagggtgaa gttttccagg    1080
```

```
tctgccgatg caccagcata ccagcaggga cagaaccagc tgtataacga gctgaatctg    1140
ggcaggcgcg aggagtatga cgtgctggat aagaggagag gccgcgatcc tgagatggga    1200
ggcaagccaa ggcgcaagaa ccctcaggag ggcctgtaca atgagctgca gaaggacaag    1260
atggccgagg cctatagcga gatcggcatg aagggagagc ggagaagggg caagggacac    1320
gatggcctgt accagggcct gtccaccgcc acaaaggaca cctatgatgc cctgcacatg    1380
caggccctgc ctccaagg                                                  1398
```

<210> SEQ ID NO 76
<211> LENGTH: 730
<212> TYPE: PRT
<213> ORGANISM: Artificial Sequence
<220> FEATURE:
<223> OTHER INFORMATION: Synthetic

<400> SEQUENCE: 76

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Gly Gly Gly Gly
            100                 105                 110

Ser Gly Gly Gly Gly Ser Gly Gly Gly Ser Gln Val Gln Leu Val
        115                 120                 125

Glu Ser Gly Gly Gly Leu Val Lys Pro Gly Gly Ser Leu Arg Leu Ser
    130                 135                 140

Cys Ala Ala Ser Gly Phe Thr Phe Ser Glu Tyr Tyr Met Thr Trp Ile
145                 150                 155                 160

Arg Gln Ala Pro Gly Gln Gly Leu Glu Trp Val Ser Tyr Ile Ser Ser
                165                 170                 175

Ser Gly Phe Asn Ile Tyr Tyr Ala Asp Ser Val Lys Gly Arg Phe Thr
            180                 185                 190

Ile Ser Arg Asp Asn Ala Lys Asn Ser Leu Phe Leu Gln Met Asn Ser
        195                 200                 205

Leu Arg Val Glu Asp Thr Ala Val Tyr Tyr Cys Ala Arg Glu Gly Val
    210                 215                 220

Thr Asp Gly Met Asp Val Trp Gly Gln Gly Thr Thr Val Thr Val Ser
225                 230                 235                 240

Ser Gly Gly Gly Gly Ser Thr Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270

Cys Arg Pro Ala Ala Gly Gly Ala Val His Thr Arg Gly Leu Asp Phe
        275                 280                 285

Ala Cys Asp Ile Tyr Ile Trp Ala Pro Leu Ala Gly Thr Cys Gly Val
    290                 295                 300
```

-continued

```
Leu Leu Leu Ser Leu Val Ile Thr Leu Tyr Cys Lys Arg Gly Arg Lys
305             310             315             320

Lys Leu Leu Tyr Ile Phe Lys Gln Pro Phe Met Arg Pro Val Gln Thr
            325             330             335

Thr Gln Glu Glu Asp Gly Cys Ser Cys Arg Phe Pro Glu Glu Glu Glu
            340             345             350

Gly Gly Cys Glu Leu Arg Val Lys Phe Ser Arg Ser Ala Asp Ala Pro
            355             360             365

Ala Tyr Gln Gln Gly Gln Asn Gln Leu Tyr Asn Glu Leu Asn Leu Gly
    370             375             380

Arg Arg Glu Glu Tyr Asp Val Leu Asp Lys Arg Arg Gly Arg Asp Pro
385             390             395             400

Glu Met Gly Gly Lys Pro Arg Arg Lys Asn Pro Gln Glu Gly Leu Tyr
            405             410             415

Asn Glu Leu Gln Lys Asp Lys Met Ala Glu Ala Tyr Ser Glu Ile Gly
            420             425             430

Met Lys Gly Glu Arg Arg Arg Gly Lys Gly His Asp Gly Leu Tyr Gln
            435             440             445

Gly Leu Ser Thr Ala Thr Lys Asp Thr Tyr Asp Ala Leu His Met Gln
    450             455             460

Ala Leu Pro Pro Arg Gly Ser Gly Ala Thr Asn Phe Ser Leu Leu Lys
465             470             475             480

Gln Ala Gly Asp Val Glu Glu Asn Pro Gly Pro Met Val Ser Lys Gly
            485             490             495

Glu Glu Leu Phe Thr Gly Val Val Pro Ile Leu Val Glu Leu Asp Gly
            500             505             510

Asp Val Asn Gly His Lys Phe Ser Val Ser Gly Glu Gly Glu Gly Asp
            515             520             525

Ala Thr Tyr Gly Lys Leu Thr Leu Lys Phe Ile Cys Thr Thr Gly Lys
    530             535             540

Leu Pro Val Pro Trp Pro Thr Leu Val Thr Thr Leu Thr Tyr Gly Val
545             550             555             560

Gln Cys Phe Ser Arg Tyr Pro Asp His Met Lys Gln His Asp Phe Phe
            565             570             575

Lys Ser Ala Met Pro Glu Gly Tyr Val Gln Glu Arg Thr Ile Phe Phe
            580             585             590

Lys Asp Asp Gly Asn Tyr Lys Thr Arg Ala Glu Val Lys Phe Glu Gly
            595             600             605

Asp Thr Leu Val Asn Arg Ile Glu Leu Lys Gly Ile Asp Phe Lys Glu
    610             615             620

Asp Gly Asn Ile Leu Gly His Lys Leu Glu Tyr Asn Tyr Asn Ser His
625             630             635             640

Asn Val Tyr Ile Met Ala Asp Lys Gln Lys Asn Gly Ile Lys Val Asn
            645             650             655

Phe Lys Ile Arg His Asn Ile Glu Asp Gly Ser Val Gln Leu Ala Asp
            660             665             670

His Tyr Gln Gln Asn Thr Pro Ile Gly Asp Gly Pro Val Leu Leu Pro
            675             680             685

Asp Asn His Tyr Leu Ser Thr Gln Ser Ala Leu Ser Lys Asp Pro Asn
    690             695             700

Glu Lys Arg Asp His Met Val Leu Leu Glu Phe Val Thr Ala Ala Gly
705             710             715             720

Ile Thr Leu Gly Met Asp Glu Leu Tyr Lys
```

```
                725                 730

<210> SEQ ID NO 77
<211> LENGTH: 726
<212> TYPE: PRT
<213> ORGANISM: Artificial Sequence
<220> FEATURE:
<223> OTHER INFORMATION: Synthetic

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Gly Gly Gly Gly
            100                 105                 110

Ser Gly Gly Gly Gly Ser Gly Gly Gly Ser Gln Val Gln Leu Val
            115                 120                 125

Glu Ser Gly Gly Gly Leu Val Lys Pro Gly Gly Ser Leu Arg Leu Ser
    130                 135                 140

Cys Ala Ala Ser Gly Phe Thr Phe Ser Glu Tyr Tyr Met Thr Trp Ile
145                 150                 155                 160

Arg Gln Ala Pro Gly Gln Gly Leu Glu Trp Val Ser Tyr Ile Ser Ser
                165                 170                 175

Ser Gly Phe Asn Ile Tyr Tyr Ala Asp Ser Val Lys Gly Arg Phe Thr
            180                 185                 190

Ile Ser Arg Asp Asn Ala Lys Asn Ser Leu Phe Leu Gln Met Asn Ser
            195                 200                 205

Leu Arg Val Glu Asp Thr Ala Val Tyr Tyr Cys Ala Arg Glu Gly Val
    210                 215                 220

Thr Asp Gly Met Asp Val Trp Gly Gln Gly Thr Thr Val Thr Val Ser
225                 230                 235                 240

Ser Gly Gly Gly Gly Ser Ile Glu Val Met Tyr Pro Pro Pro Tyr Leu
                245                 250                 255

Asp Asn Glu Lys Ser Asn Gly Thr Ile Ile His Val Lys Gly Lys His
            260                 265                 270

Leu Cys Pro Ser Pro Leu Phe Pro Gly Pro Ser Lys Pro Phe Trp Val
            275                 280                 285

Leu Val Val Val Gly Gly Val Leu Ala Cys Tyr Ser Leu Leu Val Thr
    290                 295                 300

Val Ala Phe Ile Ile Phe Trp Val Arg Ser Lys Arg Ser Arg Leu Leu
305                 310                 315                 320

His Ser Asp Tyr Met Asn Met Thr Pro Arg Arg Pro Gly Pro Thr Arg
                325                 330                 335

Lys His Tyr Gln Pro Tyr Ala Pro Pro Arg Asp Phe Ala Ala Tyr Arg
            340                 345                 350

Ser Arg Val Lys Phe Ser Arg Ser Ala Asp Ala Pro Ala Tyr Gln Gln
```

-continued

```
         355              360              365

Gly Gln Asn Gln Leu Tyr Asn Glu Leu Asn Leu Gly Arg Arg Glu Glu
    370              375              380

Tyr Asp Val Leu Asp Lys Arg Arg Gly Arg Asp Pro Glu Met Gly Gly
385              390              395              400

Lys Pro Arg Arg Lys Asn Pro Gln Glu Gly Leu Tyr Asn Glu Leu Gln
                405              410              415

Lys Asp Lys Met Ala Glu Ala Tyr Ser Glu Ile Gly Met Lys Gly Glu
            420              425              430

Arg Arg Arg Gly Lys Gly His Asp Gly Leu Tyr Gln Gly Leu Ser Thr
            435              440              445

Ala Thr Lys Asp Thr Tyr Asp Ala Leu His Met Gln Ala Leu Pro Pro
    450              455              460

Arg Gly Ser Gly Ala Thr Asn Phe Ser Leu Leu Lys Gln Ala Gly Asp
465              470              475              480

Val Glu Glu Asn Pro Gly Pro Met Val Ser Lys Gly Glu Glu Leu Phe
            485              490              495

Thr Gly Val Val Pro Ile Leu Val Glu Leu Asp Gly Asp Val Asn Gly
        500              505              510

His Lys Phe Ser Val Ser Gly Glu Gly Glu Gly Asp Ala Thr Tyr Gly
    515              520              525

Lys Leu Thr Leu Lys Phe Ile Cys Thr Thr Gly Lys Leu Pro Val Pro
    530              535              540

Trp Pro Thr Leu Val Thr Thr Leu Thr Tyr Gly Val Gln Cys Phe Ser
545              550              555              560

Arg Tyr Pro Asp His Met Lys Gln His Asp Phe Phe Lys Ser Ala Met
            565              570              575

Pro Glu Gly Tyr Val Gln Glu Arg Thr Ile Phe Phe Lys Asp Asp Gly
            580              585              590

Asn Tyr Lys Thr Arg Ala Glu Val Lys Phe Glu Gly Asp Thr Leu Val
            595              600              605

Asn Arg Ile Glu Leu Lys Gly Ile Asp Phe Lys Glu Asp Gly Asn Ile
    610              615              620

Leu Gly His Lys Leu Glu Tyr Asn Tyr Asn Ser His Asn Val Tyr Ile
625              630              635              640

Met Ala Asp Lys Gln Lys Asn Gly Ile Lys Val Asn Phe Lys Ile Arg
            645              650              655

His Asn Ile Glu Asp Gly Ser Val Gln Leu Ala Asp His Tyr Gln Gln
            660              665              670

Asn Thr Pro Ile Gly Asp Gly Pro Val Leu Leu Pro Asp Asn His Tyr
            675              680              685

Leu Ser Thr Gln Ser Ala Leu Ser Lys Asp Pro Asn Glu Lys Arg Asp
    690              695              700

His Met Val Leu Leu Glu Phe Val Thr Ala Ala Gly Ile Thr Leu Gly
705              710              715              720

Met Asp Glu Leu Tyr Lys
            725
```

<210> SEQ ID NO 78
<211> LENGTH: 731
<212> TYPE: PRT
<213> ORGANISM: Artificial Sequence
<220> FEATURE:
<223> OTHER INFORMATION: Synthetic -continued

```
<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg Gly Gly Gly
            100                 105                 110

Gly Ser Gly Gly Gly Gly Ser Gly Gly Gly Ser Gln Val Gln Leu
            115                 120                 125

Val Glu Ser Gly Gly Gly Leu Val Lys Pro Gly Gly Ser Leu Arg Leu
    130                 135                 140

Ser Cys Ala Ala Ser Gly Phe Thr Phe Ser Glu Tyr Tyr Met Thr Trp
145                 150                 155                 160

Ile Arg Gln Ala Pro Gly Gln Gly Leu Glu Trp Val Ser Tyr Ile Ser
            165                 170                 175

Ser Ser Gly Phe Asn Ile Tyr Tyr Ala Asp Ser Val Lys Gly Arg Phe
            180                 185                 190

Thr Ile Ser Arg Asp Asn Ala Lys Asn Ser Leu Phe Leu Gln Met Asn
        195                 200                 205

Ser Leu Arg Val Glu Asp Thr Ala Val Tyr Tyr Cys Ala Arg Glu Gly
    210                 215                 220

Val Thr Asp Gly Met Asp Val Trp Gly Gln Gly Thr Thr Val Thr Val
225                 230                 235                 240

Ser Ser Gly Gly Gly Gly Ser Thr Thr Thr Pro Ala Pro Arg Pro Pro
            245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
            275                 280                 285

Phe Ala Cys Asp Ile Tyr Ile Trp Ala Pro Leu Ala Gly Thr Cys Gly
    290                 295                 300

Val Leu Leu Leu Ser Leu Val Ile Thr Leu Tyr Cys Lys Arg Gly Arg
305                 310                 315                 320

Lys Lys Leu Leu Tyr Ile Phe Lys Gln Pro Phe Met Arg Pro Val Gln
            325                 330                 335

Thr Thr Gln Glu Glu Asp Gly Cys Ser Cys Arg Phe Pro Glu Glu Glu
            340                 345                 350

Glu Gly Gly Cys Glu Leu Arg Val Lys Phe Ser Arg Ser Ala Asp Ala
            355                 360                 365

Pro Ala Tyr Gln Gln Gly Gln Asn Gln Leu Tyr Asn Glu Leu Asn Leu
    370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
            405                 410                 415
```

-continued

```
Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
            435                 440                 445

Gln Gly Leu Ser Thr Ala Thr Lys Asp Thr Tyr Asp Ala Leu His Met
            450                 455                 460

Gln Ala Leu Pro Pro Arg Gly Ser Gly Ala Thr Asn Phe Ser Leu Leu
465                 470                 475                 480

Lys Gln Ala Gly Asp Val Glu Glu Asn Pro Gly Pro Met Val Ser Lys
                    485                 490                 495

Gly Glu Glu Leu Phe Thr Gly Val Val Pro Ile Leu Val Glu Leu Asp
            500                 505                 510

Gly Asp Val Asn Gly His Lys Phe Ser Val Ser Gly Glu Gly Glu Gly
            515                 520                 525

Asp Ala Thr Tyr Gly Lys Leu Thr Leu Lys Phe Ile Cys Thr Thr Gly
            530                 535                 540

Lys Leu Pro Val Pro Trp Pro Thr Leu Val Thr Thr Leu Thr Tyr Gly
545                 550                 555                 560

Val Gln Cys Phe Ser Arg Tyr Pro Asp His Met Lys Gln His Asp Phe
                    565                 570                 575

Phe Lys Ser Ala Met Pro Glu Gly Tyr Val Gln Glu Arg Thr Ile Phe
            580                 585                 590

Phe Lys Asp Asp Gly Asn Tyr Lys Thr Arg Ala Glu Val Lys Phe Glu
            595                 600                 605

Gly Asp Thr Leu Val Asn Arg Ile Glu Leu Lys Gly Ile Asp Phe Lys
            610                 615                 620

Glu Asp Gly Asn Ile Leu Gly His Lys Leu Glu Tyr Asn Tyr Asn Ser
625                 630                 635                 640

His Asn Val Tyr Ile Met Ala Asp Lys Gln Lys Asn Gly Ile Lys Val
                    645                 650                 655

Asn Phe Lys Ile Arg His Asn Ile Glu Asp Gly Ser Val Gln Leu Ala
            660                 665                 670

Asp His Tyr Gln Gln Asn Thr Pro Ile Gly Asp Gly Pro Val Leu Leu
            675                 680                 685

Pro Asp Asn His Tyr Leu Ser Thr Gln Ser Ala Leu Ser Lys Asp Pro
            690                 695                 700

Asn Glu Lys Arg Asp His Met Val Leu Leu Glu Phe Val Thr Ala Ala
705                 710                 715                 720

Gly Ile Thr Leu Gly Met Asp Glu Leu Tyr Lys
            725                 730
```

```
<210> SEQ ID NO 79
<211> LENGTH: 727
<212> TYPE: PRT
<213> ORGANISM: Artificial Sequence
<220> FEATURE:
<223> OTHER INFORMATION: Synthetic

<400> SEQUENCE: 79

Asp Ile Gln Met Thr Gln Ser Pro Ser Ser Leu Ser Ala Ser Val Gly
1                   5                   10                  15

Asp Arg Val Thr Ile Thr Cys Arg Ala Ser Gln Ser Ile Ser Ser Tyr
                    20                  25                  30

Leu Asn Trp Tyr Gln Gln Lys Pro Gly Lys Ala Pro Lys Leu Leu Ile
            35                  40                  45
```

-continued

```
Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg Gly Gly Gly
                100                 105                 110

Gly Ser Gly Gly Gly Gly Ser Gly Gly Gly Ser Gln Val Gln Leu
            115                 120                 125

Val Glu Ser Gly Gly Gly Leu Val Lys Pro Gly Gly Ser Leu Arg Leu
    130                 135                 140

Ser Cys Ala Ala Ser Gly Phe Thr Phe Ser Glu Tyr Tyr Met Thr Trp
145                 150                 155                 160

Ile Arg Gln Ala Pro Gly Gln Gly Leu Glu Trp Val Ser Tyr Ile Ser
                165                 170                 175

Ser Ser Gly Phe Asn Ile Tyr Tyr Ala Asp Ser Val Lys Gly Arg Phe
                180                 185                 190

Thr Ile Ser Arg Asp Asn Ala Lys Asn Ser Leu Phe Leu Gln Met Asn
            195                 200                 205

Ser Leu Arg Val Glu Asp Thr Ala Val Tyr Tyr Cys Ala Arg Glu Gly
    210                 215                 220

Val Thr Asp Gly Met Asp Val Trp Gly Gln Gly Thr Thr Val Thr Val
225                 230                 235                 240

Ser Ser Gly Gly Gly Gly Ser Ile Glu Val Met Tyr Pro Pro Pro Tyr
                245                 250                 255

Leu Asp Asn Glu Lys Ser Asn Gly Thr Ile Ile His Val Lys Gly Lys
                260                 265                 270

His Leu Cys Pro Ser Pro Leu Phe Pro Gly Pro Ser Lys Pro Phe Trp
            275                 280                 285

Val Leu Val Val Val Gly Gly Val Leu Ala Cys Tyr Ser Leu Leu Val
    290                 295                 300

Thr Val Ala Phe Ile Ile Phe Trp Val Arg Ser Lys Arg Ser Arg Leu
305                 310                 315                 320

Leu His Ser Asp Tyr Met Asn Met Thr Pro Arg Arg Pro Gly Pro Thr
                325                 330                 335

Arg Lys His Tyr Gln Pro Tyr Ala Pro Pro Arg Asp Phe Ala Ala Tyr
                340                 345                 350

Arg Ser Arg Val Lys Phe Ser Arg Ser Ala Asp Ala Pro Ala Tyr Gln
            355                 360                 365

Gln Gly Gln Asn Gln Leu Tyr Asn Glu Leu Asn Leu Gly Arg Arg Glu
    370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
            435                 440                 445

Thr Ala Thr Lys Asp Thr Tyr Asp Ala Leu His Met Gln Ala Leu Pro
    450                 455                 460
```

```
Pro Arg Gly Ser Gly Ala Thr Asn Phe Ser Leu Leu Lys Gln Ala Gly
465             470             475             480

Asp Val Glu Glu Asn Pro Gly Pro Met Val Ser Lys Gly Glu Glu Leu
            485             490             495

Phe Thr Gly Val Val Pro Ile Leu Val Glu Leu Asp Gly Asp Val Asn
            500             505             510

Gly His Lys Phe Ser Val Ser Gly Glu Gly Glu Gly Asp Ala Thr Tyr
            515             520             525

Gly Lys Leu Thr Leu Lys Phe Ile Cys Thr Thr Gly Lys Leu Pro Val
            530             535             540

Pro Trp Pro Thr Leu Val Thr Thr Leu Thr Tyr Gly Val Gln Cys Phe
545             550             555             560

Ser Arg Tyr Pro Asp His Met Lys Gln His Asp Phe Phe Lys Ser Ala
            565             570             575

Met Pro Glu Gly Tyr Val Gln Glu Arg Thr Ile Phe Phe Lys Asp Asp
            580             585             590

Gly Asn Tyr Lys Thr Arg Ala Glu Val Lys Phe Glu Gly Asp Thr Leu
            595             600             605

Val Asn Arg Ile Glu Leu Lys Gly Ile Asp Phe Lys Glu Asp Gly Asn
            610             615             620

Ile Leu Gly His Lys Leu Glu Tyr Asn Tyr Asn Ser His Asn Val Tyr
625             630             635             640

Ile Met Ala Asp Lys Gln Lys Asn Gly Ile Lys Val Asn Phe Lys Ile
            645             650             655

Arg His Asn Ile Glu Asp Gly Ser Val Gln Leu Ala Asp His Tyr Gln
            660             665             670

Gln Asn Thr Pro Ile Gly Asp Gly Pro Val Leu Leu Pro Asp Asn His
            675             680             685

Tyr Leu Ser Thr Gln Ser Ala Leu Ser Lys Asp Pro Asn Glu Lys Arg
            690             695             700

Asp His Met Val Leu Leu Glu Phe Val Thr Ala Ala Gly Ile Thr Leu
705             710             715             720

Gly Met Asp Glu Leu Tyr Lys
            725
```

<210> SEQ ID NO 80
<211> LENGTH: 732
<212> TYPE: PRT
<213> ORGANISM: Artificial Sequence
<220> FEATURE:
<223> OTHER INFORMATION: Synthetic

<400> SEQUENCE: 80

```
Asp Ile Gln Met Thr Gln Ser Pro Ser Ser Leu Ser Ala Ser Val Gly
1               5               10              15

Asp Arg Val Thr Ile Thr Cys Gln Ala Ser Gln Asp Ile Ser Asn Tyr
            20              25              30

Leu Asn Trp Tyr Gln Gln Lys Arg Gly Lys Ala Pro Lys Leu Leu Ile
            35              40              45

Tyr Asp Ala Ser Ile Leu Glu Thr Gly Val Pro Ser Arg Phe Ser Gly
            50              55              60

Ser Gly Ser Gly Thr Asp Phe Thr Phe Thr Ile Ser Ser Leu Gln Pro
65              70              75              80

Glu Asp Ile Ala Thr Tyr Phe Cys Gln Gln Phe Asp Asn Val Pro Leu
            85              90              95
```

-continued

```
Thr Phe Gly Gly Gly Thr Lys Val Glu Ile Lys Gly Gly Gly Gly Ser
            100                 105                 110

Gly Gly Gly Gly Ser Gly Gly Gly Ser Glu Val Gln Leu Val Glu
            115                 120                 125

Ser Gly Gly Gly Leu Val Gln Pro Gly Arg Ser Leu Arg Leu Ser Cys
        130                 135                 140

Ala Ala Ser Gly Phe Thr Phe Asp Asp Tyr Ala Met His Trp Val Arg
145                 150                 155                 160

Gln Ala Pro Gly Lys Gly Leu Glu Trp Val Ser Gly Ile Ser Trp Asn
                165                 170                 175

Ser Gly Ser Ile Ala Tyr Ala Asp Ser Val Lys Gly Arg Phe Thr Ile
            180                 185                 190

Ser Arg Asp Asn Ala Lys Asn Ser Leu Tyr Leu Gln Met Asn Ser Leu
            195                 200                 205

Arg Ser Glu Asp Thr Ala Leu Tyr His Cys Ala Lys Asp Trp Arg Arg
        210                 215                 220

Thr Asn Tyr Tyr Gly Met Asp Val Trp Gly Gln Gly Thr Thr Val Thr
225                 230                 235                 240

Val Ser Ser Gly Gly Gly Gly Ser Thr Thr Thr Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
        275                 280                 285

Asp Phe Ala Cys Asp Ile Tyr Ile Trp Ala Pro Leu Ala Gly Thr Cys
        290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
            355                 360                 365

Ala Pro Ala Tyr Gln Gln Gly Gln Asn Gln Leu Tyr Asn Glu Leu Asn
        370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Gly Lys Gly His Asp Gly Leu
            435                 440                 445

Tyr Gln Gly Leu Ser Thr Ala Thr Lys Asp Thr Tyr Asp Ala Leu His
        450                 455                 460

Met Gln Ala Leu Pro Pro Arg Gly Ser Gly Ala Thr Asn Phe Ser Leu
465                 470                 475                 480

Leu Lys Gln Ala Gly Asp Val Glu Glu Asn Pro Gly Pro Met Val Ser
                485                 490                 495

Lys Gly Glu Glu Leu Phe Thr Gly Val Val Pro Ile Leu Val Glu Leu
            500                 505                 510

Asp Gly Asp Val Asn Gly His Lys Phe Ser Val Ser Gly Glu Gly Glu
```

-continued

```
              515                  520                  525

Gly Asp Ala Thr Tyr Gly Lys Leu Thr Leu Lys Phe Ile Cys Thr Thr
    530                  535                  540

Gly Lys Leu Pro Val Pro Trp Pro Thr Leu Val Thr Thr Leu Thr Tyr
545                  550                  555                  560

Gly Val Gln Cys Phe Ser Arg Tyr Pro Asp His Met Lys Gln His Asp
                565                  570                  575

Phe Phe Lys Ser Ala Met Pro Glu Gly Tyr Val Gln Glu Arg Thr Ile
                580                  585                  590

Phe Phe Lys Asp Asp Gly Asn Tyr Lys Thr Arg Ala Glu Val Lys Phe
                595                  600                  605

Glu Gly Asp Thr Leu Val Asn Arg Ile Glu Leu Lys Gly Ile Asp Phe
    610                  615                  620

Lys Glu Asp Gly Asn Ile Leu Gly His Lys Leu Glu Tyr Asn Tyr Asn
625                  630                  635                  640

Ser His Asn Val Tyr Ile Met Ala Asp Lys Gln Lys Asn Gly Ile Lys
                645                  650                  655

Val Asn Phe Lys Ile Arg His Asn Ile Glu Asp Gly Ser Val Gln Leu
                660                  665                  670

Ala Asp His Tyr Gln Gln Asn Thr Pro Ile Gly Asp Gly Pro Val Leu
                675                  680                  685

Leu Pro Asp Asn His Tyr Leu Ser Thr Gln Ser Ala Leu Ser Lys Asp
    690                  695                  700

Pro Asn Glu Lys Arg Asp His Met Val Leu Leu Glu Phe Val Thr Ala
705                  710                  715                  720

Ala Gly Ile Thr Leu Gly Met Asp Glu Leu Tyr Lys
                725                  730

<210> SEQ ID NO 81
<211> LENGTH: 728
<212> TYPE: PRT
<213> ORGANISM: Artificial Sequence
<220> FEATURE:
<223> OTHER INFORMATION: Synthetic

<400> SEQUENCE: 81

Asp Ile Gln Met Thr Gln Ser Pro Ser Ser Leu Ser Ala Ser Val Gly
1               5                  10                  15

Asp Arg Val Thr Ile Thr Cys Gln Ala Ser Gln Asp Ile Ser Asn Tyr
                20                  25                  30

Leu Asn Trp Tyr Gln Gln Lys Arg Gly Lys Ala Pro Lys Leu Leu Ile
            35                  40                  45

Tyr Asp Ala Ser Ile Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Phe Asp Asn Val Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Glu Val Gln Leu Val Glu
            115                 120                 125

Ser Gly Gly Gly Leu Val Gln Pro Gly Arg Ser Leu Arg Leu Ser Cys
    130                 135                 140

Ala Ala Ser Gly Phe Thr Phe Asp Asp Tyr Ala Met His Trp Val Arg
```

```
145               150               155               160

Gln Ala Pro Gly Lys Gly Leu Glu Trp Val Ser Gly Ile Ser Trp Asn
              165               170               175

Ser Gly Ser Ile Ala Tyr Ala Asp Ser Val Lys Gly Arg Phe Thr Ile
              180               185               190

Ser Arg Asp Asn Ala Lys Asn Ser Leu Tyr Leu Gln Met Asn Ser Leu
              195               200               205

Arg Ser Glu Asp Thr Ala Leu Tyr His Cys Ala Lys Asp Trp Arg Arg
              210               215               220

Thr Asn Tyr Tyr Gly Met Asp Val Trp Gly Gln Gly Thr Thr Val Thr
225               230               235               240

Val Ser Ser Gly Gly Gly Gly Ser Ile Glu Val Met Tyr Pro Pro Pro
              245               250               255

Tyr Leu Asp Asn Glu Lys Ser Asn Gly Thr Ile Ile His Val Lys Gly
              260               265               270

Lys His Leu Cys Pro Ser Pro Leu Phe Pro Gly Pro Ser Lys Pro Phe
              275               280               285

Trp Val Leu Val Val Val Gly Gly Val Leu Ala Cys Tyr Ser Leu Leu
              290               295               300

Val Thr Val Ala Phe Ile Ile Phe Trp Val Arg Ser Lys Arg Ser Arg
305               310               315               320

Leu Leu His Ser Asp Tyr Met Asn Met Thr Pro Arg Arg Pro Gly Pro
              325               330               335

Thr Arg Lys His Tyr Gln Pro Tyr Ala Pro Pro Arg Asp Phe Ala Ala
              340               345               350

Tyr Arg Ser Arg Val Lys Phe Ser Arg Ser Ala Asp Ala Pro Ala Tyr
              355               360               365

Gln Gln Gly Gln Asn Gln Leu Tyr Asn Glu Leu Asn Leu Gly Arg Arg
              370               375               380

Glu Glu Tyr Asp Val Leu Asp Lys Arg Arg Gly Arg Asp Pro Glu Met
385               390               395               400

Gly Gly Lys Pro Arg Arg Lys Asn Pro Gln Glu Gly Leu Tyr Asn Glu
              405               410               415

Leu Gln Lys Asp Lys Met Ala Glu Ala Tyr Ser Glu Ile Gly Met Lys
              420               425               430

Gly Glu Arg Arg Arg Gly Lys Gly His Asp Gly Leu Tyr Gln Gly Leu
              435               440               445

Ser Thr Ala Thr Lys Asp Thr Tyr Asp Ala Leu His Met Gln Ala Leu
              450               455               460

Pro Pro Arg Gly Ser Gly Ala Thr Asn Phe Ser Leu Leu Lys Gln Ala
465               470               475               480

Gly Asp Val Glu Glu Asn Pro Gly Pro Met Val Ser Lys Gly Glu Glu
              485               490               495

Leu Phe Thr Gly Val Val Pro Ile Leu Val Glu Leu Asp Gly Asp Val
              500               505               510

Asn Gly His Lys Phe Ser Val Ser Gly Glu Gly Glu Gly Asp Ala Thr
              515               520               525

Tyr Gly Lys Leu Thr Leu Lys Phe Ile Cys Thr Thr Gly Lys Leu Pro
              530               535               540

Val Pro Trp Pro Thr Leu Val Thr Thr Leu Thr Tyr Gly Val Gln Cys
545               550               555               560

Phe Ser Arg Tyr Pro Asp His Met Lys Gln His Asp Phe Phe Lys Ser
              565               570               575
```

-continued

```
Ala Met Pro Glu Gly Tyr Val Gln Glu Arg Thr Ile Phe Phe Lys Asp
            580                 585                 590

Asp Gly Asn Tyr Lys Thr Arg Ala Glu Val Lys Phe Glu Gly Asp Thr
            595                 600                 605

Leu Val Asn Arg Ile Glu Leu Lys Gly Ile Asp Phe Lys Glu Asp Gly
    610                 615                 620

Asn Ile Leu Gly His Lys Leu Glu Tyr Asn Tyr Asn Ser His Asn Val
625                 630                 635                 640

Tyr Ile Met Ala Asp Lys Gln Lys Asn Gly Ile Lys Val Asn Phe Lys
                645                 650                 655

Ile Arg His Asn Ile Glu Asp Gly Ser Val Gln Leu Ala Asp His Tyr
            660                 665                 670

Gln Gln Asn Thr Pro Ile Gly Asp Gly Pro Val Leu Leu Pro Asp Asn
            675                 680                 685

His Tyr Leu Ser Thr Gln Ser Ala Leu Ser Lys Asp Pro Asn Glu Lys
    690                 695                 700

Arg Asp His Met Val Leu Leu Glu Phe Val Thr Ala Ala Gly Ile Thr
705                 710                 715                 720

Leu Gly Met Asp Glu Leu Tyr Lys
                725
```